(12) United States Patent
Gilchrist et al.

(10) Patent No.: US 7,208,279 B2
(45) Date of Patent: Apr. 24, 2007

(54) METHOD FOR IDENTIFYING INHIBITORS OF G PROTEIN COUPLED RECEPTOR SIGNALING

(75) Inventors: Annette Gilchrist, Barrington, IL (US); Heidi M. Hamm, Nashville, TN (US)

(73) Assignee: Caden Biosciences, Inc., Madison, WI (US)

( * ) Notice: Subject to any disclaimer, the term of this patent is extended or adjusted under 35 U.S.C. 154(b) by 140 days.

(21) Appl. No.: 09/852,910

(22) Filed: May 11, 2001

(65) Prior Publication Data

US 2003/0096297 A1    May 22, 2003

Related U.S. Application Data

(60) Provisional application No. 60/275,472, filed on Mar. 14, 2001.

(51) Int. Cl.
*G01N 33/53* (2006.01)
*C12Q 1/70* (2006.01)

(52) U.S. Cl. ............... 435/7.1; 435/6; 435/4; 435/DIG. 15; 435/DIG. 14

(58) Field of Classification Search .......... 435/7.1, 435/6, 4, DIG. 15, DIG. 14; 530/350, 324
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 5,034,506 A | 7/1991 | Summerton et al. | |
| 5,733,731 A | 3/1998 | Schatz et al. | |
| 5,880,972 A | 3/1999 | Horlbeck | |
| 5,892,014 A * | 4/1999 | Coughlin et al. ........ | 536/23.5 |
| 5,955,575 A | 9/1999 | Peri et al. | |
| 6,087,186 A | 7/2000 | Cargill et al. | |
| 6,156,511 A | 12/2000 | Schatz et al. | |
| 6,184,223 B1 | 2/2001 | Kahn et al. | |
| 6,300,312 B1 | 10/2001 | Chemtob et al. | |
| 6,617,114 B1 | 9/2003 | Fowlkes et al. | |
| 6,864,060 B1 | 3/2005 | Fowlkes et al. | |
| 6,864,229 B2 | 3/2005 | Kuliopulos et al. | |
| 2004/0220198 A1 | 11/2004 | Haldar et al. | |

FOREIGN PATENT DOCUMENTS

WO    WO 98/19162    *    5/1998
WO    WO 98/19162 A1    5/1998

OTHER PUBLICATIONS

Hamm et al., "Site of G Protein Binding to Rhodopsin Mapped with Synthetic Peptides from the α Subunit", *Science*, vol. 241:832-835, 1988.
Osawa and Weiss, "The Effect of Carboxyl-terminal Mutagenesis of $G_t\alpha$ on Rhodopsin and Guanine Nucleotide binding*", *J. Biol. Chem.*, vol. 270, No. 52:31052-31058, 1995.
Garcia et al., "Transducin-α C-terminal mutations prevent activation by rhodopsin: a new assay using recombinant proteins expressed in cultured cells", *EMBO J.*, vol. 14, No. 18:4460-4469, 1995.
Sullivan et al., "Identification of receptor contact site involved in receptor-G protein coupling", *Nature*, 330:758-760, 1987.
Rasenick et al., "Synthetic Peptides as Probes for G Protein Function", *J. Biol. Chem.*, vol. 269:21519-21525, 1994.
West, et al., "Pertussie Toxin-catalyzed ADP-ribosylation of Transducin", *J. Biol. Chem.*, vol. 260, No. 27:14428-14430, 1985.
Conklin, et al., "Substitution of Three amino acids switches receptor specificity of $G_q\alpha$ to that of $G_i\alpha$", *Nature*, vol. 363:274-276, 1993.
Conklin, et al., "Carboxyl-Terminal Mutations of $G_{q\alpha}$ and $G_{s\alpha}$ That Alter the Fidelity of Receptor Activation", *Mol. Pharmacol.*, 50:885-890, 1996.
König, et al., "Three cytoplasmic loops of rhodopsin interact with transducin", *Proc. Natl. Acad. Sci. USA*, vol. 86:6878-6882, 1989.
Acharya et al., "Transducin-α C-terminal Peptide Binding site Consists of C-D and E-F Loops of Rhodopsin*", *J. Biol. Chem.*, vol. 272:6519-6524, 1997.
Verrall et al. "The Thrombin Receptor Second Cytoplasmic Loop Confers Coupling to $G_q$-like G Proteins in Chimeric Receptors", *J. Biol. Chem.*, vol. 272:6898-6902, 1997.
Hamm and Gilchrist, "Heterotrimeric G proteins", *Curr., Opin. Cell Biol.*, 8:189-196, 1996.
Gilchrist, et al., "Antagonists of the Receptor-G Protein Interface Block G$_i$-coupled Signal Transduction*", *J. Biol. Chem.*, vol. 273, No. 24:14912-14919, 1998.
Martin, et al., "Potent Peptide Analogues of a G Protein Receptor-binding Region Obtained with a combinatorial Library*", *J. Biol. Chem.*, vol. 271, No. 1:361-366, 1996.
Sondek, et al., "GTPase mechanism of Gproteins from the 1.7-Å crystal structure of transducin α—GDP—AIF$_4$". *Nature*, vol. 372, No. 17:276-279, 1994.
Lambright, et al., "Structural determinants for activation of the α-subunit of a heterotrimeric G protein", *Nature*, vol. 369:621-628, 1994.
Lambright, et al., "The 2.0Å crystal structure of a heterotrimeric G protein", *Nature*, vol. 379:311-319, 1996.
Sondek, et al., "Crystal structure of a $G_A$ protein βγ dimer at 2.1Å resolution", *Nature*, vol. 379:369-374, 1996.
Mixon, et al., "Tertiary and Quaternary Structural Changes in $G_{i\alpha 1}$ Induced by GTP Hydrolysis", *Science*, vol. 270:954-960, 1995.

(Continued)

Primary Examiner—T. D. Wessendorf
(74) Attorney, Agent, or Firm—Rothwell, Figg, Ernst & Manbeck pc

(57) ABSTRACT

This invention relates to methods for identifying peptides and other compounds which block G protein coupled receptor mediated signaling with high affinity and specificity. Assays developed in conjunction with these methods also are disclosed.

5 Claims, 21 Drawing Sheets

OTHER PUBLICATIONS

Gilchrist, et al., A dominant-Negative Strategy for Studying Roles of G Proteins in Vivo*, *J. of Biol. Chem.*, vol. 274, No. 10:6610-6616, 1999.

Kostenis, et al., "Molecular Basis of Receptor/G Protein Coupling Selectivity Studied by Coexpression of Wild Type and Mutant m2 Muscarinic Receptors with Mutant $G\alpha_q$ Subunits",*Biochem.*, vol. 36, No. 6:1487-1495, 1997.

Onrust, et al., "Receptor and $\beta\gamma$ Binding Sites in the $\alpha$ Subunit of the Retinal G Protein Transducin", *Science*, vol. 275:381-383, 1997.

Mazzoni and Hamm, "Interaction of Transducin with Light-activated Rhodopsin Protects It from Proteolytic Digestion by Trypsin*", *J. Biol. Chem.*, vol. 271, No. 47:30034-30040, 1996.

Bae, et al., "Molecular Determinants of Selectivity in 5-Hydroxytryptamine $_{1B}$ Receptor-G Protein Interactions*", *J. Biol. Chem.*, vol. 272, No. 51:32071-32077, 1997.

Gates, et al., Affinity Selective Isolation of Ligands from Peptide Libraries Through Display on a lac Repressor "Headpiece Dimer", *J. Mol. Biol.*, 255, 373-386, 1996.

Lichtarge, et al., "Evolutionarily conserved $G\alpha\beta\gamma$ binding surfaces support a model of the G protein-receptor complex", *Proc. Natl. Acad. Sci. USA*, vol. 93:7507-7511, 1996.

Adang, A.E., et al., "The contribution of combinatorial chemistry to lead generation: an interim analysis," *Curr. Med. Chem.* 8(9):985-998, 2001 (Abstract Only).

Bala, M., et al., "Novel peptidomimics as angiotensin-converting enzyme inhibitors: a combinatorial approach," *Bioorg. Med. Chem.* 10(11):3685-91, 2002 (Abstract Only).

Ley, S.V., et al., "Solid-supported reagents for multi-step organic synthesis: preparation and application," *Farmaco* 57(4):321-30, 2002 (Abstract Only).

Azpiazu, Inaki, et al., "A G Protein $\gamma$ Subunit-specific Peptide Inhibits Muscarinic Receptor Signaling," *The Journal of Biological Chemistry* 274(50):35305-35308, Dec. 10, 1999.

Blahos, Jaroslav, et al., "A Novel Site on the $G\alpha$-protein That Recognizes Heptahelical Receptors," *The Journal of Biological Chemistry* 276(5):3262-3269, Feb. 2, 2001.

Aris et al., "Structural requirements for the stabilization of metarhodopsin II by the C terminus of the $\alpha$ subunit of Transducin," *J. Biol. Chem.*, 276(4):2333-2339, 2001.

Buck et al., "Role of dynamic interactions in effective signal transfer for $G\beta$ stimulation of phospholipase C-$\beta$2," *J. Biol. Chem.*, 277(51):49707-49715, 2002.

Cheadle et al., "Identification of a Src SH3 domain binding motif by screening a random phage display library," *J. Biol. Chem.*, 269(39):24034-24039, 1994.

Copeland, Robert A., "Mechanistic considerations in high-throughput screening," *Analytical Biochemistry*, 320:1-12, 2003.

Cull et al., "Screening for receptor ligands using large libraries of peptides linked to the C terminus fo the *lac* repressor," *Proc. Natl. Acad. Sci.*, 89:1865-1869, 1992.

Cwirla et al., "Peptide agonist of the thrombopoietin receptor as potent as the natural cytokine," *Science*, 276:1696-1699, Jun. 13, 1997.

Dani, Maria, "Peptide display libraries: design and construction," *J. Of Receptor & Signal Transduction Research*, 21(4):469-488, 2001.

Francken et al., "Human 5-hydroxytryptamine$_{5A}$ receptors activate coexpressed $G_i$ and $G_o$ proteins in *Spodoptera frugiperda* 9 cells," *Mol. Pharm.*, 57:1034-1044, 2000.

Gilchrist et al., "Use of peptides-on-plasmids combinatorial library to identify high-affinity peptides that bind rhodopsin," *Methods in Enzymology*, 315:388-404, 2000.

Glass et al., Agonist selective regulation of G proteins by cannabinoid $CB_1$ and $CB_2$ receptors, *Mol. Pharmacol.*, 56:1362-1369, 1999.

Hall, David A., "Modeling the functional effects of allosteric modulators at pharmacological receptors: an extension of the two-state model of receptor activation," *Mol. Pharmacol.*, 58:1412-1423, 2000.

Kay et al., "Screening phage-displayed combinatorial peptide libraries," *Methods*, 24:240-246, 2001.

Koivunen et al., "Identification of receptor ligands with phage display peptide libraries," *J. Nucl. Med.*, 40:883-888, 1999.

Martin et al., "Potent peptide analogues of a G protein receptor-binding region obtained with a combinatorial library," *J. Biol. Chem.*, 271(1):361-366, 1996.

Neubig et al., "International union of pharmacology committee on receptor nomenclature and drug classification. XXXVIII. Update on terms and symbols in quantitative pharmacology," *Pharmacol. Rev.*, 55:597-606, 2003.

Rodi et al., "Phage-display technology-finding a needle in a vast molecular haystack," *Current Opinion in Biotechnology*, 10:87-93, 1999.

Schatz et al., "Screening of peptide libraries linked to *lac* receptor," *Methods in Enzymology*,267:171-191, 1996.

Sundberg, Steven A., "High-throughput and ultra-high-throughput screening: solution- and cell-based approaches," *Current Opinion in Biotechnology*, 11:47-53, 2000.

Szardenings et al., "New highly specific agonistic peptides for human melanocortin MC$_4$ receptor," *Peptides*, 21:239-243, 2000.

Windh et al., "Differential coupling of the sphingosine 1-phosphate receptors Edg-1, Edg-3, and H218/Edg-5 to the $G_i$, $G_q$, and G12 families of heterotrimeric G Proteins," *J. Biol. Chem.*, 274(39):27351-27358, 1999.

Zwick et al., "Phage-displayed peptide libraries," *Current Opinion in Biotechnology*, 9:427-436, 1998.

Jones, Philip G., et al., "Non-Binding Site Modulation of G Protein-Coupled Receptor Signalling," *Exp. Opin. Ther. Patents* 9(12):1641-1654, 1999.

Stephen W. Edwards, et al., "Localization of G-Protein-Coupled Receptors in Health and Disease," *TIPS* 21: 304-308, Aug. 2000.

Shahab A. Akhter, et al., "Targeting the Receptor-$G_q$ Interface to Inhibit in Vivo Pressure Overload Myocardial Hypertrophy," *Science*, 280: 574-577, Apr. 24, 1998.

Thomas Carell, et al., "New Promise in Combinatorial Chemistry: Synthesis, Characterization, and Screening of Small-Molecule Libraries in Solution," *Chemistry & Biology* 2: 171-183, Mar. 1995.

Mark A. Wall, et al. "The Structure of the G Protein Heterotrimer $G_{i\alpha1}\beta_1\gamma_2$", *Cell* 83: 1047-1058, Dec. 15, 1995.

David E. Coleman, et al., "Structures of Active Conformations of $G_{i\alpha1}$ and the Mechanism of GTP Hydrolysis," *Science* 265: 1405-1412, Sep. 2, 1994.

Chad A. Ellis, et al., Thrombin Induces Proteinase-Activated Receptor-1 Gene Expression in Endothelial Cells Via Activation of $G_i$-Linked Ras/Mitogen-Activated Protein Kinase Pathway, *J. of Biol. Chem.*, 274 (19): 13718-13727, May 7, 1999.

Bo Yu, et al. "Inhibition of Subsets of G Protein-Coupled Receptors By Empty Mutants of G Protein $\alpha$ Subunits in $G_0$, $G_{11}$, and $G_{16}$," *J. of Biol. Chem.*, 275 (1): 71-76, Jan. 7, 2000.

Bo Yu, et al., "Interaction of the Xanthine Nucleotide Binding $G\alpha$ Mutant With G Protein-Coupled Receptors," *J. of Biol. Chem.* 273(46):30183-30188, Nov. 13, 1998.

Jie Liu, et al., "Identification of a Receptor/G-Protein Contact Site Critical for Signaling Specificity and G-Protein Activation," *Proc. Natl. Acad. Sci. USA* 92: 11642-11646, Dec. 1995.

Grigory Krapivinsky, et al., "$G_{\beta\gamma}$ Binding to GIRK4 Subunit Is Critical for G Protein-Gated $K^+$ Channel Activation," *J. of Biol. Chem.* 273(27): 16946-16952, Jul. 3, 1998.

Grigory Krapivinsky, et al. "$G_{\beta\gamma}$ Binding to GIRK4 Subunit Is Critical for G Protein-Gated $K^+$ Channel, $I_{KACh}$," *J. of Biol. Chem.* 270(49): 29059-29062, Dec. 8, 1995.

Lutz F. Tietze, et al., "Domino Reactions for Library Synthesis of Small Molecules in Combinatorial Chemistry," *Curr. Opin. in Chem. Biol.* 2: 363-371, 1998.

Margaret O. Sowell, et al., "Targeted Inactivation of $\alpha_{i2}$ or $\alpha_{i3}$ Disrupts Activation of the Cardiac Muscarinic $K^+$ Channel, $I_{K+Ach}$, in Intact Cells," *Proc. Natl. Acad. Sci. USA* 94: 7921-7926, Jul. 1997.

Heidi E. Hamm, "The Many Faces of G Protein Signaling," *J. of Biol. Chem.* 273(2): 669-672, Jan. 9, 1998.

C. Höller, et al., "G Proteins As Drug Targets," *Cell. Mol. Life Sci.* 55: 257-270, 1999.

Peter J. Schatz, et al., "Screening of Peptide Libraries Linked to Lac Repressor," *Methods in Enzymology* 267: 171-191, 1996.

Barker et al., "Constitutively Active 5-Hydroxytryptamine$_{2C}$ Receptors Reveal Novel Inverse Agonist Activity of Receptor Ligands", J. Biol. Chem., 269(16):11687-11690, 1994.

Bertin et al., "Functional Expression of the Human Serotonin 5-HT1A Receptor in *Escherichia coli*", J. Biol. Chem., 267(12):8200-8206, 1992.

Chidiac et al., "Inverse Agonist Activity of β-Adrenergic Antagonists", Mol. Pharmacol., 45:490-499, 1994.

Costa and Herz, "Antagonists with negative intrinsic activity at σ opioid receptors coupled to GTP-binding proteins", proc. Natl. Acad. Sci. USA, 86:7321-7325, 1989.

Costa et al., "Drug Efficacy at Guanine Nucleotide-Binding Regulatory Protein-Linked Receptors: Thermodynamic Interpretation of Negative Antagonism and of Receptor Activity in the Absence of Ligand", Mol. Pharmacol., 41:549-560, 1992.

Farfel et al., "The Expanding Spectrum of G Protein Diseases", New Engl. J. Med., 340(13): 1012-1020, 1999.

Flanagan et al., "Advances in understanding gonadotrophin-releasing hormone receptor structure and ligand interactions", Rev. of Reprod., 2:113-120, 1997.

Ford et al., "Molecular Basis for Interactions of G Protein βγ Subunits with Effectors", Science, 280:1271-1274, 1998.

Gilchrist et al., "Gα COOH-Terminal Minigene Vectors Dissect Heterotrimeric G Protein Signaling", Protocols: Science's STKE, 118, 2002. (Abstract only).

Greco et al. "Cancer Gene Therapy: 'Delivery, Delivery, Delivery'", Frontiers in Bioscience, 7:1516-1524, 2002.

Gromoll et al., "Functional and clinical consequences of mutations in the FSH receptor", Mol. and Cell. Endocrinol., 125:177-182, 1996.

Hasegawa et al. "Two Isoforms of the Prostaglandin E Receptor EP3 Subtype Different in Agonist-independent Constitutive Activity", J. Biol. Chem., 271(4):1857-1860, 1996.

Inanobe et al., "Molecular cloning and characterization of a novel splicing variant of the Kir3.2 subunit predominantly expressed in mouse testis", J. Physiol., 521.1:19-30,1999.

Leeb-Lundberg et al., "Antonists of Bradykinin That Stabilize a G-protein-uncoupled State of the B2 Receptor Act as Inverse Agonists in Rat Myometrial Cells", J. Biol. Chem., 269(42):25970-25973, 1994.

Lewin, B., "G proteins may activate or inhibit target proteins," Genes VII, Oxford University Press 2000, Chapter 26, pp. 809-811.

Lipinski et al., "Experimental and computational approaches to estimate solubility and permeability in drug discovery and development settings", Adv. Drug Delivery Rev., 23:3-25, 1997.

Matsuoka et al., "Sequence analysis of cDNA and genomic DNA for a putative pertussis toxin-insensitive guanine nucleotide-bindings regulatory protein α subunit", Proc. Natl., Acad. Sci. USA, 85:5384-5388, 1988.

Nielsen et al., "Sequence-selective recognition of DNA by strand displacement with a thymine-substituted polyamide", Science, 254(5037):1497-1500, 1991. (Abstract only).

Pei et al., "A constitutively active mutant β$_2$-adrenergic receptor is constitutively desensitized and phosphorylated", Proc. Natl. Acad. Sci. USA, 91:2699-2702, 1994.

Ren et al., "Constitutively Active Mutants of the α$_2$-Adrenergic Receptor", J. Biol. Chem., 268(22):16483-16487, 1993.

Samama et al., "Negative Antagonists Promote an Inactive Conformation of the β$_2$-Adrenergic Receptor", Mol. Pharmacol., 45:390-394, 1994.

Tiberi and Caron, "High Agonist-independent Activity is a Distinguishing Feature of the Dopamine D1B Receptor Subtype", J. Biol. Chem., 269(45):27925-27931, 1994.

Vanhauwe et al., "Thrombin Receptors Activate G$_o$ Proteins in Endothelial Cells to Regulate Intracellular Calcium and Cell Shape Changes", J. Biol. Chem., 277(37): 34143-34149, 2002.

Vassart et al., "The G Protein-coupled Receptor Family and One of its Members, the TSH Receptor", Ann. N.Y. Acad. Sci., 766:23-30, 1995.

\* cited by examiner

Bind GPCR to well

Add peptide library

Use parent peptide to compete map of pJS142 vector

METHOD FOR IDENTIFYING INHIBITORS OF G PROTEIN COUPLED RECEPTOR SIGNALING

This application claims priority from now abandoned provisional application 60/275,472, filed Mar. 14, 2001.

BACKGROUND OF THE INVENTION

1. Technical Field

The present invention generally pertains to the field of modulating G protein-coupled receptors (GPCR) and of identifying and preparing G protein coupled receptor inhibiting compounds.

2. Description of the Background Art

A great number of chemical messengers exert their effects on cells by binding to G protein-coupled receptors. Ligand binding to those receptors is transduced by heterotrimeric G proteins into intracellular responses. Four main classes of G proteins are distinguishable: Gs, Gi, Gq and G12. G protein-coupled receptors (GPCR) include a wide range of biologically active receptors, such as hormone receptors, viral receptors, growth factor receptors, chemokine receptors, sensory receptors and neuroreceptors. These receptors are activated by the binding of ligand to an extracellular binding site and mediate their actions through the various G proteins. The molecular interactions that occur between the receptor and the G protein are fundamental to the transduction of environmental signals into specific cellular responses. The G proteins themselves play important roles in determining the specificity and temporal characteristics of the cellular response to the ligand-binding signal.

In the inactive state, G proteins are heterotrimeric, consisting of one $\alpha$, one $\beta$ and one $\gamma$ subunit, and a bound deoxyguanosine diphosphate (GDP). Receptor-catalyzed guanine nucleotide exchange resulting in deoxyguanosine triphosphate (GTP) binding to the $\alpha$ subunit activates the G protein. $G\alpha$-GTP dissociates from the $G\beta\gamma$ subunits, allowing the $G\beta\gamma$ dimer and the $G\alpha$-GTP subunit each to activate downstream effectors. Hydrolysis of GTP to GDP deactivates the complex and turns off the cellular response.

G protein-coupled receptors have seven transmembrane helices which form, on the intracellular side of the membrane, the G protein binding domain. Experiments have suggested that activation of the receptor by ligand binding changes conformation of the receptor, unmasking G protein binding sites on the intracellular face of the receptor. The heterotrimeric G protein interacts with GPCR in a multi-site fashion with the major site of contact between them at the carboxyl terminus of the $G\alpha$ subunit. Hamm et al., *Science* 241:832–5, 1998; Osawa and Weiss, *J. Biol. Chem.* 270: 31052–8, 1995; Garcia et al., *EMBO J.* 14:4460–9, 1995; Sullivan et al., *J. Biol. Chem.* 269:21519–21525, 1994; West et al., *J. Biol. Chem.* 260:14428–30, 1985.

The carboxyl terminal 11 amino acids are most important to receptor interaction and to the specificity of this interaction, Martin et al., *J. Biol. Chem.* 271:361–366, 1996; Kostenis et al., *Biochemistry* 36:1487–1495, 1997, however other regions on $G\alpha$ also are involved in receptor contact. In addition, portions of the $G\beta\gamma$ dimer have been implicated in GPCR binding. See Onrust et al., *Science* 275:381–384, 1997; Lichtarge et al., *Proc. Natl. Acad. Sci. USA* 93:7507–7611, 1996; Mazzoni and Hamm, *J. Biol. Chem.* 271:30034–30040, 1996; Bae et al., *J. Biol. Chem.* 272: 32071–32077, 1997. The carboxyl terminal amino acid regions of $G\alpha$ proteins (and other GPCR binding regions of the heterotrimeric G protein) not only provide the molecular basis of receptor-mediated activation of G proteins, but they also play an important role in determining the fidelity of receptor activation. Conklin et al., *Nature* 363:274–276, 1993; Conklin et al., *Mol. Pharmacol.* 50:885–890, 1996.

The G-protein complex thus serves a complex role, as an intermediate that relays the signal from receptor to one or more specific effectors, and as a clock that controls the duration of the signal. Hamm and Gilchrist, *Curr. Opin. Cell Biol.* 8:189–196, 1996. Multiple receptors can activate a single G protein subtype, and in some cases a single receptor can activate more than one G protein, thereby mediating multiple intracellular signals. In other cases, however, interaction of a receptor with a G protein is regulated in a highly selective manner such that only a particular heterotrimer is bound.

Because G proteins and their receptors influence a large number of intracellular signals mediated by a large number of different chemical ligands, considerable potential for modulation of disease pathology exists. Many medically significant biological processes are influenced by G protein signal transduction pathways and their downstream effector molecules. See Holler et al., *Cell. Mol. Life Sci.* 340: 1012–20, 1999. Therefore, G protein-coupled receptors and their ligands are the target for many pharmaceutical products and are the focus of intense drug discovery efforts. Over the past 15 years, nearly 350 therapeutic agents targeting GPCRs have been successfully introduced into the market. Because of the ubiquitous nature of G protein-mediated signaling systems, and their influence on a great number of pathologic states, it is highly desirable to find new methods of modulating these systems.

Most currently available drugs affecting GPCRs act by antagonizing the binding between a G protein-coupled receptor and its extracellular ligand(s). On the other hand, receptor subtype-selective drugs have been difficult to obtain. A drawback to the classical approach of designing drugs to interfere with ligand binding has been that conventional antagonists are ineffective for some GPCRs such as proteinase activated receptors (PAR) due to the unique mechanism of enzymatic cleavage of the receptor and generation of a tethered ligand. In other cases, intrinsic or constitutive activity of receptors leads to pathology directly, thus rendering antagonism of ligand binding moot. For these reasons, alternative targets for blocking the consequences of GPCR activation and signaling are highly desirable.

One potential alternative target for inhibition by new pharmaceuticals has been the receptor-G protein interface on the interior of the plasma membrane. Konig et al., *Proc. Natl. Acad. Sci. USA* 86:6878–82, 1989; Acharya et al., *J. Biol. Chem.* 272:651924, 1997; Verrall et al., *J. Biol. Chem.* 272:6898–902, 1997. The carboxyl terminus of $G\alpha$ and other regions of the G protein heterotrimer conform to a binding site at the cytoplasmic face of the receptor. Sondek et al., *Nature* 372:276–9, 1994; Lambright et al., *Nature* 369:621–8, 1994; Lambright et al., *Nature* 379:311–9, 1996; Sondek et al., *Nature* 379:369–74, 1996; Wall et al., *Science* 269:1405–12, 1996; Mixon et al., *Science* 270:954–960, 1995. Peptides corresponding to these binding regions or mimicking these regions, can block receptor signaling or stabilize the active agonist-bound conformation of the receptor. Hamm et al., *Science* 241:832–5, 1988; Gilchrist et al., *J. Biol. Chem.* 273:14912–9, 1998. For example, in the case of rhodopsin, the rod photoreceptor, the $G\alpha$ C-terminal peptide, $G\alpha$ 340–350, stabilizes the receptor in its active metarhodopsin II conformation. Hamm et al., *Science* 241-832-5, 1988; Osawa and Weiss, *J. Biol. Chem.* 270:31052–31058, 1995. Similarly, two carboxyl terminal peptides from Gαs (354–372 and 384–394), but not the corresponding peptides from Gαi$_2$, evoke high affinity agonist binding to β$_2$-adrenergic receptors and inhibit their ability to activate Gαs and adenylyl cyclase. Rasenick et al., *J. Biol. Chem.* 269:21519–21525, 1994.

In general, GPCRs require agonist binding for activation. However, modifications to the receptor amino acid sequence can stabilize the active state conformation without the requirement for a ligand. Stabilization by such ligand-independent means is termed "constitutive receptor activation." Constitutive (or agonist-independent) signaling activity in mutant receptors has been well documented, but only a few GPCRs have been shown to exhibit agonist-independent activity in the wild type (or native) form. For example, native dopamine D1B and prostaglandin EP1b receptors possess constitutive activity (Tiberi and Caron, J. Biol. Chem. 269:27925–27931, 1994; Hasegawa et al., J. Biol. Chem. 271:1857–1860, 1996). A number of GPCRs, for example, receptors for thyroid-stimulating hormone (Vassart et al., Ann. N.Y. Acad. Sci. 766:23–30, 1995), causing disease in humans have been found to be mutated to exhibit agonist-independent activity. Experimentally, several single amino acid mutations have produced agonist independent activity. β2 and α2 adrenergic receptors, for example, mutated at single sites in the third cytoplasmic loop show constitutive activity (Ren et al., J. Biol. Chem. 268:16483–16487, 1993; Samama et al., Mol. Pharmacol. 45:390–394, 1994). In some cases, a large deletion mutation in the carboxy tail or in the intracellular loops of GPCRs has led to constitutive activity. For example, in the thyrotropin releasing hormone receptor a truncation deletion of the carboxyl terminus Nussenzveig et al., J. Biol. Chem. 268: 2389–2392, 1993; Matus-Leibovitch et al., J. Biol. Chem. 270:1041–1047, 1995 or a smaller deletion in the second extracellular loop of the thrombin receptor (Nanevicz et al., J. Biol. Chem. 270:21619–21625, 1995) renders the receptor constitutively active.

These finding have led to a modification of traditional receptor theory (Samama et al., J. Biol. Chem. 268:4625–4636, 1993). It is now thought that receptors can exist in at least two conformations, an inactive conformation (R) and an activated conformation (R*), and that an equilibrium exists between these two states that markedly favors R over R* in the majority of receptors. It has been proposed that in some native receptors and in the mutants described above, there is a shift in equilibrium in the absence of agonist that allows a sufficient number of receptors to be in the active R* state to initiate signaling.

Negative antagonism is demonstrated when a drug binds to a receptor that exhibits constitutive activity and reduces this activity. Negative antagonists appear to act by constraining receptors in an inactive state (Samama et al., Mol. Pharmacol. 45:390–394, 1994). Although first described in other receptor systems (Schutz and Freissmuth, J. Biol. Chem. 267:8200–8206, 1992), negative antagonism has been shown to occur with GPCRs such as opioid (Costa and Herz, Proc. Natl. Acad. Sci. USA 86:7321–7325, 1989; Costa et al., Mol. Pharmacol. 41:549–560, 1992), β2-adrenergic (Samama et al., Mol. Pharmacol. 45:390–394, 1994; Pei et al., Proc. Natl. Acad. Sci. USA 91:2699–2702, 1994; Chidiac et al., Mol. Pharmacol. 45:490–499, 1994), serotonin type 2C (Barker et al., J. Biol. Chem. 269:11687–11690, 1994), bradykinin (Leeb-Lundberg et al., J. Biol. Chem. 269:25970–25973, 1994), and D1B dopamine (Tiberi and Caron, J. Biol. Chem. 269:27925–27931, 1994) receptors. That being stated, the concept of a constitutively active receptors offer insights which explain pathophysiologic conditions. For example, a constitutively active receptor in a disease process such as hypertension may no longer be under the influence of the sympathetic nervous system. In hypertension, a constitutively active GPCR may be expressed in any number of areas including the brain, kidneys or peripheral blood vessels. A newly recognized class of drugs (negative antagonists or inverse agonists) which reduce undesirable constitutive activity can act as important new therapeutic agents. Thus, a technology for identifying negative antagonists of both native and mutated GPCRs has important predictable as well as not yet realized pharmaceutical applications. Furthermore, because constitutively active GPCRs are tumorigenic, the identification of negative antagonists for these GPCRs can lead to the development of anti-tumor and/or anti-cell proliferation drugs.

Mutagenesis of this same region of Gα has identified several specific amino acid residues in this binding region crucial for Gα activation by rhodopsin. Martin et al., *J. Biol. Chem.* 271:361–6, 1996. Substitution of three to five carboxyl-terminal amino acids from Gαq with corresponding residues from Gαi allowed receptors which signal exclusively through Gαi subunits to activate the chimeric α subunits and stimulate the Gαq effector, phospholipase C β. Conklin et al., i Nature 363:274–276, 1993; Conklin et al., *Mol. Pharmacol.* 50:885–890, 1996. All of these studies suggest that Gα carboxyl peptide sequences are responsible for the specificity of the signaling responses of the individual G proteins. There are 16 unique Gα subunits (Gαi$_1$, Gαi$_2$, Gαi$_3$, GαO$_1$, GαO$_2$, GαZ, Gαt, Gαq, Gα11, Gα14, Gα5, Gα12, Gα13, Gα15/16, GαIF and Gαgust) thought to mediate specific interaction with different GPCRs, several hundred of which have been cloned. Thus, peptides corresponding to G protein regions which bind the GPCR could be used as competitive inhibitors of receptor-G protein interactions. Hamm et al., *Science* 241-832-5, 1988; Gilchrist et al., *J. Biol. Chem.* 273-14912-9, 1998. Drug discovery approaches which take advantage of this opportunity, however, are not available. Jones et al., Expert Opin. Ther. Patents 9(12): 1641, 1999.

An important aspect of the modern drug discovery process is the identification of potent lead compounds for use in modern high throughput screening assays. One of the major challenges confronting companies using high throughput screening is the difficulty of identifying useful lead compounds from very large combinatorial libraries. When literally hundreds of thousands of compounds are screened, characterizing the compounds which test positive (including false positives) is an expensive and time-consuming process. Hence, a method which can identify potent lead compounds and reduce the number of false positives in the screening process would be very desirable.

SUMMARY OF THE INVENTION

This invention provides a method of identifying a G protein coupled receptor signaling inhibitor, which comprises (a) providing a peptide library based on a native G protein coupled receptor binding peptide; (b) screening said peptide library for high affinity binding to said G protein coupled receptor; (c) selecting a member of said peptide library having binding to said G protein coupled receptor of higher affinity than that of the native peptide; (d) providing a library of candidate compounds to screen for binding to said G protein coupled receptor; (e) screening said library of candidate compounds for high affinity binding to said G protein coupled receptor in competition with a member of said peptide library selected in step (c); and (f) identifying a member of said library of candidate compounds having binding to said G protein coupled receptor of equal or higher affinity than that of the peptide selected in step (c).

The invention also provides, in a further embodiment, an enzyme-linked immunosorbant assay which comprises the steps of (a) immobilizing a G protein coupled receptor onto a solid support; (b) providing a protein-peptide fusion protein display library; (c) incubating members of said protein-peptide fusion protein display library with said immobilized G protein coupled receptor in the presence of said G protein coupled receptor binding peptide under conditions such that members of protein-peptide fusion protein display library having a binding affinity for said G protein coupled receptor at least as high as said G protein coupled receptor binding peptide bind to said immobilized G protein coupled receptor; (d) removing unbound members of said protein-peptide fusion protein display library; (e) incubating said bound protein-peptide fusion protein display library with antibodies which specifically recognize the protein portion of said protein-peptide fusion protein display library members under conditions such that said antibodies specifically bind to said protein-peptide fusion protein display library members; (f) removing unbound antibodies; and (g) detecting said bound antibodies.

In yet a further embodiment, the invention provides a method of identifying a G protein coupled receptor signaling inhibiting peptide, which comprises (a) providing a peptide library based on a native G protein coupled receptor binding peptide; (b) screening said peptide library for high affinity binding to said G protein coupled receptor; and (c) selecting a member of said peptide library having binding to said G protein coupled receptor of higher affinity than that of the native peptide.

In yet a further embodiment, the invention provides a method of identifying a G protein coupled receptor signaling inhibitor compound, which comprises (a) providing a library of candidate compounds to screen for binding to said G protein coupled receptor; (b) providing a high affinity G protein coupled receptor binding peptide; (c) screening said library of candidate compounds for high affinity binding to said G protein coupled receptor in competition with said high affinity G protein coupled receptor binding peptide; and (d) identifying a member of said library of candidate compounds having binding to said G protein coupled receptor of equal or higher affinity than that of the peptides of step (b).

In yet a further embodiment, the invention provides a method of inhibiting G protein coupled receptor signaling which comprises contacting a compound with said G protein coupled receptor which interferes with binding of said G protein coupled receptor to its cognate G proteins.

The invention provides, in yet a further embodiment, a compound selected from the group consisting of SEQ ID NOS:2, 4, 6, 8, 10, 12, 13, 15, 17, 21, 23, 25–27, 30, 32, 34, 36, 38, 40, 45–85, 94–111, 125–150, 160–164, 175–178 and 183–264.

In yet a further embodiment, the invention provides a method for providing a therapeutic G protein coupled receptor signaling modifier peptide to a mammal which comprises administering to said mammal an expression construct which expresses a peptide according to SEQ ID NOS:2, 4, 6, 8, 10, 12, 13, 15, 17, 21, 23, 25–27, 30, 32, 34, 36, 38, 40, 45–85, 94–111, 125–150, 160–164, 175–178 and 183–264.

BRIEF DESCRIPTION OF THE DRAWINGS

FIG. 15A presents fluorescence ([Ca$^{++}$]; level) increase 30 seconds after thrombin addition. FIG. 15B shows the kinetics of [Ca$^{++}$] fluorescence changes after cell stimulation with thrombin.

DETAILED DESCRIPTION OF THE PREFERRED EMBODIMENTS

Figure 1:
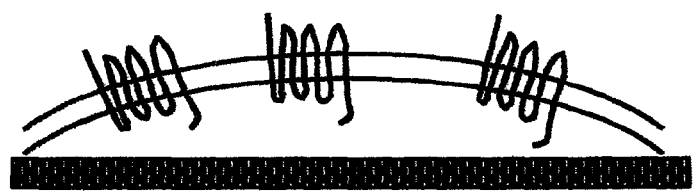
FIG. 1 is a schematic diagram showing the basis for the affinity screening method used to separate and identify GPCR binding peptides.
Figure 1:
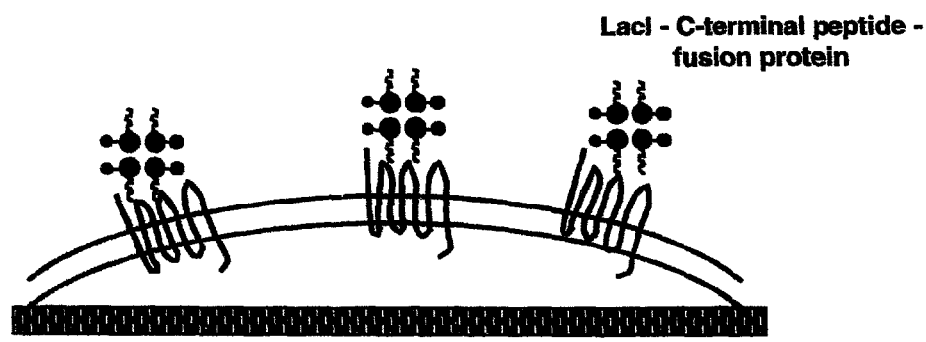
Figure 1:
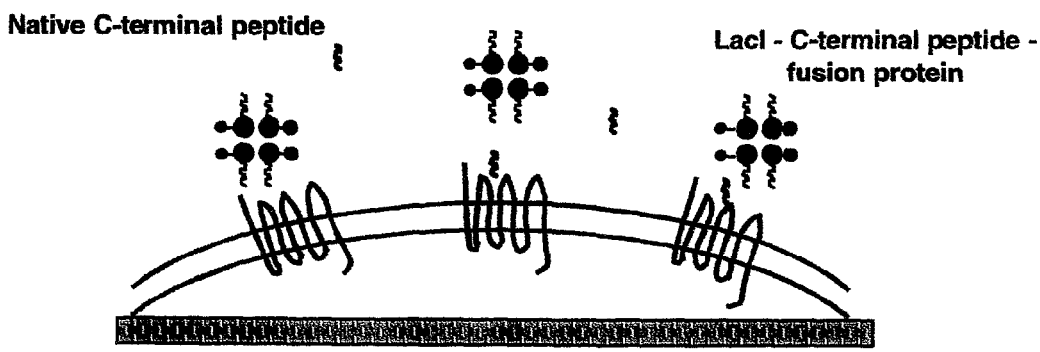

The present invention involves a method of identifying compounds which can interfere with binding at the interface between a G protein-coupled receptor (GPCR) and its cognate G proteins. These compounds inhibit G protein-mediated signaling and thus can be used as pharmaceuticals, as lead compounds for identification of potential useful drugs, and as components of assays which identify drug candidates. Methods for screening and drug identification use peptides that mimic the structure of the GPCR binding regions of G proteins and are able to inhibit receptor-G protein interactions specifically and with high affinity. These high affinity peptides can be delivered into cells in the context of an expression construct to act as blockers of specific receptor-mediated cellular responses in vitro and in vivo or can be administered directly to a patient. The peptides also form the basis of a screening, identification and selection process to provide traditional pharmaceutical compounds. In particular, the invention allows one to identify high affinity analog peptides that block the receptor-G protein interface for a particular G protein and to use these high affinity analogs in a high throughput screen to identify other peptides or small molecules that likewise specifically antagonize GPCR signaling for a G protein or class of G proteins.

Small molecules can be used in an analogous high throughput screening process to identify further compounds. "Small molecule" denotes any non-peptide organic compound which binds or interferes with binding to the interfacial region of a GPCR or is a candidate for such action. These peptides or small molecules directed at the receptor-G protein interface can be designed using the inventive method to inhibit biological processes that employ signaling through a GPCR. This approach is useful in targeting G protein-GPCR interactions for which there are no available antagonist ligands, orphan receptors the ligands of which are not known, mutant constitutively activated receptors, antibody-crosslinked irreversibly activated receptors such as TSH receptors in Graves Disease, and proteinase activated receptors (PAR). It works equally well, however, with any GPCR-G protein interaction and more broadly, with receptor-protein interactions in general.

Because the method is useful for identifying high affinity compounds that can antagonize virtually any GPCR, the approach is useful in identifying compounds which can prevent, ameliorate or correct dysfunctions or diseases in which a specific class of G proteins is relevant. Conditions and disease states for which this method is useful include, but are not limited to: stroke; myocardial infarction; restenosis; atherosclerosis; hypotension; hypertension; angina pectoris; acute heart failure; cardiomyocyte apoptosis; cancers; infections such as bacterial, fungal, protozoan and viral infections, and particularly infections caused by HIV-1 or HIV-2; septic shock; pain; chronic allergic disorders; asthma; inflammatory bowel disease; osteoporosis; rheumatoid arthritis; Graves disease; post-operative ileus; urinary retention; testotoxicosis; ulcers; obesity; benign prostatic hypertrophy; and psychotic and neurological disorders including anxiety, epilepsy, schizophrenia, manic depression, Parkinson's disease, Alzheimer's disease, delirium, dementia, drug addiction, anorexia, bulimia, mood disorders and sleep disorders; smoking cessation and any other disease or condition that can be treated by G protein coupled receptor inhibition. Treatment of this diverse set of disorders is possible because the receptors to which various G proteins bind differ enough to allow the creation of a battery of analog peptides which can specifically interface with different GPCR or different classes or groups of GPCR.

With the inventive screening methods, the sequences identified in a particular screen do not bind to all receptors, but only to the particular receptor of interest. The interaction between a G protein and a GPCR is quite specific. For example, a difference in one amino acid can substantially reduce or eliminate the ability of the Gαi$_{1/2}$ peptide to bind the A1 adenosine G protein coupled receptor-G protein interface. Gilchrist et al., *J. Biol. Chem.* 273:14912–14919, 1998. Both upstream regulation of GTP/GDP exchange on G proteins and G protein-mediated effector activation may be inhibited with interfacial binding compounds. Thus, high affinity analog peptides can be designed to specifically interfere with a particular action of one GPCR. These specifically-acting peptide analogs are useful both as pharmaceutical compounds per se, and as potent lead compounds in modern high throughput screens for other peptides and small molecule binders having the same specific GPCR interaction.

High throughput screening is a recent technology that has been developed primarily within the pharmaceutical industry. It has emerged in response to the profusion of new biological targets and the need of the pharmaceutical industry to generate novel drugs rapidly in a changed commercial environment. Its development has been aided by the invention of new instrumentation, by new assay procedures, and by the availability of databases that allow huge numbers of data points to be managed effectively. High throughput screening combined with combinatorial chemistry, rational design, and automation of laboratory procedures has led to a significantly accelerated drug discovery process compared to the traditional one-compound-at-a-time approach.

One critical aspect of the drug discovery process is the identification of potent lead compounds. A purely random selection of compounds for testing is unlikely to yield many active compounds against a given receptor. Typically, pharmaceutical companies screen 100,000 or more compounds per screen to identify approximately 100 potential lead compounds. On average, only one or two of these compounds actually produce lead compound series. Therefore, companies have been assaying larger and larger data sets in the search for useful compounds. Compound accessibility then becomes an issue: historical compound collections are limited in size and availability. In contrast, large combinatorial chemistry libraries can be synthesized on demand, but at significant technical difficulty and cost. As the library sizes expand, the difficulty becomes selecting the desired compounds from these very large combinatorial libraries. When literally hundred of thousands of compounds are screened, it makes characterizing the candidate lead compounds (artificial and real) an expensive and time-consuming process.

The multi-step approach to the drug discovery process described here provides a solution to many of these problems. One embodiment of this invention takes advantage of the properties of G protein α subunit carboxyl termini to identify peptides which act as high affinity, competitive inhibitors of G protein/GPCR interactions. The method, however, can be used with any specific protein-protein, protein-small molecule, protein-nucleic acid interaction or the like. In addition, peptides based on any region of a Gα subunit, or any region of a Gβα dimer, which is involved in GPCR binding may be used in the same way. Many such GPCR binding regions are known in the art. The identification of high affinity competitors forms a first step in a screening and selection method which overcomes many of the disadvantages of high throughput screening by providing specific, high affinity lead compounds against which to test potentially useful pharmaceuticals. Because peptides selected by this method have affinity for their binding partner up to 1,000 times higher or more than the native protein, this step is one key to successfully screening and identifying useful pharmaceutical compounds.

A subsequent step of the process involves high throughput screening of candidate peptide or small molecule pharmaceutical compounds against the high affinity lead peptides identified in the first step. Because the lead peptide compounds are potent and specific binders to the desired receptor, screening assays testing for compounds which are competitive inhibitors and thus decrease binding of the peptide (which interfere with their high-affinity binding) will facilitate identification of those candidate compounds which bind with useful affinity. The high throughput screening step of the drug discovery process is thereby greatly simplified, because the number of false positive compounds, and compounds which are identified as binders but which bind only with low affinity, is reduced or virtually eliminated. Only those compounds with a high chance of success will be identified by the screen, therefore there are many fewer compounds which need to be characterized and further studied to identify useful, specific, potent pharmaceutical compounds. In addition, the method identifies a compound through binding directly to the precise site of interest, so that the mechanism of binding and the mechanism of action of the newly identified pharmaceutical compound does not have to be discovered and confirmed later.

The identified high affinity peptides also may be used to identify GPCR inverse agonists. The high affinity peptides bind the receptor and stabilize it in an active or "R*" conformation. Screens which are used to identify potent agonists seek out compounds which can compete with this binding and also stabilize the GPCR in its R* state. Inverse agonists, on the other hand, stabilize the GPCR in an inactive or "R" state. Therefore, screens designed to detect dissociation of the high affinity peptide or a decrease in its affinity for the GPCR are used to identify inverse agonists.

Although this description provides examples relative to the interaction between a G protein coupled receptor and its cognate Gα protein, the methodology can be used to identify peptide inhibitors of most protein-protein interactions, specifically including any interaction between a GPCR and any region of a Gα or Gβγ G protein subunit. The high affinity peptides selected by this method may be used in high throughput screening to identify small molecules that can be used as modulators of a variety of specific biological process.

To produce very high affinity peptide GPCR blockers, the tertiary structure of a wild-type Gα carboxyl terminal peptide or any other GPCR binding peptide in its receptor-bound conformation may be studied, for example, using trNOESY (NMR). Dratz et al., Nature, 363:276–280, 1993. Structural data derived from these types of studies of G protein regions are combined with analysis of activity of substituted peptide analogs to define the minimal structural requirements for interaction of peptides with GPCR. The following experimental systems are examples of systems which can be used to define receptor-G protein interactions: (i) rhodopsin-transducin (Gαt) in retinal rod cells, (ii) β-adrenergic receptor-Gαs in C6 glioma cells, (iii) adenosine A1 receptor-Gαl in Chinese hamster ovary cells, (iv) GABA$_B$ receptors-Gαl in rat hippocampal CA1 pyramidal neurons, (v) muscarinic M2 receptor-Gαl in human embryonic kidney cells, and the like. Any GPCR or group of GPCR which is convenient or desired can be used to define the interaction requirements, and skilled workers are aware of many methods to understand structure-activity relationships in receptor binding of this kind. Any of these methods are contemplated for use in these methods and may substitute for the particular methods of the exemplified embodiment.

The plasmid display method provides an efficient means of identifying specific and potent peptides that can serve as competitive inhibitors of protein-protein interactions. Using the information gleaned from structure-activity studies, a library of variant peptides encoding sequences related to a GPCR-binding region, for example the Gα subunit carboxyl terminus, for each of the classes of the Gα subtypes or Gβγ can be prepared. Exemplary native sequences upon which libraries may be based include those listed in Table III, below. This library advantageously contains peptides with computer-generated random substitutions within the sequence, and allows one to test a large number of peptide sequences at one time. Preferably, peptide sequences in each library are constructed such that approximately 50% of the amino acid residues are identical to the native GPCR binding region and the remaining amino acid residues are randomly selected from any amino acid. The peptides may range in size from about 7 to about 55 amino acid residues or from about 8 to about 50 amino acids long or from about 7 to about 70 amino acid residues or longer, preferably from about 9 to about 23 amino acid residues. Undecamer peptides are most preferred. Libraries may be constructed in which about 10% to about 90% of the amino acid residues unchanged from the native sequence; however, about 30% to about 70% unchanged is preferred and about 50% is most preferred.

Alternatively, a synthetic peptide library can be based on any protein known to interact with a GPCR, using randomly created overlapping regions of the protein. The peptides may be about 7–70 amino acids long or about 8–50 amino acids long or preferably about 9 to about 23 amino acids long and most preferably about 11 amino acids long. Oligonucleotides encoding the peptides advantageously may be cloned to the 3' end of the LacI gene, with a linker sequence at the N-terminus of the peptide. The linker sequence is not mandatory for successful screening, but is generally preferred. Restriction enzyme sites may be placed at either end of the peptide coding sequence for cloning purposes. See Table I below for a schematic representation of a peptide library and an example of one peptide. Additional peptides which can be used are shown in Tables II and III, below. The oligonucleotides encoding the actual peptide sequences are synthesized with 70% of the correct base and 10% each of the remaining bases, leading to a biased peptide library with an approximately 50% chance of having the correct amino acid at any specific position along the peptide sequence. Different ratios of bases may be used to achieve the desired mutagenesis rate at any particular position in the sequence.

TABLE I

Example for Construction of a Synthetic Peptide Library.

```
                          Q   R   M   H   L      (SEQ ID NO:13)
gaggtggt nnknnknnknnk attcgtqaaaactt
    A        B
                          R   Q   Y   E   L   L
aaaagattgtggtcgtttc taa ctaagtaaagc
         C              D       E
```

(SEQ ID NO:14) n = any nucleotide base; k = guanidine or thymidine; A = restriction enzyme site; B = linker sequence; C = oligonucleotide encoding peptide sequence; D = stop codon; E = restriction enzyme site.

TABLE II

Gα Subunit Peptides and Corresponding DNA Constructs.

| Gα Subunit | Sequence | | | | | | | SEQ ID NO: |
|---|---|---|---|---|---|---|---|---|
| | | | | | | | | (SEQ ID NOS:43, 44) |
| Gt | I | K | E | N | L | K | D | C | 15 |
| | atc aag gag aac ctg aaa gac tgc | | | | | | | 16 |
| | G | L | F | | | | | |
| | ggc ctc ttc | | | | | | | |
| Gi1/2 | I | K | N | N | L | K | D | C | 17 |
| | ata aaa aat aat cta aaa gat tgt | | | | | | | 18 |
| | G | L | F | | | | | |
| | ggt ctc ttc | | | | | | | |
| GRi1/2 | N | G | I | K | C | L | F | N | 19 |
| | aac ggc atc aag tgc ctc ttc aac | | | | | | | 20 |
| | D | K | L | | | | | |
| | gac aag ctg | | | | | | | |
| Gi3 | I | K | N | N | L | K | E | C | 21 |
| | att aaa aac aac tta aag gaa tgt | | | | | | | 22 |
| | G | L | Y | | | | | |
| | gga ctt tat | | | | | | | |
| Go2 | I | A | K | N | L | R | G | C | 23 |
| | atc gcc aaa aac ctg cgg ggc tgt | | | | | | | 24 |
| | G | L | Y | | | | | |
| | gga ctc tac | | | | | | | |
| Go1 | I | A | N | N | L | R | G | C | 25 |
| | att gcc aac aac ctc cgg ggc tgc | | | | | | | 26 |
| | G | L | Y | | | | | |
| | ggc ttg tac | | | | | | | |
| Gz | I | Q | N | N | L | K | Y | I | 27 |
| | ata cag aac aat ctc aag tac att | | | | | | | 28 |
| | G | L | C | | | | | |
| | ggc ctt tgc | | | | | | | |
| G11 | L | Q | L | N | L | K | E | Y | 2 |
| | ctg cag ctg aac ctc aag gag tac | | | | | | | 29 |
| | N | L | V | | | | | |
| | aac ctg gtc | | | | | | | |
| Gq | L | Q | L | N | L | K | E | Y | 30 |
| | ctc cag ttg aac ctg aag gag tac | | | | | | | 31 |
| | N | A | V | | | | | |
| | aat gca gtc | | | | | | | |
| Golf | Q | R | M | H | L | K | Q | Y | 32 |
| | cag cgg atg cac ctc aag cag tat | | | | | | | 33 |
| | K | L | L | | | | | |
| | gag ctc ttg | | | | | | | |
| G14 | L | Q | L | N | L | R | E | F | 34 |
| | cta cag cta aac cta agg gaa ttc | | | | | | | 35 |
| | N | L | V | | | | | |
| | aac ctt gtc | | | | | | | |
| G15/16 | L | A | R | Y | L | D | E | I | 36 |
| | ctc gcc gcc tac ctg gac gag atc | | | | | | | 37 |
| | N | L | L | | | | | |
| | aac ctg ctg | | | | | | | |

TABLE II-continued

Gα Subunit Peptides and Corresponding DNA Constructs.

| Gα Subunit | Sequence | | | | | | | SEQ ID NO: |
|---|---|---|---|---|---|---|---|---|
| G12 | L | Q | E | N | L | K | D | I | 38 |
| | ctg cag gag aac ctg aag gac atc | | | | | | | 39 |
| | M | L | Q | | | | | |
| | atg ctg cag | | | | | | | |
| G13 | L | H | D | N | L | K | Q | L | 40 |
| | ctg cat gac aac ctc aag cag ctt | | | | | | | 41 |
| | M | L | Q | | | | | |
| | atg cta cag | | | | | | | |
| Gs | Q | R | M | H | L | R | Q | Y | 13 |
| | cag cgc atg cac ctt cgt cag tac | | | | | | | 42 |
| | E | L | L | | | | | |
| | gag ctg ctc | | | | | | | |

5'-gatccgccgccaccatggga- -tgaa-3'

TABLE III

Exemplary Native G Protein Sequences for Library/Minigene Construction.*

| Name | Sequence | SEQ ID NO: |
|---|---|---|
| hGt | IKENLKDCGLF | 15 |
| hGi1/2 | IKNNLKDCGLF | 17 |
| G05_DRO | IKNNLKQIGLF | 45 |
| GAF_DRO | LSENVSSMGLF | 46 |
| Gi-DRO | IKNNLKQIGLF | 45 |
| hGi3 | IKNNLKECGLY | 21 |
| hGO-1 | IANNLRGCGLY | 25 |
| hGO-2 | IAKNLRGCGLY | 47 |
| GAK_CAV | IKNNLKECGLY | 21 |
| G0_XEN | IAYNLRGCGLY | 48 |
| GA3_CAEEL | IQANLQGCGLY | 49 |
| GA2_CAEEL | IQSNLHKSGLY | 50 |
| GA1_CAEEL | LSTKLKGCGLY | 51 |
| GAK_XEN | IKSNLMECGLY | 52 |
| GA1_CAN | VQQNLKKSGIM | 53 |
| hGZ | IQNNLKYIGLC | 27 |
| hGl5 | LARYLDEINLL | 26 |
| GA2_SCHPO | LQHSLKEAGMF | 54 |
| hG12 | LQENLKDIMLQ | 38 |
| hG13 | LHDNLKQLMLQ | 40 |
| GAL_DRO | LQRNLNALMLQ | 55 |
| GA2_YST | ENTLKDSGVLQ | 56 |
| hG14 | LQLNLREFNLV | 34 |
| hG11 | LQLNLKEYNLV | 2 |
| hGQ | LQLNLKEYNAV | 30 |
| GQ_DROME | LQSNLKEYNLV | 57 |
| G11_XEN | LQHNLKEYNLV | 58 |
| Gq_SPOSC | IQENLRLCGLI | 59 |
| GA1_YST | IQQNLKKIGII | 60 |
| GA1_NEUCR | IIQRNLKQLIL | 61 |
| CryptoGba1 | LQNALRDSGIL | 62 |
| GA3_UST | LTNALKDSGIL | 63 |
| GA1_KLU | IQQNLKKSGIL | 64 |
| GA3_UST | LTNALKDSGIL | 63 |
| GA1_DIC | NLTLGEAGMIL | 64 |
| GA2_KLU | LENSLKDSGVL | 65 |
| GA2_UST | ILTNNLRDTVL | 66 |
| MGs-XL | QRMHLPQYELL | 67 |
| hGs | QRMHLRQYELL | 13 |
| hGolf | QRMHLKGYELL | 68 |
| GA1_COPCO | LQLHLRECGLL | 69 |
| GA1_SOL | RRRNLFEAGLL | 70 |
| GA2_SB | RRRNLLEAGLL | 71 |
| GA1_SB | RRRNPLEAGLL | 72 |
| GA1_UST | IQVNLRDCGLL | 73 |
| GA4_UST | RENLKLTGLVG | 74 |
| GA1_ORYSA | DESMRRSREGT | 75 |
| GQ1_DROME | MQNALKEFNLG | 76 |

TABLE III-continued

Exemplary Native G Protein Sequences for Library/Minigene Construction.*

| Name | Sequence | SEQ ID NO: |
|---|---|---|
| GA2_DIC | TQCVMKAGLYS | 77 |
| GS-SCH | LQHSLKEAGMF | 54 |
| GA-SAC | ENTLKDSGVLQ | 56 |
| GA1-CE | IISASLKMVGV | 78 |
| GA2-CE | NENLRSAGLHE | 79 |
| GA3-CE | RLIRYANNIPV | 80 |
| GA4-CE | LSTKLKGCGLY | 51 |
| GA5-CE | IAKNLKSMGLC | 81 |
| GA6-CE | IGRNLRGTGME | 82 |
| GA7-CE | IQHTMQKVGIQ | 83 |
| GA8-CE | IQKNLQKAGMM | 84 |
| GA5-DIC | LKNIFNTIINY | 85 |

*For production of minigene constructs each nucleotide sequence should be constructed to encode the amino acids MG at the N-terminus of the peptide by using 5'-gatccgccgccaccatggga-(SEQ ID NO:43) and -tgga-3'(SEQ ID NO:44).

The peptides are advantageously synthesized in a display system for convenience and efficiency of performing the binding reactions. For example, plasmid or phage display systems, as are known in the art, may be employed. While peptide display systems are preferred, any method which allows efficient contact of the peptides with a GPCR and determination of binding may be used.

A peptide display ("peptides on plasmids") library is a convenient system for use with this invention which exploits the high affinity bond between LacI and lacO. The "peptides on plasmids" display is preferred for use with this invention for two major reasons. The technique is easily set up in the laboratory. In addition, the fusion of the peptide at the carboxyl terminus of the presenting protein mimics the normal presentation for carboxyl terminal peptides during the screen. If amino terminal or interior peptides are being tested, the peptide may be cloned at the appropriate position to mimic native presentation.

The "peptides on plasmids" method for testing carboxyl terminal peptides generally works as follows. Persons of skill in the art will be able to modify these methods as needed to accommodate different conditions using this general description and the examples below as a guide. A library of peptides is created by degenerate PCR based on the native GPCR-binding peptide of interest and fused to the carboxyl terminus of LacI. The peptide library is expressed via a plasmid vector carrying the fusion gene. The plasmid also contains the Lac operon (LacO), and when E. coli transcribes and translates the LacI fusion protein, it binds back as a tetramer to the encoding plasmid through its lacO DNA binding sequence, displaying the inserted sequences of interest on the plasmid. Following transcription and translation, variant peptides encoding different sequences related to the native peptide sequence therefore are displayed as carboxyl terminal extensions of the lacI gene. Thus, a stable LacI-peptide-plasmid complex is formed which can be screened for binding to receptor. Methods described in Gates et al., J. Mol. Biol. 255:373–386, 1996, the disclosures of which are hereby incorporated by reference, are suitable. See Examples 7 and 9 for exemplary methods.

The E. coli strain used to display the peptides was ARI814, which has the following genotype: Δ(srl-recA) endA1 nupG lon-11 sulA1 hsdR17 Δ (ompT-fepC) 266 ΔclpA319::kan ΔlacI lacZU118. The strain contains the hsdR17 allele that prevents restriction of unmodified DNA introduced by transformation or transduction. The ompT-fepC deletion removes the gene encoding the OmpT protease, which digests peptides between paired basic residues, the lon-11 and clpA mutations also limit proteolysis by ATP-dependent, cytoplasmic proteases. The deletion of the lacI gene prevents expression of the wild-type lac repressor, which would compete with the fusion constructs for binding to the lacO sites on the plasmid. The lacZ mutation prevents waste of the cell's metabolic resources to make β-galactosidase in the absence of the repressor. The endA1 mutation eliminates a nuclease that has deleterious effects on affinity purification, and the recA deletion prevents multimerization of plasmids through RecA-catalyzed homologous recombination. This strain was selected for its robust growth properties and high yields of immunocompetent cells. Transformation efficiencies of $2 \times 10^{10}$ colonies per mg DNA typically were achieved. Although this strain of E. coli is preferred, those of skill in the art are aware of many alternatives which are convenient for use with the methods described. Therefore, any suitable and convenient bacterial strain known in the art is contemplated for use with this invention.

The LacI-peptide fusion protein library may be released from the bacteria by gentle enzymatic digestion of the cell wall using lysozyme. After pelleting the cell debris, the lysate then can be added directly to immobilized receptor for affinity purification or used without purification. The display library of these peptides is screened to identify those peptides which bind with high affinity to a particular GPCR. In this way, it is possible to screen for and identify high affinity peptides which bind GPCR and can interfere with activation of the pre-selected specific G protein. The library can be screened against any desired GPCR. Since the combinatorial library contains peptides based on a particular Gα or Gβγ subunit, any GPCR which binds to or mediates signaling through that subunit or class of subunits can be used. Multiple libraries, based on the carboxyl terminal sequences or other regions of different G protein subunits may be constructed for screening the same or different GPCR.

To screen the plasmid display library, a G protein coupled receptor of interest advantageously may be immobilized on microtiter plates for screening by ELISA. A plasmid preparation (bacterial lysate) then may be added to the wells. This screening procedure, involving allowing the peptides displayed on the library plasmids to bind receptor, is sometimes referred to as "panning." Sequences that bind the receptor stick to the well so that non-binding sequences can be removed by a washing step. The adherent plasmids then can be expanded and used to transform E. coli. The "panning" process generally is repeated 2 to 8 times. In general, however, 3 to 4 sequential screens are sufficient and preferred. In the later rounds of panning, parent peptide (wild type sequence) preferably is co-incubated with the plasmid preparation to bind receptors and serve as a competitive inhibitor. In this way, only high affinity sequences on the display library are captured by the immobilized receptor. The same competitive inhibition may advantageously be performed using a high affinity peptide or small molecule which has already been identified, rather than the native peptide. See FIG. 1 for a schematic diagram generally describing the "panning" procedure and Example 7 for a specific embodiment. The selection process preferably is carried out in low salt buffers because high salt concentrations destabilize the LacI-lacO complex, and could lead to peptides becoming associated with the incorrect plasmid. For the same reason, the panning buffers preferably contain lactose, which causes the LacI to bind more tightly to lacO.

The selection process of this invention allows the identification of peptide sequences with higher and higher affinity binding with each round of panning. For example, diversity in an unpanned library may look like the sequences given in Table IV, below, i.e. highly randomized. After successive rounds of selection, the selected adherent peptides would look more like those given in Table V, below.

TABLE IV

Diversity in Unpanned Gq Library.

|  |  | SEQ. ID NO. |
| --- | --- | --- |
| Native | LQLNLKEYNLV | 2 |
| clone #1 | LLLQLVEHTLV | 86 |
| clone #2 | HRLNLLEYCLV | 87 |
| clone #3 | EQWNMMNTFHNI | 88 |
| clone #4 | SQVKLQKGHLV | 89 |
| clone #5 | LRLLL*EYNLG | 90 |
| clone #6 | RRLKVNEYKLL | 91 |
| clone #7 | LQLRLREHNLV | 92 |
| clone #8 | HVLNSKEYNQV | 93 |

TABLE V

Selection in Panned Gα11 Library.

|  |  | SEQ ID NO. |
| --- | --- | --- |
| Native | LQLNLKEYNLV | 2 |
| Round 1 |  |  |
| 1 | MKLNVSESNLV | 94 |
| 2 | LQTNQKEYDMD | 95 |
| 3 | LQLNPREDKLW | 96 |
| 4 | RHLDLNACNMG | 97 |
| 5 | LR*NDIEALLV | 98 |
| 6 | LVQDRQESILV | 99 |
| Round 2 |  |  |
| 1 | LQLKHKENNLM | 100 |
| 2 | LQVNLEEYHLV | 101 |
| 3 | LQFNLNDCNLV | 102 |
| 4 | MKLKLKEDNLV | 103 |
| 5 | HQLDLLEYNLG | 104 |
| 6 | LRLDFSEKQLV | 105 |
| Round 3 |  |  |
| 1 | LQKNLKEYNMV | 106 |
| 2 | LQYNLMEDYLN | 107 |
| 3 | LQMYLRGYNLV | 108 |
| 4 | LPLNPKEYSLV | 109 |
| 5 | MNLTLKECNLV | 110 |
| 6 | LQQSLIEYNLL | 111 |

Lacl is normally a tetramer and the minimum functional DNA binding species is a dimer. Thus, the peptides are displayed multivalently on the fusion protein, leading to binding to the immobilized receptor in a cooperative fashion. This cooperative binding permits the detection of binding events of quite low intrinsic affinity. The sensitivity of the assay is an advantage in that initial hits of low affinity can be identified, but the disadvantage is that the signal in the ELISA does not necessarily correlate with the intrinsic affinity of the bound peptides.

One preferred ELISA, where signal strength is better correlated with affinity, involves fusing the sequences of interest from a population of clones in frame with the gene encoding a protein, for example maltose binding protein (MBP). Once the sequences have been transferred into the monomeric fusion protein, they can be overexpressed in *E. coli* and used as either crude lysates or purified fusion proteins for assay by an ELISA which detects the protein bound to receptor or any convenient assay. Those samples with an absorbence of at least two standard deviations above background may be considered to contain high affinity binding peptides. Any desired cut-off point may be used, however, depending on the assay parameters and the needs of the operator. The purified fusion proteins can be further tested by measuring their ability to compete for the site of binding on the receptor using native peptide, a Lacl-peptide fusion protein, or heterotrimeric G protein. Use of competitive ELISA allows one to calculate $IC_{50}$ values for the binding of individual fusion protein to the immobilized receptor.

Peptide fusion proteins can be analyzed in a competitive ELISA format using a fusion protein co-incubation to prevent the binding of lower affinity peptide fusion proteins to the GPCR. Any convenient protein which does not interfere with peptide binding may be used, including for example, glutathione-S-transferase, green fluorescent protein, or ubiquitin, however a maltose binding protein fusion protein such as MB-Gα₅340–350K341R is preferred.

Cloning the library into pJS142 creates a BspEI restriction site near the beginning of the random coding region of the library. Conveniently, digestion with BspEI and SeaI allows the purification of a 900 base pair DNA fragment that may be subcloned into pELM3, a vector that directs the MBP fusion protein to the cytoplasm, a reducing environment. Alternatively, the fragment can be cloned into pELM15, a vector which directs the MBP fusion protein to the periplasm, an oxidizing environment. pELM3 and pELM15 are simple modifications of the pMALc2 and pMALp2 vectors, respectively, available commercially (New England Biolabs). Digestion of pELM3 with AgeI and ScaI allows efficient cloning of the BspEI-ScaI fragment from the pJS142 library. Any suitable method may be used which is convenient to achieve the desired result. Modifications of these methods are well known by those of skill in the art of molecular biology and are contemplated for use here.

Proof that the high affinity peptides competitively bind to GPCR and interfere with its recognition of G protein can be obtained using a competitive binding assay in the presence of a heterotrimeric G protein. For example, if rhodopsin is the GPCR used in the screen, heterotrimeric G protein, transducin (Gt) may be used. Gt binds rhodopsin with multiple epitopes and is membrane-bound via myristoylation of the α subunit and farnesylation of the γ subunit carboxyl terminus. Poor competition of peptide analog binding by carboxyl terminal native peptide constructs and/or heterotrimeric Gt indicates high affinity binding of the peptide analogs. An analogous strategy of panning, peptide synthesis and binding studies may be employed for determining high affinity peptides that bind any GPCR, for example the Thrombin receptors (PAR1, PAR3, PAR4), dopamine receptors (D1, D2, D3, D4, D5), vasopressin receptors (V1a, V1b, V2) and histamine receptors (H1, H2, H3), using carboxyl terminal peptide libraries for any Gα subunit, for example Gαi, Gαs and Gαq. Once peptide analogs with higher binding affinities have been elucidated, they can be exploited to inhibit GPCR-G protein interaction.

The peptides selected by this method, characterized by high affinity, specific blockade of a desired GPCR-mediated signaling event, may be used as therapeutic agents such as traditional pharmaceuticals or gene therapies to treat disorders which would benefit by inhibition of GPCR or used to screen additional libraries of compounds able to compete with the high affinity peptide analogs. Focused synthesis of new small molecule libraries can provide a variety of compounds structurally related to the initial lead compound which may be screened to choose optimal structures. This multi-step approach which gives high affinity inhibitory peptides in the first step, and small molecules in a subsequent step reduces the number of artificial hits by eliminating the lower affinity small molecules that would be selected and have to be assayed in a normal high throughput screening method. In addition, it focuses the search for molecules that bind to a specific desired site on the receptor, for example, that of the G protein binding/activation site, rather than screening for binding to any site on the receptor. Other advantages of this technology are that it is simple to implement, amenable to many different classes of receptors, and capable of rapidly screening very large libraries of compounds.

Any method known in the art for selecting and synthesizing small molecule libraries for screening is contemplated for use in this invention. Small molecules to be screened are advantageously collected in the form of a combinatorial library. For example, libraries of drug-like small molecules, such as β-turn mimetic libraries and the like, may be purchased from for example ChemDiv, Pharmacopia or Combichem or synthesized and are described in Tietze and Lieb, Curr. Opin. Chem. Biol. 2:363–371, 1998; Carrell et al., Chem Biol. 2:171–183, 1995; U.S. Pat. No. 5,880,972, U.S. Pat. No. 6,087,186 and U.S. Pat. No. 6,184,223. Any of these libraries known in the art are suitable for screening, as are random libraries or individual compounds. In general, hydrophilic compounds are preferred because they are more easily soluble, more easily synthesized, and more easily compounded. Compounds having an average molecular weight of about 500 often are most useful, however, compounds outside this range, or even far outside this range also may be used. Generally, compounds having c logP scores of about 5.0 are preferred, however the methods are useful with all types of compounds. Simple filters like Lipinski's "rule of five" have predictive value and may be used to improve the quality of leads discovered by this inventive strategy by using only those small molecules which are bioavailable. See Lipinski et al., Adv. Drug Delivery Rev. 23:3–25, 1997.

Screening of the peptides or small molecules may be performed conveniently using receptors from any source. Generally, it is convenient to purify receptor from cells and reconstitute the receptor in lipid vesicles or to use membranes isolated from insect or mammalian cells that overexpress the receptor. PAR1 and rhodopsin are convenient receptors, however any suitable receptor is contemplated for use with this invention. The receptors used for screening may be purified from a natural source or purified from cells which overexpress the receptor and reconstituted in lipid vesicles. Alternatively, membranes containing the receptor may be prepared from cells which natively express the receptor, for example Sf9 cells which express PAR1, or from cells which have been genetically engineered to express the receptor, for example mammalian or insect cells overexpressing PAR1. Initially, it is advantageous to determine the binding affinity of the peptide fusion protein or high affinity peptide against which the peptides or small molecules are screened. This allows the amount of receptor and peptide MBP peptide fusion protein or small molecule in the assay to be optimized.

Generally, it is convenient to test the libraries using a one well-one compound approach to identify compounds which compete with the peptide fusion protein or high affinity peptide for binding to the receptor. A single compound per well generally is used, at about 10 nM each or at any convenient concentration depending on the affinity of the receptor for the compounds and the peptide against which they are being tested. Compounds may be pooled for testing, however this approach requires deconvalution. Compounds may be pooled in groups of about 10 to about 50 compounds per well, or more, at about 10 nM each or at any convenient concentration depending on the affinity of the receptor for the compounds being tested. Peptides desirably are screened using a pooled approach because of the layer members of peptides which are screened in the first instance. Peptides may be screened individually as well, but preferably are screened in pools of about $10^4$–$10^{12}$ peptides per well or about $10^8$–$10^{10}$ peptide per well or most preferably about $10^9$ peptides per well.

ELISA, or any other convenient assay, such as fluorescence assays or radioimmunoassay may be used to determine (1) if one or more peptides in each well reduce the amount of binding by the high affinity peptide fusion protein or high affinity peptide, or (2) if one or more peptides in each well bind to the receptor. Compounds may be tested at a series of concentrations, as well, and this generally is preferred if the affinity of the peptide or peptide fusion protein is not known. In an ELISA, wells in which the $OD_{450}$ is half or less than half than that of control wells (no tested compounds) generally are considered "positive" and may be further studied. Any suitable cut-off point may be used, however, depending on the assay components and the goals of the assay.

Screening against the high affinity peptide analogs can be performed using the desired GPCR immobilized onto microtiter wells, biochips, or any convenient assay surface. Binding assays performed in solution also are suitable. One, several, or thousands of candidate small molecule pharmaceutical compounds can be screened for binding to the receptor in the presence or absence of a high affinity peptide analog. The assays preferably are performed in the presence of a high affinity binding peptide to ensure that only those candidate compounds which can successfully compete for binding against the high-affinity binding peptide will be captured by the receptor. Alternatively, organic compounds or small molecules which have been identified by screening as competitively binding with a high affinity peptide analog may also be used as lead compounds in screening for further small molecule candidate compounds with even higher affinity. In either screening process, binding may be detected by any convenient method, for example by ELISA, fluorescence assays or radioimmunoassays.

By using a two-step protocol to identify compounds which block G protein signaling, high throughput screening of compounds and characterization of the selected compounds is significantly reduced in both time and cost, because only potent and strongly binding compounds are selected. The first step of identification of high affinity peptides which strongly compete with G proteins for their site of binding on G protein-coupled receptors insures this because the high affinity peptides are designed and tested for the particular desired binding specificity, ability to inhibit function within a cellular system and ability to inhibit functions in vivo.

Preferably, only the most strongly binding and effective peptide analogs or small molecules are used in the second or subsequent screening step. This two or multi-step protocol reduces the number of false positives and identification of compounds which bind only weakly by eliminating the lower affinity small molecules that would be detected and assayed in a conventional high throughput screening method. This method, therefore, is simple to implement, inexpensive, composed of only a few components, amenable to many different classes of receptors, and capable of rapidly screening large libraries of compounds. This method enables efficient identification of new classes of small organic peptidomimetic molecules that function as inhibitors of receptor action, for example, thrombin receptor inhibitors, dopamine receptor inhibitors, histamine receptor inhibitors, or vasopressin receptor inhibitors. These identified compounds can target a single GPCR, a class of GPCR, or block a single G protein pathway activated by GPCR.

Thorough evaluation of the selected compounds (either peptides or small molecules) for use as therapeutic agents may proceed according to any known method. Properties of the compounds, such as $pK_a$, log P, size, hydrogen bonding and polarity are useful information. They may be readily measured or calculated, for example from 2D connection tables. Association/dissociation rate constants may be determined by appropriate binding experiments. Parameters such as absorption and toxicity also may be measured, as well as in vivo confirmation of biological activity.

Pharmaceutical preparations are prepared by formulating the peptides or small molecules identified by the inventive screen according to methods well known in the art, with any suitable pharmaceutical excipient or combination of pharmaceutical excipients. Preparations may be made for administration by any route, such as intravenous, intramuscular, subcutaneous, oral, rectal, vaginal, transdermal, transmucosal, sublingual and the like, however, the intravenous route is generally preferred for peptide preparations. Any suitable vehicle may be used, for example saline or lactated Ringer's, for intravenous administration.

Dosages for treatment of GPCR-related diseases or condition will depend on many factors such as the nature of the disorder, the GPCR involved, the route of administration, factors relating to the general physical condition and health of the patient and the judgment of the treating physician. Persons of skill in the art are well aware of these factors and consider manipulation of dosage to obtain an optimum result to be routine. Generally, dosages for intravenous administration may vary between about 0.01 mg/kg and 1000 mg/kg, however, this range can be expanded depending on the patient's needs. Such an expanded range is considered within the scope of this invention.

Alternatively, peptides according to this invention may be provided to cells, in vivo or ex vivo, by delivery of an expression construct. Gene therapy can be performed in-vivo as a direct introduction of the genetic material. The in vivo gene transfer would introduce the oligonucleotides encoding the peptides to cells at the site they are found in the body, for example to skin cells on an arm, or to lung epithelial cells following inhalation of the gene transfer vector. Alternatively, ex-vivo gene transfer, the transfer of genes into viable cells that have been temporarily removed from the patient and are then returned following treatment (e.g. bone marrow cells) could also be employed.

Gene transfer vectors can be engineered to enter specific tissues or cells. Transductional targeting allows the gene transfer vectors to interact with specific cell surface receptors. Transductional targeting can also take advantage of the rate of cellular division by using gene transfer vectors that target rapidly dividing cells such as tumor cells. Transcriptional targeting recruits distinct cellular promoter and enhancer elements to influence transcription of the therapeutic gene. Transfection efficiencies are also enhanced by engineering vectors with monoclonal antibodies, carbohydrate ligands, and protein ligands that help deliver genes to specific cells.

The gene transfer vectors used to produce the high affinity peptides inside cells could be viral vectors (Retrovirus, Adenovirus, Adeno-Associated Virus, Herpes Simplex Virus, or Vaccinia Virus). As an alternative, non-viral vectors may also be used, these include such methods as injection of naked DNA, or introduction of either DNA or peptides by attachment to positively charged lipids, or cationic liposomes, electroporation or ballistic DNA Injection (limited to ex-vivo applications), as well as introduction of branched peptides.

Tet-inducible retroviral vectors for the native C-terminal sequences that co-expresses GFP driven by an internal ribosomal entry site (IRES) from encephalomyocarditis virus (p-Tet-Ti-GFP) may be used. These vectors can be modified so that they encode the high affinity peptide sequences. In addition, the high affinity peptide can be driven by a sequence allowing for spatial or temporal expression. For in vitro studies, viral supernatants may be collected from a pantropic producer line such as GP-293 (Clontech) in serum-free media. Viral supernatants may be concentrated by ultracentrifugation at 4° C. for 2 hr at 22,000 rpm, and the pellets resuspended in 1/100 the original volume in serum-free media with a titer of at least $10^8$ i.u. (Infectious units)/ml and stored at −8° C.

Murine leukemia virus (MLV) derived retroviral vectors are commonly used vehicles for stable delivery of therapeutic genes into endothelial cells. For the retrovirus studies in vivo, high affinity peptides subcloned into a replication-defective murine Moloney retrovirus vector which is Tet-inducible and co-expresses GFP driven by an internal ribosomal entry site (IRES) from encephalomyocarditis virus (pTet-GFP). These constructs may then be transiently transfected into producer line to generate cell-free titers of $10^{6-10}9$ i.u/ml. If needed, a pantropic retroviral expression system (GP-293; Clontech) which utilizes VSV-G, an envelope glycoprotein from the vesicular stomatitis virus, may be utilized to overcome low transfection efficiencies. By using this innovative cell-based gene transfer method one can obtain stable, long-term, and localized gene expression of the high affinity C-terminal peptides.

To conclusively demonstrate that the compounds identified by this method can modulate G protein signaling events implicated in disease syndromes in vivo, antagonism of selective G protein signal transduction events may be confirmed. One method of testing the ability of compounds to compete with native G protein binding involves expressing peptides that block the receptor-G protein interface in cells bearing the receptor. Plasmid constructs that encode GPCR-binding region peptides, such as carboxyl terminal peptide sequences from the various Gα subunits (see Table VI) can be used to express them in cells in vivo, ex vivo or in vitro, so that the metabolic effects of selective GPCR blockade can be studied qualitatively and quantitatively. Such studies provide proof that the binding which the compounds possess is useful in vivo to modulate selective G protein signals.

Expression of the peptides is conveniently achieved using the minigene approach by methods such as those described in Example 23, however any suitable method may be used. Any desired peptide sequence may be expressed using these methods. Those of skill in the art are well aware of alternative methods for construction, transfection and expression of protein and peptide constructs comprising the high affinity peptide analogs, and such methods are contemplated for use with them.

TABLE VI

Exemplary Sequences of C-terminal Minigene Peptides.

| Peptide Name | Sequence | SEQ ID NO: |
|---|---|---|
| Gαi | MGIKNNLKDCGLF | 112 |
| GαiR | MGNGIKCLFNDKL | 113 |
| Gαq | MGLQLNLKEYNAV | 114 |
| Gαq** | MGLQLNLKEYNTL | 115 |
| Gα12 | MGLQENLKDIMLQ | 116 |
| Gα13 | MGLHDNLKQLMLQ | 117 |

As discussed above, many receptors interact with and activate multiple G proteins. Using the minigene strategy to introduce the high affinity-binding carboxyl terminal peptides into cells, it is possible to inhibit specific G protein-coupled receptor interactions with individual G proteins, thus demonstrating the feasibility of specific G protein blockade in vivo with compounds identified by the inventive method. For those receptors which activate multiple G proteins, each of which activates a distinct set of signaling pathways mediating a specific set of responses (for example, the thrombin receptor), one pathway can be inhibited without substantially affecting the others.

To selectively antagonize G protein signal transduction events in vivo by expressing peptides that block the receptor-G protein interface, minigene plasmid vectors were designed to express the C-terminal peptide sequence of the various Gα subunits following their transfection into mammalian cells. A control minigene vector also was created, encoding the carboxyl terminus of Gαi$_{1/2}$ in random order (GαiR, see Table VI). One important element necessary for the minigene approach to block intracellular signaling pathways effectively in vivo is expression of adequate amounts of the desired peptides. Therefore, expression of the minigene should be confirmed by a convenient method of detecting mRNA, protein or both. Any convenient method known in the art can be used.

To determine the cellular efficacy of the minigene approach for expressing GPCR binding peptides, and to show the specific inhibition of one G protein pathway in response to a given receptor activation signal without affecting others, compounds advantageously may be assayed in a system designed to exhibit a measurable cellular signaling endpoint. One example of such a system is the thrombin receptor, PAR1, in endothelial cells. This receptor activates multiple G proteins. Several signaling endpoints, including transcription analysis of induced PAR1 gene expression; biochemical analysis of effector molecules including [Ca$^2$+], MAP kinase ("MAPK") activity, adenylyl cyclase activity, and inositol phosphate accumulation; as well as functional assays such as cell proliferation and endothelial permeability are available to measure specific activation or modulation of activation of different G proteins by ligand binding at this receptor. Signaling activity may be measured by any convenient method, including: measuring inositol phosphate accumulation; measuring intracellular calcium concentration levels; measuring transendothelial electrical resistance; measuring stress fiber formation; measuring ligand binding (agonist, antagonist or inverse agonist); measuring receptor expression; measuring receptor desensitization; measuring kinase activity; measuring phosphatase activity; measuring nuclear transcription factors; measuring cell migration (chemotaxis); measuring superoxide formation; measuring nitric oxide formation; measuring cell degranulation; measuring GIRK activity; measuring actin polymerization; measuring vasoconstriction; measuring cell permeability; measuring apoptosis; measuring cell differentiation; measuring membrane association of a protein that translocates upon GPCR activation, such as protein kinase C; measuring cytosolic accumulation of a protein that translocates upon GPCR activation, such as protein kinase C; measuring cytosolic accumulation of a protein that translocates upon GPCR activation, such as src; and measuring nuclear association of a protein that translocates upon GPCR activation, such as Ran. The functional effects of GαC-terminal minigenes in the mechanism of thrombin-induced cell retraction, as measured by the change in transendothelial electrical resistance (TEER) also can be used to measure G protein inhibition.

For example, thrombin-mediated PAR1 gene induction was inhibited in human microvascular endothelial cells (HMEC) expressing the Gαi minigene construct. Expression of the Gαtq minigene construct, however, affected thrombin-mediated inositol phosphate accumulation. Expression of Gαq also specifically decreased both thrombin-induced intracellular Ca$^{++}$ rise and thrombin-induced MAPK activity.

Thrombin activation of the Gαi mechanism in HMEC decreases cAMP levels increased in response to isoproterenol (which acts through Gαs). Assay for cAMP level increases in response to isoproterenol alone may be compared to increases after thrombin pre-incubation in cells expressing Gαi to show that expression of the GPCR binding peptide blocks Gαi signaling.

Recent work by Gohla et al., J. Biol. Chem. 274:17901–17907, 1999, elegantly demonstrated that thrombin receptors induce stress fiber accumulation via Gα12 in an EGF receptor-independent manner. The formation of stress fiber formation appears to be Rho dependent. Both G12 and G13 have been implicated in the Rho signaling pathway. Therefore, expression of Gα12 and Gα13 GPCR-binding peptides in HMEC were used to determine whether these peptides could block the appearance of stress fibers in response to thrombin.

The extracellular signal-regulated kinase (ERK) subfamily of mitogen-activated protein kinases (MAPKs) regulates numerous cell signaling events involved in proliferation and differentiation. This forms the basis of another assay which can determine whether GPCR binding peptides can affect a specific G protein mediated pathway. Transfection of HMEC cells with minigenes encoding GPCR binding peptides along with HA-MAPK followed by immunoprecipitation of the HA-MAPK permits measurement of the effects only on cells expressing GPCR binding peptides.

Many studies have shown that the M$_2$ muscarinic receptor (mAChR) couples exclusively to the Gi/GO family. See Dell'Acqua et al., J. Biol. Chem. 268:5676–5685, 1993; Lai et al., J. Pham. Exp. Ther. 258:938–944, 1991; Offermanns et al., Mol. Pharm. 45:890–898, 1994; Thomas et al., J. Phar. Exp. Ther. 271:1042–1050, 1994. The M$_2$ mAChR can efficiently couple to mutant Gαq** in which the last five amino acids are substituted with the corresponding residues from Gαi or GαO, suggesting that this receptor contains domains that are specifically recognized by the carboxyl terminus of Gαi/O subunits. See Liu et al., Proc. Natl. Acad. Sci. USA 92:11642–11646, 1995.

To test inhibition of G protein-coupled receptor-mediated cellular responses by carboxyl terminal Gα peptides expressed using minigene constructs, prototypical directly Gβγ activated channels (GIRK channels) regulated by a pertussis toxin-sensitive M$_2$ mAChR was chosen as the model. In this model, the importance of the Gα carboxyl terminus and the downstream effector system have been well established. See Krapivinsky et al., *J. Biol. Chem.* 270: 29059–29062, 1995; Krapivinsky et al., *J. Biol. Chem.* 273:16946–16952, 1998; Sowell et al., *Proc. Natl. Acad. Sci. USA* 94:7921–7926, 1997. Inhibition of M₂mAChR activation of inwardly rectifying potassium currents can be tested to demonstrate inhibition of a downstream functional response following agonist stimulation of GPCR on cells transiently transfected with a Gα carboxyl terminal peptide minigene or treated with a pharmaceutical compound identified by screening against high affinity Gα peptides.

GIRK channels modulate electrical activity in many excitable cells. See Breitwiese et al., *J. Membr. Biol.* 152:1–11, 1996; Jan et al., *Curr. Opin. Cell Biol.* 9:155–160, 1997; Wickman et al., *Curr. Opin. Neurobiol.* 5:278–285, 1995. Because the channel opens as a consequence of a direct interaction with Gβγ, whole cell patch clamp recording of $I_{KACh}$ can be used to demonstrate inhibition of a downstream functional response following agonist stimulation of GPCR on cells transiently transfected with a Gα carboxyl terminal peptide minigene or treated with a pharmaceutical compound identified by screening against high affinity Gα peptides. Superfusion of cells expressing GIRK1/GIRK4 with their ligand, acetylcholine (ACh), activates inwardly rectifying potassium currents.

Using well-established receptor models accepted to be indicative of in vivo cellular results, this type of data can show that the individual G proteins activated via a given GPCR have specific roles in mediating cellular events and can be modulated in a specific fashion by ligands mimicking GPCR binding regions of individual Gα subunits. In particular, for receptors such as the thrombin receptor, which activate multiple G proteins, each of which activates a distinct set of signaling pathways mediating a specific set of responses, it is possible using the inventive methods to block one pathway while leaving all the others functional. The high affinity peptide analogs identified in vitro by consecutive affinity purification and competitive binding, are capable of specifically inhibiting the downstream consequences of G protein signaling.

The assays described above clearly establish the ability of compounds identified by in vitro competitive binding studies to interfere with a particular GPCR-G protein interaction selectively, even when the GPCR regulates multiple G proteins within the cell. Moreover, the peptides compete very effectively with the native sequence. In addition, the minigene approach described above and exemplified in the examples below allows a systematic test of the roles of other G proteins such as Gα12 and Gα13, which may be involved in the mechanism of increase of endothelial permeability, and clearly demonstrates the viability of this approach to select and identify Gα subunit modulating compounds. The peptides therefore are suitable for use in treatment of any disorder or syndrome characterized by G protein signaling excess.

In another aspect, the invention relates to methods to identify the G proteins with which a specific orphan receptor is coupled, using the materials provided by the invention. For example, the described methods can be used to test any GPCR with a battery of Gα subunit peptides to determine which species of G protein(s) mediates the effects of the receptor. The methods described in Examples 15–18 are suitable. Those of skill in the art are capable of designing other assays, or variations and modifications using these assays as guides.

The following non-limiting examples are provided to illustrate certain aspects of this invention.

EXAMPLE 1

Construction of a Peptide Library.

Figure 2:
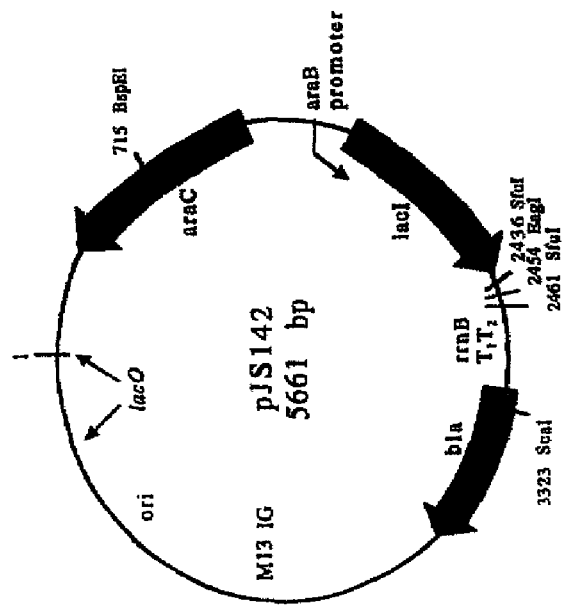
FIG. 2 is a schematic diagram of vector pJS142.

Construction of a biased peptide library has been described previously. Martin et al., *J. Biol. Chem.* 271: 361–366, 1996; Schatz et al., *Meth. Enzymol.* 267:171–191, 1996. The vector used for library construction was pJS142 (see FIG. 2). This vector had a linker sequence between the LacI and the biased undecamer peptide coding sequence, as well as restriction sites for cloning the library oligonucleotide. The oligonucleotide synthesized to encode the mutagenesis library was synthesized with 70% of the correct base and 10% of each of the other bases at each position. This mutagenesis rate leads to a biased library such that there is approximately a 50% chance that any of the 11 codons will be the appropriate amino acid and approximately a 50% chance that it will be another amino acid. In addition, a linker of four random NNK (where N denotes A, C, G or T and K denotes G or T) codons were synthesized at the 5' end of the sequence to make a total of 15 randomized codons. Using this method, a library with greater than 10⁹ independent clones per microgram of vector used in the ligation was constructed based on the carboxyl terminal sequence of Gαt (IKENLKDCGLF; SEQ ID NO:139). The nucleic acid used for creating this library was 5'-GAGGTG-GTNNKNNKNNKNNKatcaaggagaacct-gaaggactgcggcctcttcTAACTAAGTAAAGC-3', wherein N=A/C/G/T and K=G/T; SEQ ID NO:140).

EXAMPLE 2

Sequences for the Creation of Gα Subunit Peptide Libraries.

Libraries were created using the methods of Example 1 and the sequences listed below in Table VII.

TABLE VII

C-Terminal Gα Subunit Peptide Library Constructs.

| Gα Subunit | RE | Linker | Peptide Coding Region | Stop | RE | SEQ ID NO: |
|---|---|---|---|---|---|---|
| Gs | 5-GAGGTGGT | NNKNNKNNKNNK | attcgtgaaaacttaaaagattgtggtcgtttc | TAA | CTAAGTAAAGC-3' | 14 |
| G11 | 5-GAGGTGGT | NNKNNKNNKNNK | ctgcagctgaacctgaaggagtacaatctggtc | TAA | CTAAGTAAAGC-3' | 119 |
| G12 | 5-GAGGTGGT | NNKNNKNNKNNK | ctgcaggagaacctgaaggacatcatgctgcag | TAA | CTAAGTAAAGC-3' | 120 |

TABLE VII-continued

C-Terminal Gα Subunit Peptide Library Constructs.

| Gα Sub-unit | RE | Linker | Peptide Coding Region | Stop | RE | SEQ ID NO: |
|---|---|---|---|---|---|---|
| G13 | 5-GAGGTGGT | NNKNNKNNKNNK | ctgcatgacaacctcaagcagcttatgctacag | TAA | CTAAGTAAAGC-3' | 121 |
| G15 | 5-GAGGTGGT | NNKNNKNNKNNK | ctcgcccggtacctggacgagattaatctgctg | TAA | CTAAGTAAAGC-3' | 122 |
| Gz  | 5-GAGGTGGT | NNKNNKNNKNNK | atacagaacaatctcaagtacattggcctttgc | TAA | CTAAGTAAAGC-3' | 123 |

EXAMPLE 3

Isolation of Membranes from Insect Cells Expressing Thrombin Receptor.

Figure 7:
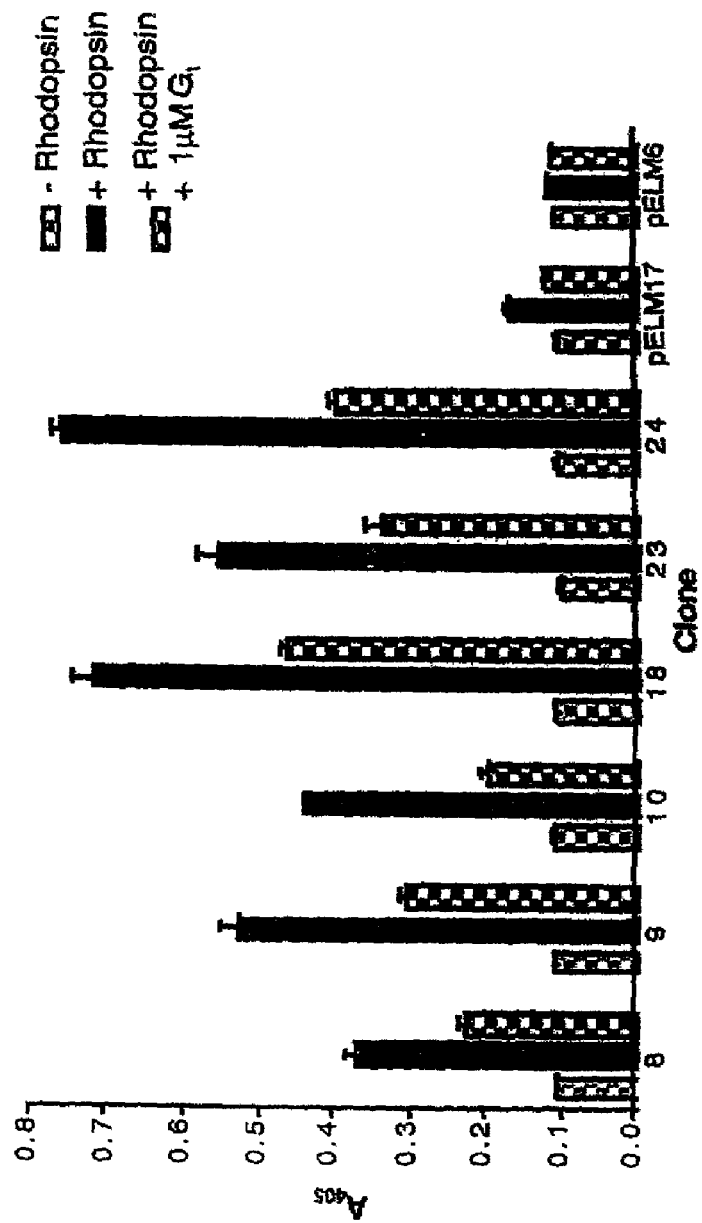
FIG. 7 is a bar graph showing competitive inhibition of high affinity peptides to rhodopsin by heterotrimeric Gt.

Sf9 cells (2×10⁸ cells) were cultured with 200 ml of Grace's insect cell culture medium (Life Technologies, Inc., Grand Island, N.Y.) containing 0.1% Pluronic F-68 (Life Technologies, Inc., Grand Island, N.Y.)), 10% fetal calf serum, and 20 µg/ml gentamicin in a 1-liter spinner flask at 27° C. for 25 hours. Sf9 cells were infected with the ThR/pBluebac recombinant virus at a multiplicity of infection of 3–5, and cultured at 27° C. for 4 days. The cells were harvested, washed with phosphate buffered saline, and then resuspended in 10 mM Tris-HCl, pH 7.4. Cells were then homogenized with a hand-held homogenizer set at low speed for 20 seconds. The broken cells were than sedimented at 17,000×g for 15 minutes. The supernatant was discarded, and the pellet resuspended in a buffer consisting of 50 mM Tris-HCl, pH 7.4 and 10% glycerol. Concentration of receptor in the membrane preparation ranged from 1–10,000 pM/mg. For screening, a final concentration of 200 µg/ml was used. The thrombin receptors were tested for their ability to bind to the native Gq-C terminal peptide using a MBP-Gq fusion protein. (FIG. 7).

EXAMPLE 4

Isolation of Membranes from Mammalian Cells Overexpressing Thrombin Receptor.

PAR1 receptor cDNA (2.1 kb insert) was obtained by polymerase chain reaction and cloned into the mammalian expression vector pBJ5. The resulting plasmid was transfected into Chinese hamster ovary cells by the calcium phosphate coprecipitation method. The PAR1 transfected cells were grown with Dulbecco's modified Eagle's medium containing 10% fetal calf serum, 100 units/mL penicillin and 100 µg/mL streptomycin. The cells were detached using PBS with 5 mM EDTA and washed twice in PBS. The pellet was either used immediately for membrane preparation or stored frozen at −20° C. Pellets were homogenized in 20 mM Tris-HCl, pH 7.5, with 5 mM EDTA and 0.5 mM PMSF, using a Dounce homogenizer (10 strokes) and sonicated for 10 seconds. Nuclear debris and intact cells were removed by centrifugation at 3000 rpm for 10 minutes. The supernatant was sedimented at 12,000×g for 30 minutes and the resulting pellet suspended in 25 mM Tris-HCl, pH 7.5, 25 mM MgCl₂, 10% sucrose, 0.5 mM PMSF, 50 µg/mL antipain, 1 µg/mL aprotinin, 40 µg/mL bestatin, 100 µg/mL chymostatin, 0.5 µg/mL leupeptin and 0.7 µg/mL pepstatin. The membranes were aliquoted and frozen at −80° C.

EXAMPLE 5

Preparation of Rod Outer Segments.

Bovine rod outer segments (rhodopsin-containing membranes) were prepared from fresh retinas under dim red light as described by Arsharky et al., J. Biol.Chem. 269:19882–19887, 1994. The retinas were placed in a beaker for dissection filled with 200 mL of 30% (w/v) sucrose in isolation buffer (90 mM KCl, 30 mM NaCl, 2 mM N$_g$Cl$_2$, 0.1 mM EDTA, 1 mM DTT, 50 µM phenylmethylsulfonyl fluoride, 10 mM MOPS, pH 7.5) on ice with constant moderate stirring of the solution during dissection. Following dissection, the retina solution was left in the dark for one hour on ice. The retina-sucrose solution was distributed into eight 50 mL tubes and sedimented at 3000×g for four minutes at 4° C. The supernatant was decanted into eight fresh centrifuge tubes and placed on ice. The volumes of the tubes were filled to 1.5 cm below top with isolation buffer, then sedimented at 17,000×g for 20 minutes ("spin 1").

The pellets were resuspended in a small volume of 30% sucrose and consolidated from eight tubes into four tubes. The tubes were filled to 1.5 cm below top with 30% sucrose, sedimented at 5000×g for four minutes at 4° C., and the supernatant decanted into four clear tubes. These tubes were filled to 1.5 cm below top with isolation buffer and sedimented at 17,000×g for 20 minutes at 4° C. ("spin 2").

A stepwise sucrose gradient was prepared in six gradient tubes using the solutions in Table VIII, below, with a sequence from top to bottom of #2, #3, 190 4.

TABLE VIII

Sucrose Gradient Solutions.

| Solution | #2 (0.84 M) | #3 (1.0 M) | #4 (1.14 M) |
|---|---|---|---|
| 42% Sucrose | 51.30 g | 61.05 g | 69.75 g |
| 1.0 M MOPS | 750 µL | 750 µL | 750 µL |
| 2.0 M KCl | 2250 µL | 2250 µL | 2250 µL |
| 3.0 M NaCl | 750 µL | 750 µL | 750 µL |
| 2.0 M MgCl₂ | 75 µL | 75 µL | 75 µL |
| Total Weight | 83.25 g | 84.75 g | 86.25 g |

The pellets from "spin 1" and "spin 2" were resuspended in isolation using 1 mL 26% sucrose buffer per tube. After making a slurry, each tube was homogenized with a 1 mL pipette and the tubes consolidated. The pellet solution was carefully laid onto the sucrose gradients and were not allowed to invade the gradient layers. The gradient tubes were subjected to 24,000×g for 30 minutes at 4° C. in a swinging bucket rotor, after which the orange layer containing the membranes was collected, being careful to avoid the pellet or the dark solution near the pellet. The membranes were distributed into six 50 mL tubes and placed on ice. The tubes then were filled to 1.5 cm below top with isolation buffer and sedimented at 17,000×g for 20 minutes at 4° C. The supernatant was discarded and the pellets resuspended in 1 mL isolation buffer containing 5 μg/mL pepstatin and 10 μg/mL E-64. This suspension was stored in a foil-wrapped 15 mL conical tube at −80° C. until needed, then thawed, homogenized in EDTA buffer (10 mM Tris pH 7.5, 1 mM EDTA 1 mM DTT) and sedimented at 30,000×g for 30 minutes. The supernatants were discarded and the pellets resuspended and sedimented again as described above. The pellets then were resuspended in urea buffer (10 mM Tris, pH 7.5 1 mM EDTA, 1 mM DTT, 7 M urea), homogenized and sedimented at 45,000 kg for 40 minutes. These pellets were resuspended and homogenized in Buffer A (200 mM NaCl, 10 mM MOPS, pH 7.5, 2 mM $MgCl_2$, 1 mM DTT, 100 μM PMSF), then sedimented at 30,000×g for 30 minutes. The pellets each were resuspended and homogenized by pipetting in 1 mL buffer A and stored at −80° C. in 100 μL aliquots in foil-covered tubes for use in assays. For screening, the receptor was added to wells at 10 μg/ml. Binding assays were performed as in Example 15.

EXAMPLE 6

Purification of PAR1 Thrombin Receptor from Insect Cells and Reconstitution of Receptors into Lipid Vesicles.

Sf9 cells (2×10$^8$ cells) were cultured in Grace's insect cell culture medium (Life Technologies, Inc., Grand Island, N.Y.) containing 0.1% Pluronic F-68 (Life Technologies), 10% fetal calf serum and 20 μg/mL gentamicin in a 1 L spinner flask at 27° C. for 25 hours. The cells were infected with ThR/pBluebac (recombinant virus) at a multiplicity of infection of 3–5 and cultured at 27° C. for four days. The cells were harvested, washed with phosphate buffered saline containing 2.7 mM EDTA and stored at −70° C. until used, the cells were resuspended in lysis buffer (2.5 mM Tris-HCl, pH 7.2, 7.5 mM NaCl, 10 mM EDTA, 1 mM phenylmethylsulfonyl fluoride, 10 mg/mL leupeptin, 10 mg/mL aprotinin, 50 mM NaF) and washed. All subsequent steps should be done on ice with cold buffers and centrifuge rotors at or below 4° C. The cells were homogenized for one minute at maximum speed and sedimented for 45 minutes at 30,000×g. The pellet was resuspended in lysis buffer and the homogenation/ washing step repeated three times. The resulting pellet was resuspended in 30 mL solubilization buffer (20 mM Tris-HCl, pH 7.4, 15 mM EGTA, 1 mM phenylmethylsulfonyl fluoride, 10 mg/mL leupeptin, 10 mg/mL aprotinin, 50 mM NaF, 0.1% (w/v) digitonin, 0.1% (w/v) Na deoxychoate) and then homogenized for one minute. The suspension was stirred for 90 minutes at 4° C. and then sedimented for 60 minutes at 30,000×g. The supernatant was loaded onto an anti-PAR1 monoclonal antibody column equilibrated with solubilization buffer containing 0.2% digitonin. After application of the supernatant, the column was washed with 10 column volumes of 10 mM Tris-HCl buffer, pH 7.4, containing 0.2% (w/v) Na dodecyl maltoside. The receptor was eluted using 10 mM triethylamine, pH 11.8. The eluted fractions were neutralized immediately using 1 M HEPES, pH 6.4. The pooled fractions were dialyzed against 50 mM HEPES buffer, pH 7.4, containing 50% (v/v) glycerol, 0.1 M NaCl and 0.2% (w/v) Na dodecyl maltoside. Aliquots were stored at −80° C.

For preparation of lipid vesicles, 200 μL phosphatidylserine (50 mg/mL in $CHCl_3$; Matreya) was dried in a rotary evaporator for 30 minutes or using a stream of dry $N_2$. After addition of 200 μL buffer A (50 mM HEPES, 100 mM NaCl, 0.2% (w/v) Na dodecylmaltoside), the tube was sealed under an $N_2$ atmosphere and sonicated in a bath sonicator for 30 minutes. Reconstitution of receptors into lipid vesicles was performed the same day, using purified receptor prepared as in Example 5. Purified receptor stocks (200 μg/mL) were thawed on ice and 50 μL was incubated for 20 minutes at 4° C. with the appropriate agonist peptide (100 nM final concentration). In the case of thrombin receptor, the agonist is thrombin receptor agonist peptide (100 nM final concentration; CalbioChem). After addition of 80 μL sonicated lipids and 50 μL buffer A, the samples were mixed using a vortex machine and placed on ice for 10 minutes. The samples then were loaded onto a 1 mL Extracti-gel™ column which had been washed with 0.2% BSA and pre-equilibrated with 5 mL Buffer A without Na dodecylmaltoside. The reconstituted vesicles were eluted from the column with 2.5 mL HEK buffer.

Figure 3:
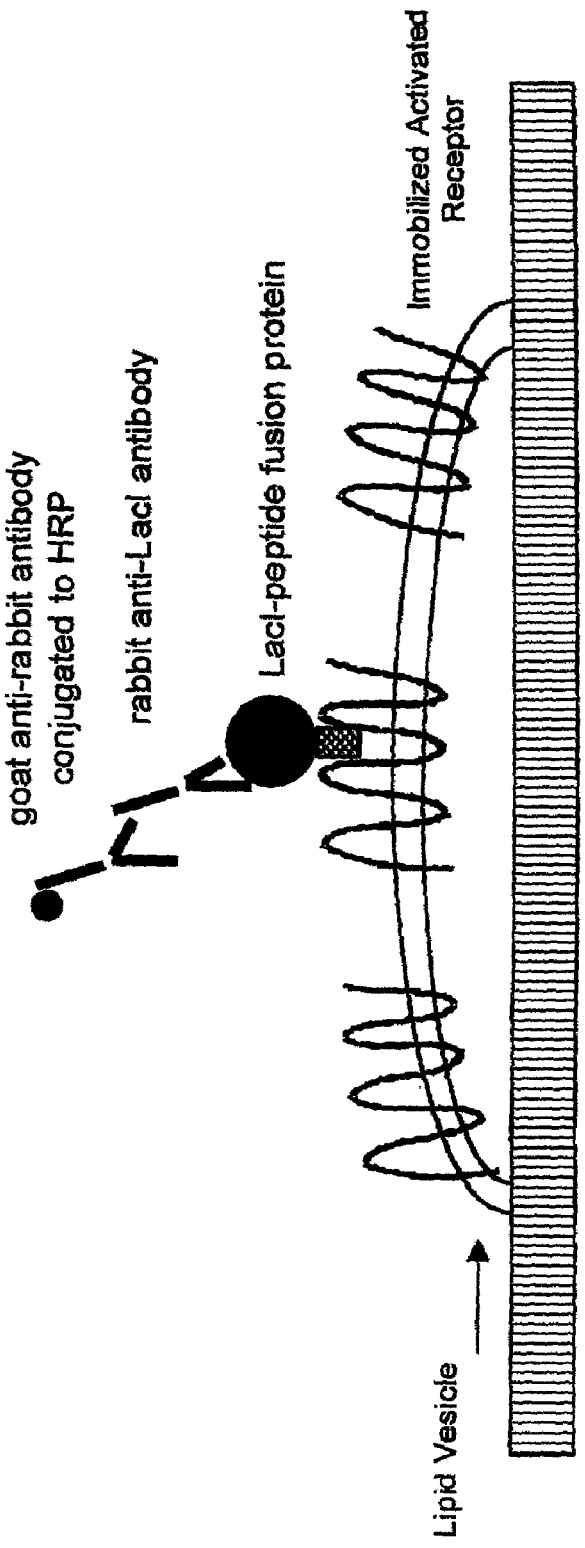
FIG. 3 is a schematic diagram showing an ELISA procedure.

Samples 100–200 μL) were collected for purity analysis by SDS-PAGE. The concentration for each batch generally was about 10–1000 μg/ml. For use, receptor was placed in microtiter plates at about 1–100 μg/ml. The purified, reconstituted thrombin receptors were tested for their ability to bind to the native Gq-C terminal peptide using a MBP-Gq fusion protein. (FIG. 3). As a control, empty vesicles were also tested for their ability to bind to the native Gq-C terminal peptide using a MBP-Gq fusion protein.

EXAMPLE 7

Identification of GPCR-Binding High Affinity Peptide Analogs (Panning).

Electrocompetent cells were produced as follows. A single colony of ARI814 bacteria was grown overnight at 37° C. in 5 ml sterile SOP (20 g/L Bacto-tryptone; 10 g/L Bacto-yeast extract; 5 g/L NaCl; 2.5 g/L anhydrous $K_2HPO_4$; 1 g/L $Mg_2SO_4.7H_2O$). One milliliter of this overnight growth was added to 500 ml SOP and the bacteria allowed to grow with the $OD_{600}$ read 0.6–0.8. All further washing steps were done in the cold. The cells were placed in an ice-water bath for at least 15 minutes, then subjected to centrifugation at 4000×g for 15 minutes at 4° C. followed by resuspension in 500 ml 10% glycerol. After sitting on ice for 30 minutes, the cells were washed twice more in 500 ml and 20 ml 10% glycerol with sedimentation as above, and finally sedimented at 5000×g for 10 minutes at 4° C. and resuspended in 1 mL 10% glycerol. Cells were quick frozen using dry ice and isopropanol in 100 μL aliquots for later use.

To transfect, aliquots (40 μL) of thawed ARI814 cells were placed into each of three chilled microcentrifuge tubes. A peptide display library based on the undecamer carboxyl terminal peptide of $Gα_t$ (SEQ ID NO:126) was prepared according to Example 1. Two microliters of library plasmid were added to the tubes and mixed. For the first round of "panning," 200 μL of the plasmid library was added. For subsequent rounds, three sets of transfections were performed (adherent plasmids from wells containing receptor (+); adherent plasmids from wells containing no receptor (−); and the PRE sample which was not incubated). See below. In each round of panning, less library was used (round 2:100 μL; round 3:50 μl; round 4:10 μL). After the panning was completed, the DNA for the Lac1 fusion protein is eluted. This DNA (50 μl) is used to transfect E. Coli cells by electroporation, using cold, sterile 0.1 cm electrode gap cuvettes. The cuvettes were pulsed one time using a BioRad E. coli Pulsar set to 1.8 kV, 25 μF capacity, time constant 4–5 mseconds, with the Pulser Controller unit at 200 mΩ. Immediately, 1 mL of SOC was added and the mixture transferred to a labeled 17×100 mm polystyrene tube. The tube was shaken for one hour at 37° C. Aliquots were taken from each set to plate 100 μL undiluted to $10^{-6}$ dilution samples on LB-Amp plates. Counts of the PRE plates indicated library diversity, while comparison of the (+) and (−) plates indicated whether specific clones were being enriched by the panning procedure.

The remaining ~900 μL in the +receptor tube was added to a 1 L flask containing 200 mL LB-AMP media, pre-warmed to 37° C., and grown at 37° C., shaking until $OD_{600}$=0.5. The tube of cells then were placed in an ice water bath for at least 10 minutes, and kept chilled at or below 4° C. during the subsequent washing steps. The cells were sedimented at 5000×g for six minutes, resuspended in 100 mL WTEK buffer, sedimented at 5000×g for six minutes, resuspended in 50 mL TEK buffer, resedimented at 5000×g for six minutes and resuspended in 4 mL HEK buffer. The cells were divided into the cryovials and stored at −70° C. One tube was used for the next round of panning and the other saved as a backup.

The panning process is illustrated in FIG. 1. For screening of the library by "panning," rhodopsin receptors prepared according to Example 5 were immobilized directly on Immulon 4 (Dynatech) microtiter wells (0.1–1 μg of protein per well) in cold 35 MM HEPES, pH 7.5, containing 0.1 mM EDTA, 50 mM KCl and 1 mM dithiothrietol (HEK/DTT). After shaking for one hour at 4° C., unbound membrane fragments were washed away with HEK/DTT. The wells were blocked with 100 μL 2% BSA in HEKL (35 mM HEPES; 0.1 mM EDTA; 50 mM KCl; 0.2 M α-lactose; pH 7.5, with 1 mM DTT). For rounds 1 and 2, BSA was used for blocking; in later rounds 1% nonfat dry milk was used. For the first round of panning, about 24 wells of a 96-well plate were used. In subsequent rounds, 8 wells with receptor and 8 wells without receptor were prepared.

The Gt library was thawed (2 mL aliquot) and mixed with 6 mL lysis buffer on ice. Lysis buffer contains 4.25 mL HE (25 MM HEPES: 0.1 mM EDTA; pH 7.5); 1 mL 50% glycerol; 750 μL 10 mg/mL protease-free BSA in HE; 10 μL 0.5M DTT; and 6.25 μL 0.2M PMSF. Freshly prepared lysozyme solution (150 μL 10 mg/mL lysozyme in cold HE) was added and the tube was gently inverted several times and incubated on ice for no more than two minutes. The extent of lysis is evidenced by an increase in viscosity that can be observed by noting the slow migration of bubbles to the top of the tube after mixing. Lysis was terminated by mixing in 2 mL 20% lactose and 250 μL 2M KCl. The tube was centrifuged immediately at 13,000×g for 15 minutes at 4° C. and the supernatant transferred to a new tube. A small aliquot of 0.1% (the PRE sample) was saved in a separate, labeled tube. The blocked rhodopsin receptor-coated plate was rinsed four times with HEKL/1% BSA and exposed to room light for less than five minutes on ice to activate the rhodopsin for light-activated rhodopsin (Table IX), or left in the dark for dark-adapted (inactive) rhodopsin (Table X). Immediately thereafter, the crude bacterial lysate from the peptide library (200 μL) was added to each well and allowed to shake gently for one hour at 4° C. For round 2, this same procedure was followed. In round 3, the amount of lysate used was reduced to 100 μL. In subsequent rounds, the lysate was diluted 1:10 in HEKL/BSA. In all rounds, 5–10 μL 200 μM native peptide was added to the wells to chase off peptides that were bound with lower affinity.

After incubation with the bacterial lysate, the wells were washed four times into cold HEKL/1% BSA. Sonicated salmon sperm DNA (200 μL 0.1 mg/mL in HEKL/1% BSA was added to each well and shaken gently for 30 minutes at 4° C. The plates were washed four times with cold HEKL and twice with cold HEK, then eluted by adding 50 μL/well 1 mM IPTG/0.2 M KCl in HE with vigorous shaking at room temperature for 30 minutes. The eluants from each group of wells (+ or − receptor) were combined in one or more microcentrifuge tubes as necessary. The volume of the PRE sample which had been saved previously was brought up to match the volume of the eluant samples and precipitated in parallel with them. To precipitate, 1/10 volume of 5M NaCl was mixed with each of the samples, then 1 μL 20 mg/mL glycogen was mixed with the samples. An equal volume of RT isopropanol was then added and mixed thoroughly. The samples were subjected to centrifugation at 13,000×g for 15 minutes and the supernatant aspirated. The pellet was washed with 500 μL cold 80% ethanol and again subjected to centrifugation at 13,000×g for 10 minutes. The pellets of plasmid DNA were resuspended in sterile, double-distilled water, 200 μL for the PRE sample and 4 μL for the + or − receptor samples and stored at ~−20° C.

Both light-activated rhodopsin and dark-adapted rhodopsin were used to screen the library in this manner. See Tables IX and X, below. Six of the sequences obtained using light-activated rhodopsin were 100–1000 times more potent than the native sequence at binding rhodopsin and are listed in Table IX. When the Gαt library was used to pan light-activated rhodopsin, residues L344, C347 and G348 were invariant. Also, in each of the highest affinity sequences, the basic residue at position 341 (R341) was changed to a neutral residue. When the Gαt library was used to pan dark-adapted rhodopsin, the L344, C347 and G348 residues were no longer invariant (L344 present in 62.5% of sequences, C347 present in 25% of sequences, G348 present in 75% of sequences) and the residue at position 341 was usually unchanged. Thus, the conformation of the receptor in its inactive, dark-adapted state allows it to bind to a different set of peptide analogs than the light-activated receptors. In addition, it appears that in the light-activated receptor, it is the last seven amino acids of the peptide which are most important (344–350) while the first six amino acids (340–345) are more important for dark-adapted rhodopsin binding.

TABLE IX

Light-Activated Rhodopsin High Affinity Sequences.

| Clone No. | SEQ ID NO: | Sequence |
|---|---|---|
| Library Sequence | 124 | I R E N L K D C G L F |
| 8 | 125 | L L E N L R D C G M F |
| 9 | 126 | I Q G V L K D C G L L |
| 10 | 127 | I C E N L K E C G L F |
| 18 | 128 | M L E N L K D C G L F |
| 23 | 129 | V L E D L K S C G L F |
| 24 | 130 | M L K N L K D C G M F |
| 3 | 131 | L L D N I K D C G L F |
| 4 | 132 | I L T K L T D C G L F |
| 6 | 133 | L R E S L K Q C G L F |
| 11 | 134 | I H A S L R D C G L F |
| 13 | 135 | I R G S L K D C G L F |
| 14 | 136 | I F L N L K D C G L F |
| 15/28 | 137 | I R E N L E D C G L F |
| 16 | 138 | I I D N L K D C G L F |
| 17 | 139 | M R E S L K C C L F |
| 19 | 140 | I R E T L K D C G L L |
| 26 | 141 | I L A D V I D C G L F |
| 27 | 142 | M C E S L K F C G L F |

TABLE X

Dark-Adapted Rhodopsin High Affinity Sequences.

| Clone No. | SEQ ID NO: | Sequence |
|---|---|---|
| Library Sequence | 124 | I R E N L K D C G L F |
| 2 | 143 | I R E K W K D L A L F |
| 3 | 144 | V R D N L K N C F L F |
| 7 | 145 | I G E Q I E D C G P F |
| 17 | 146 | I R N N L K R Y C M F |
| 21 | 147 | I R E N L K D L G L V |
| 26 | 148 | I R E N F K Y L G L W |
| 33/37 | 149 | S L E I L K D W G L F |
| 41 | 150 | I R G T L K G W G L F |

EXAMPLE 8

Screens of PAR1 with a Gq Peptide Library.

The methods of Example 7 were used to screen different sources of PAR1 receptor using the Gq library. Purified PAR1, reconstituted in lipid vesicles (Example 6), membranes prepared from Sf9 insect cells expressing PAR1 (Example 2) and membranes prepared from mammalian cells overexpressing PAR1 were used. The results of the screens are presented in Tables XI, XII and XIII, respectively. The ed as the competitor was LQLNLKEYNLV (SEQ ID NO:2).

TABLE XI

Reconstituted Purified Recombinant PAR1 Receptor; Screening Results

| Clone | SEQ ID NO: | LQLNLKEYNLV | SEQ ID NO: 2 |
|---|---|---|---|
| R2-16 | *SWV | 151 | LQFNLNDCNLV | 102 |
| R2-17 | FVNC | 152 | LQRNKKQYNLG | 160 |
| R2-18 | EVRR | 153 | MKLKLKEDNLV | 103 |
| R2-20 | *RVQ | 154 | HQLDLLEYNLG | 104 |
| R2-21 | RLTR | 155 | LQLRYKCYNLV | 161 |
| R3-37 | SR*K | 156 | LQQSLIEYNLL | 111 |
| R3-38 | MTHS | 157 | VHVKLKEYNLV | 162 |
| R3-44 | SGPQ | 158 | LQLNVKEYNLV | 163 |
| R3-46 | ML*N | 159 | LRIYLKGYNLV | 164 |

TABLE XII

PAR1 Receptor Sf9 Insect Cell Membranes; Screening Results.

| Clone | SEQ ID NO: | LQLNLKEYNLV | SEQ ID NO: 2 |
|---|---|---|---|
| S1-13 | S*IR | 165 | MKLNVSESNLV | 94 |
| S1-18 | RWIV | 166 | LQLNLKVYNLV | 175 |
| S1-23 | G*GH | 167 | LELNLKVYNLF | 176 |
| S2-26 | RSEV | 168 | LQLKHKENNLM | 100 |
| S2-30 | CEPG | 169 | LHLNMAEVSLV | 177 |
| S2-36 | HQMA | 170 | LQVNLEEYHLV | 101 |
| S3-6 | VPSP | 171 | LQKNLKEYNMV | 106 |
| S3-8 | QMPN | 172 | LQMYLRGYNLV | 108 |
| S3-10 | MWPS | 173 | LKRYLKESNLV | 178 |
| S3-15 | C*VE | 174 | MNLTLKECNLV | 110 |

TABLE XIII

Mammalian (CHO) Cells Overexpressing PAR1; Screening Results.

| Clone | SEQ ID NO: | LQLNLKEYNLV | SEQ ID NO: 2 |
|---|---|---|---|
| C4-5 | PRQL | 179 | LQLKRGEYILV | 183 |
| C4-19 | VRPS | 3 | LQLNRNEYYLV | 3 |
| C5-10 | SRHT | 11 | LRLNGKELNLV | 12 |
| C5-12 | FFWV | 180 | CSLKLKAYNLV | 184 |
| C4-16 | ORDT | 181 | LQMNHNEYNLV | 185 |
| C7-3 | NFRN | 182 | PQLNLNAYNLV | 186 |
| C7-10 | LPQM | 9 | QRLNVGEYNLV | 10 |
| C7-13 | LSTN | 7 | LHLNLKEYNLV | 8 |
| C7-14 | LSRS | 4 | LQQKLKEYSLV | 6 |

EXAMPLE 9

Identification of GPCR-Binding High Affinity Peptide Analogs (Panning)

The methods of Example 7 were repeated using recombinant reconstituted β₂ adrenergic receptor panned with the Gs Library. Results of the panning screens and ELISA binding affinity of the selected peptides are shown in Table XIV, below.

TABLE XIV

β2-Adrenergic Receptor screened with Gs library.

| | SEQ ID NO: | | ELISA |
|---|---|---|---|
| Competitor | QRMHLRQYELL | 13 | |
| AG1 | QGMQLRRFKLR | 187 | .435 |
| AG20 | RWLHWQYRGRG | 188 | .431 |
| AG19 | PRPRLLRFKIP | 189 | .361 |
| AG2 | QGEHLRQLQLQ | 190 | .330 |
| AG4 | QRLRLGPDELF | 191 | .291 |
| BAR1 | QRIHRRPFKFF | 192 | .218 |
| AG3 | QRMPLRLFEFL | 193 | .217 |
| BAR2 | QRVHLRQDELL | 194 | .197 |
| AG11 | DRMHLWRFGLL | 195 | .192 |
| AG9 | QRMPLRQYELL | 196 | .190 |
| BAR3 | QWMDLRQHELL | 197 | .185 |
| AG18 | QRMNLGPCGLL | 198 | .155 |
| BAR20 | NCMKFRSCGLF | 199 | .079 |
| AG13 | QRLHLRGYEFL | 200 | .054 |
| BAR11 | HRRHIGPFALL | 201 | .048 |
| BAR8 | ERLHRRLFQLH | 202 | .047 |
| BAR40 | PCIQLGQYESF | 203 | .028 |
| BAR31 | QRLRLRKYRLF | 204 | .026 |

EXAMPLE 10

Identification of GPCR-Binding High Affinity Peptide Analogs (Panning).

The methods of Example 7 repeated using rhodopsin screening with a Gt library. Results of the panning screens and ELISA binding affinity of the selected peptides are shown in Table XV, below.

TABLE XV

Rhodopsin screened with Gt library.

| | | SEQ ID NO: | ELISA |
|---|---|---|---|
| Competitor | IRENLKDCGLF | 124 | |
| L33 | IVEILEDCCLF | 205 | 1.007 |
| L4 | MLDNLKACGLF | 206 | .908 |
| L3 | ILENLKDCGLF | 207 | .839 |
| L14 | LRENLKDCGLL | 208 | .833 |
| L38 | LLDILKDCGLF | 209 | .823 |
| L15 | VRDILKDCGLF | 210 | .621 |
| L34 | ILESLNECGLF | 211 | .603 |
| L17 | ILQNLKDCGLF | 212 | .600 |
| L7 | MLDNLKDCCLF | 213 | .525 |
| L10 | IHDRLKDCGLF | 214 | .506 |
| L20 | IRGSLKDCGLF | 215 | .423 |
| L6 | ICENLKDCGLF | 216 | .342 |
| L8 | IVKNLEDCGLF | 217 | .257 |
| L13 | ISKNLRDCGLL | 218 | .187 |
| L10 | IRDNLKDCGLF | 219 | .162 |

EXAMPLE 11

Additional Peptide Analogs.

Chinese hamster ovary-expressed PAR1 was screened against the Gt, G12 and G13 libraries, using the competitor peptide indicated in Table XVI below. Additional peptide analogs were identified using the G11 library and LQLN-LKEYNLV (SEQ ID NO:2) as competitor and screened for high affinity binding to PAR1 receptor obtained from different sources, indicated in Table XVII, below.

TABLE XVI

Peptides Identified with CHO EXPRESSED PAR1.

| Gt library (IRENLKDCCLF; SEQ ID NO:124) | | G12 library (LQENLKIDIMLQ; SEQ ID NO:38) | | G13 library (LQDNLKQLMLQ; SEQ ID NO:233) | |
|---|---|---|---|---|---|
| IREFLTDCGLF | 219 | LQENLKEMMLQ | 225 | LQDNLRHLMLQ | 234 |
| IRLDLKDVSLF | 220 | LEENLKYRMLD | 226 | LQDKINHLMLQ | 235 |
| ICERLNDCGLC | 221 | LQEDLKGMTLQ | 227 | LQANRKLGMLQ | 236 |
| PRDNTKVRCLF | 222 | LQETMKDQSLQ | 228 | LIVKVKQLIWQ | 237 |
| FWGNLQDSGLF | 223 | PQVNLKSIMRQ | 229 | MRAKLNNLMLE | 238 |
| RRGNGKDCRHF | 224 | WQHKLSEVMLQ | 230 | LQDNLRHLIQ | 239 |
| | | LKEHLMERMLQ | 231 | LQDNRNQLLF | 240 |
| | | LLGMLEPLMEQ | 232 | | |

TABLE XVII

PAR1 Binding Peptides Screened using a G11 Library (LQLNLKEYNLV; SEQ ID NO:2)

| CHO EXPRESSED | SEQ ID NO: | Recomb/Reconst | SEQ ID NO: | SF9 EXPRESSED | SEQ ID NO: |
|---|---|---|---|---|---|
| LQLNVKEYNLV | 163 | LQLNVKEYNLV | 163 | LQLNLKVYNLV | 175 |
| LQLNRKNYNLV | 241 | LQLRVKEYKRG | 244 | LQLKHKENNLM | 100 |
| LQLRYKCYNLV | 161 | LQLRYKCYNLV | 161 | LQKNLKEYNMV | 106 |
| LQLDLKESNMV | 242 | LQIYLKGYNLV | 245 | LQVNLEEYHLV | 101 |
| LQLNLKKYNRV | 243 | LQFNLNDCNLV | 102 | LFLNLKEYSLV | 257 |
| LQLRVKEYKRG | 244 | LQRNKKQYNLG | 160 | LELNLKVYNLV | 258 |
| LQRNKKQYNLG | 160 | LQRNKNQYNLG | 254 | LPLNPKEYSLV | 109 |
| LQIYLKGYNLV | 245 | LQQSLIEYNLL | 111 | LPLNLIDFSLM | 259 |
| LQFNLNDCNLV | 102 | LRLDFSEKQLV | 105 | LPRNLKEYDLG | 260 |
| LQYNLKESFVV | 246 | LYLDLKEYCLF | 255 | LRLNDIEALLV | 261 |
| LQQSLIEYNLL | 111 | HQLDLLEYNLG | 104 | LVLNRIEYNLL | 262 |
| LQRDHVEYKLF | 247 | VQVKLKEYNLV | 251 | LHLNMAEVSLV | 177 |
| LVIKPKEFNLV | 248 | MKLKEEDNLV | 103 | MNLTLKECNLV | 110 |
| IQLNLKNYNIV | 249 | SAKELDQYNLG | 256 | MKLNVSESNLV | 94 |
| HQLDLLEYNLG | 104 | | | LKRYLKESNLV | 178 |
| MQLNLKEYNLV | 250 | | | LKRKLKESNMG | 263 |
| VQVKLKEYNLV | 251 | | | LKRKVKEYNLG | 264 |
| QLLNQYVYNLV | 252 | | | | |
| MKLKLKEDNLV | 103 | | | | |
| WRLSLKVYNLV | 253 | | | | |

EXAMPLE 12

Preparation of LacI Lysates.

In the last round of panning, several clones were selected from the (+) receptor plates and grown up overnight in LB-Amp media. Three hundred microliters of the overnight culture was diluted in 3 mL in LB-Amp media for "ELISA lysate culture." Another 30 μL was added to an equal volume of 50% glycerol was stored in labeled microcentrifuge tubes at −70° C. The remaining 4.5 mL was used to make DNA using a standard miniprep protocol (Qiagen Spinprep™ kits) and sequenced using a 19 base pair reverse primer which is homologous to the vector at a site 56 basepairs downstream from the TAA stop codon that terminates the random region of the library (GAAAATCTTCTCTCATCCG; SEQ ID NO:306). The DNA was stored at −20° C. The ELISA lysate culture was allowed to shake for one hour at 37° C. Expression was induced by adding 33 μL 20% arabinose (0.2% final concentration) with shaking at 37° C. for 2–3 hours. The culture then was subjected to sedimentation at 4000×g for five minutes, the pellet resuspended in 3 mL cold WTEK buffer, resedimented at 4000×g for five minutes and the pellet resuspended in 1 mL cold TEK buffer. After transfer to 1.5 mL microcentrifuge tubes, the pellet was sedimented at 13,000×g for two minutes and the supernatant aspirated. The cell pellet was resuspended in 1 mL lysis buffer (42 mL HE, 5 mL 50% glycerol, 3 mL 10 mg/mL BSA in HE, 750 μL 10 mg/mL lysozyme in HE and 62.5 μL 0.2 M PMSF) and incubated on ice for one hour. One hundred ten microliters 2M KCl was added to the lysis mixture and inverted to mix, then sedimented at 13,000×g for 15 minutes at 4° C. The clear crude lysate (about 0.9 mL supernatant) was transferred to a new tube and stored at −70° C.

EXAMPLE 13

PAR1 Receptor-Specific Binding of LacI-Peptide Fusion Proteins.

Figure 4:
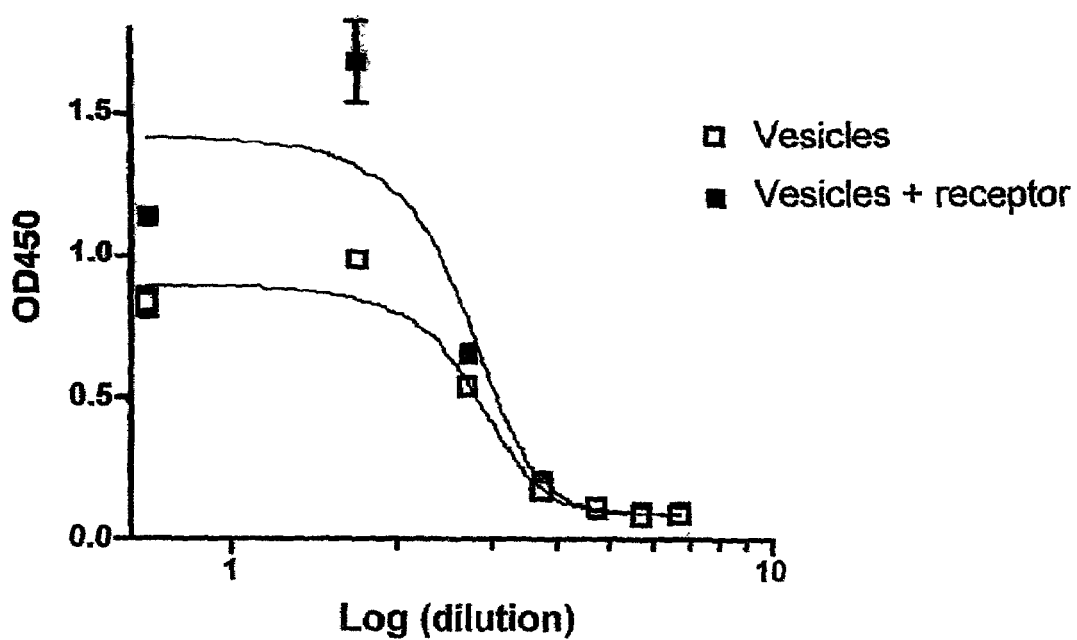
FIG. 4 provides binding data for LacI peptide fusion proteins to PAR1 receptor. pELM6 is the MBP vector alone; pELM17 is the MBP-native Gt340–350 peptide fusion protein.

The binding properties of the peptide encoded by individual clones were assayed as follows. Purified PAR1 receptor prepared from Sf9 insect cells (1–10,000 pg/mL in 50 mM Tris HCl, pH 7.4, 10% glycerol) was reconstituted in lipid vesicles according to Example 6. A serial dilution of the membranes containing receptor ranging from 0.2 to 20,000 μg/mL (+/−receptor) was added to wells on a microtiter plate and shaken gently for one hour at 4° C. After washing, a 1:1 to 1:10,000 serial dilution of a LacI-Gq lysate prepared from the LacI-Gq clone according to the methods described in Example 12 was added to the wells, the plate was shaken gently for one hour at 4° C, and washed. Anti-LacI antibodies (Stratagene) were added (1:1000) and the plate shaken gently for one hour at 4° C. After washing, HRP-conjugated goat anti-rabbit antibodies (Kierkegaard and Perry Laboratories) were added (1:2500) and the plate shaken gently for one hour at 4° C. The plate was washed, color was developed using horseradish peroxidase, and then read in an ELISA reader at $OD_{450}$. The general methodology for the ELISA is illustrated in FIG. 3. The results, see FIG. 4, show that the LacI-Gq fusion protein binds thrombin receptor in a concentration dependent manner. The ability of the LacI-Gq fusion protein to bind the empty vesicles was significantly less than vesicles reconstituted with thrombin receptor.

EXAMPLE 14

Screening in the Presence of a High Affinity Peptide.

To identify peptides having even higher affinity to light-activated rhodopsin than those identified by the panning procedure described in Example 7, a high affinity peptide was included in the library incubations in rounds three and four. Peptide 8 (LLENLRDCGMF; SEQ ID NO:125) had been identified in the first screening as a peptide exhibiting binding to light-activated rhodopsin 1000-fold higher than the native sequence. Screening of the Gα library was performed as in Example 7, except that 10 μL 100 μM (100 nM final concentration) peptide 8 was included in the wells in rounds three and four. This screen revealed several clones that both bind rhodopsin with very high affinity and stabilize it in its active form, metarhodopsin II. See Table XVIII, below. Comparing Tables IX and XVIII, it is clear that the use of peptide 8 in the screen resulted in a change at position 341 to a neutral residue. Residues L344, C347 and G348 remained stable whether peptide 8 was included in the screen or not. Use of peptide 8 resulted in a higher incidence of isoleucine at position 340 (17% with native peptide versus 71% with peptide 8) and a lower incidence of glutamine at position 342 (67% with native peptide versus 29% with peptide 8). This type of information not only contributes to the discovery of highly potent analog peptides for use as drugs or drug screening compounds, but also furthers the understanding of the structural framework which underlies the sites of contact between Gα and receptor.

Figure 5:
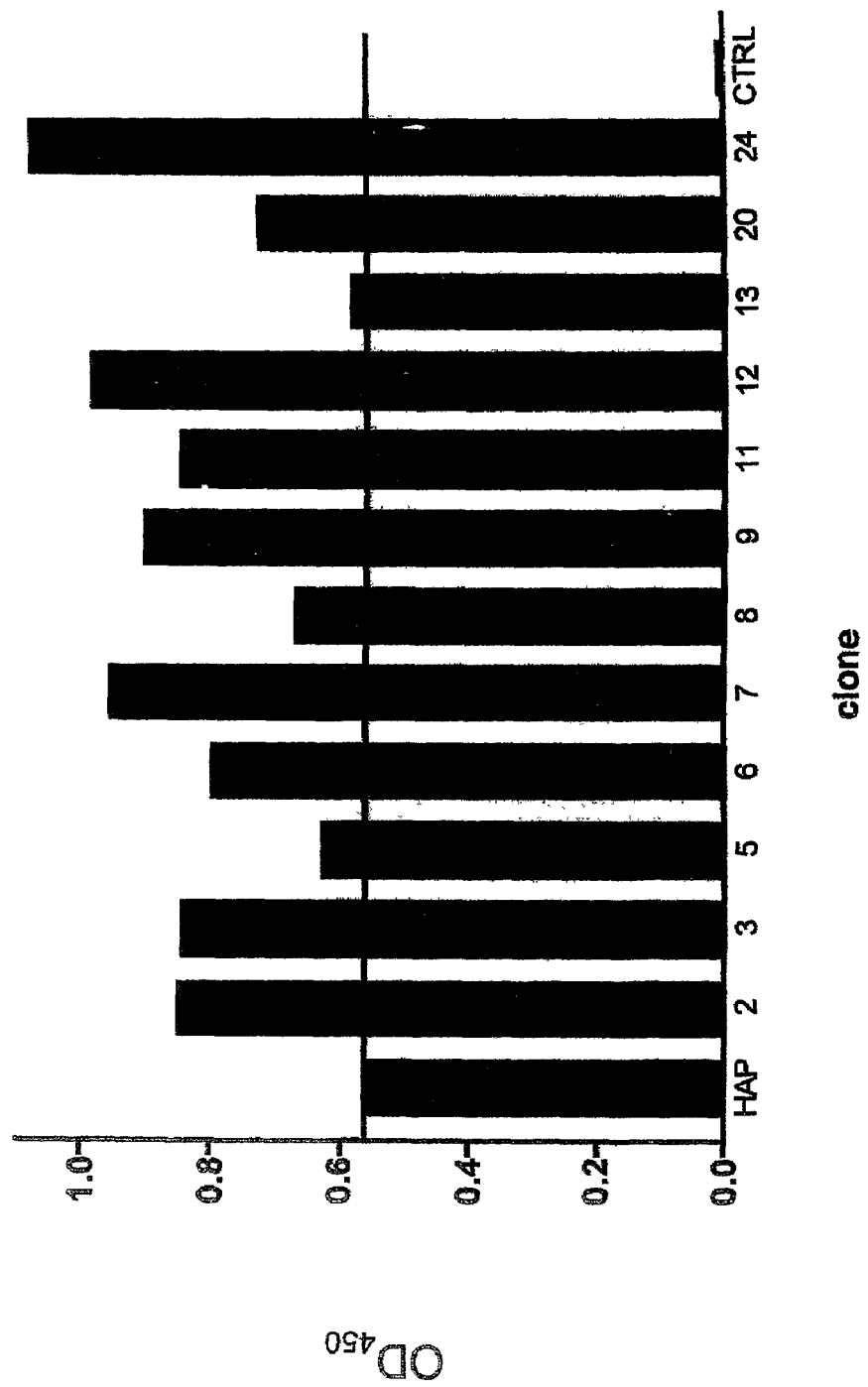
FIG. 5 is a bar graph comparing binding of high affinity clones to the clone of peptide 8.

Binding assays performed on some of the clones identified in this way are shown in FIG. 5. All peptides identified using peptide 8 in the screening process bound with equal or greater affinity to light-activated rhodopsin as did peptide 8. Compare the first bar (HAP=peptide 8) with the remaining bars.

TABLE XVIII

Exemplary Light-Activated Rhodopsin High Affinity Sequences Identified in Screens with Addition of Peptide 8.

| Clone No. | SEQ ID NO: | Sequence |
|---|---|---|
| Library Sequence | 124 | IRENLKDCGLF |
| Peptide 8 | 125 | LLENLRDCGMF |
| 3 | 266 | ILENLKDCGLL |
| 7 | 213 | MLDNLKDCGLF |
| 8 | 216 | IVKNLEDCGLF |
| 10 | 218 | IRDNLKDCGLF |
| 13 | 217 | ISKNLRDCGLL |
| 17 | 212 | ILQNLKDCGLF |
| 19 | 206 | MLDNLKACGLF |

EXAMPLE 15

Subcloning into MBP Vectors and Preparation of MBP Crude Lysates.

pELM3 was digested at room temperature with AgeI (New England Biolabs) and the cut vector was separated from uncut vector on a 0.7% agarose gel. DNA was purified (Qiagen Extract-a-gel kit) and digested with ScaI (New England Biolabs). The 5.6 kb MBP vector fragment was seperated on a 1% agarose gel and purified as above. During the final affinity purification round of the peptide Library, a 20 mL portion of the 200 mL amplification culture was set aside before harvesting the cells. This 20 mL portion was allowed to grow to saturation, usually overnight prepared from the cells (Qiagen midi-prep kit). The pJS142 plasmid DNA was digested with BspEI and ScaI. The 0.9 peptide-encoding fragment was separated from the 3.1 and 1.7 kb vector fragments on a 1% agarose gel and purified.

Different ratios of the 5.6 kb MBP vector fragment and the peptide-encoding 0.9 kb fragment (1:2, 1:1, 2.5:1, 5:1, 10:1) were ligated in ligase buffer containing 0.4 mM ATP at 14° C. overnight with T4 DNA ligase. The ligation was terminated by increasing the temperature to 65° C. for ten minutes. To lower the background, the ligation mixture was digested with XbaI before isopropanol precipitation using 1 μL glycogen as a carrier. After one wash with 80% ethanol, the pellet was resuspended in 20 μL double-distilled water. ARI814 cells were transformed as described in Example 7 using 1 μL of the precipitated XbaI digested ligation mix. After allowing the cells to shake for one hour at 37° C. in 1 mL SOC, 100 μL of the suspension was spread on LB-Amp Plates. Crude lysates were prepared as described for LacI lysates in Example 9.

EXAMPLE 16

MBP—Peptide Fusion Protein Purification.

An overnight culture (1 mL) of a single MBP-peptide fusion protein clone was inoculated into 200 mL LB-AMP media. The culture was shaken at 37° C. until $OD_{600}=0.5$. Protein expression was induced by addition of 150 μL 1 M IPTG (final concentration 0.3 mM), with continued shaking at 37° C. for two hours. The culture then was sedimented at 5000×g for 20 minutes and resuspended in 5 mM column buffer (10 mM Tris, pH 7.4; 200 mM NaCl; 1 mM EDTA; 1 mM DTT) and 16.25 μL 0.2 M PMSF was added. The resuspended cell pellet was then stored at −70° C. The stored pellet was thawed in cold water and placed in an ice bath. The pellet was sonicated in short pulses of less than 15 seconds with a Fisher Scientific 55 Sonic Dismembrator (40% constant time, output 5, repeating five times with a total one minute duration). The sonicated pellet was subjected to centrifugation at 9000×g for 30 minutes, after which the supernatant was saved and diluted to 100 mL using column buffer. Usually, the protein concentration was approximately 2.5 mg/mL. A column was prepared by pouring 7.5 ml amylose resin in a BioRad disposable column and washing with eight volumes of column buffer. The diluted crude extract was loaded by gravity flow at about 1 mL/min and the column was washed again with eight volumes of column buffer. The fusion protein was eluted with 10 mL 10 mM maltose in column buffer and concentrated using Amicon centriplus 30™ columns, then aliquoted and stored at −70° C.

EXAMPLE 17

Method for Screening Library Crude Lysates by ELISA.

Microtiter wells were coated with 0.1–1.0 μg/well rhodopsin receptor in a final volume of 100 μL HEK containing 1 mM DTT with shaking at 4° C. for one hour. The wells then were blocked with bovine serum albumin (BSA) by adding 100 μL 2% BSA in HEK with 1 mM DTT to the wells and continuing shaking at 4° C. for at least 30 minutes, then washed four times with HEK containing 1 mM DTT. Crude lysates were diluted 1:50 in HEK containing 1 mM DTT and added to the coated wells (100 μL per well). The plates were shaken at 4° C. for one hour, washed four times with PBS/0.05% Tween™20 1 mM maltose and then probed with 100 μL 1:1000 rabbit anti-MBP antibodies (New England BioLabs) in PBS containing 0.05% Tween™ 20 and 1 mM maltose, with shaking for 30 minutes at 4° C. After another wash, the wells were probed with 100 μL 1:7500 goat anti-rabbit secondary antibodies conjugated to horseradish peroxidase in PBS containing 1% BSA and 1 mM maltose with shaking for 30 minutes at 4° C. The plate was washed four times with PBS containing 0.05% Tween™ 20 and 1 mM maltose. Horseradish peroxidase substrate (Bio-Fx; 100 μL) was added and the color developed for 20–30 minutes. The reaction was stopped by addition of 100 μL 2N sulfuric acid and the plate read at $OD_{450}$. If the color reaction occurred too quickly (less than 10 minutes) or if the background in negative control wells was too high (greater than 0.2) the assay was repeated using 1:100 or 1:200 dilutions of the crude lysates.

EXAMPLE 18

Binding Assay of High Affinity Rhodopsin Binding Peptides.

The entire population of peptide-coding sequences identified in round 4 of panning (see Example 7) was transferred from pJS142 to pELM3 (New England Biolabs). This plasmid is a pMal-c2 derivative with a modified polylinker, inducible by isopropyl β-thiogalacto-pyranoside and containing the E. coli malE gene with a deleted leader sequence and leads to cytoplasmic expression of MBP fusion proteins. The MBP-carboxyl terminal peptide analog fusion proteins were expressed in E. coli.

Figure 6:
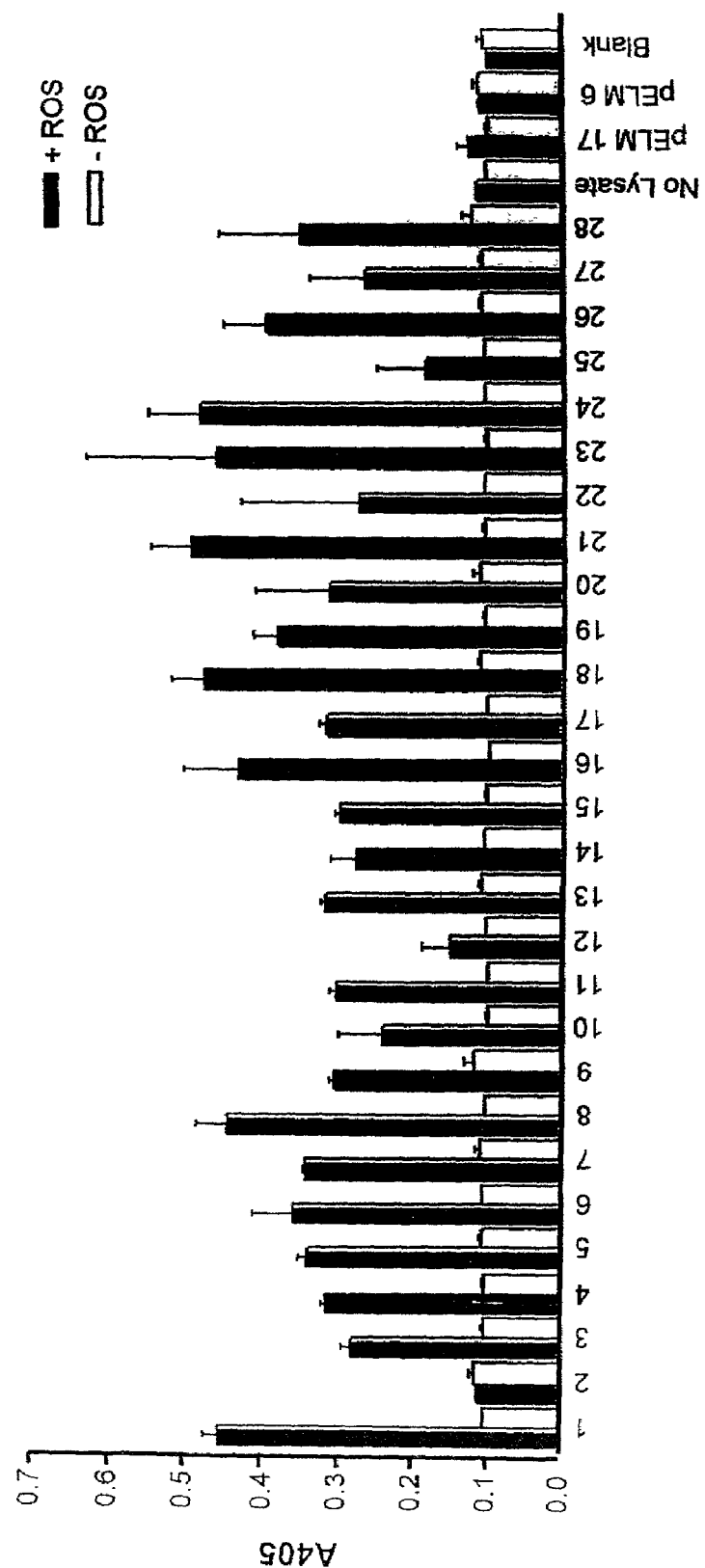
FIG. 6 is a bar graph presenting results of a competitive binding assay identifying high affinity rhodopsin binding peptides.

For the assay, in the dark, 1 μg/well of ROS membranes (rhodopsin) as described in Example 5 was directly immobilized on microtiter wells in cold HEK/DTT for one hour at 4° C. The wells were rinsed, blocked with 1% BSA in HEK/DTT for one hour at 4° C. and rinsed again. Bound rhodopsin was activated by exposure to light for 5 minutes on ice before addition of the MBP fusion proteins (crude bacterial lysates were diluted 1:50 in HEK with 1 μM dithiothreitol; purified proteins were used at 0.2–120 nM). The MBP-Gαt340–350K341R (pELM17) fusion protein and MBP with linker sequence only (pELM6) were present in control wells at 50 nM final concentration. After 30 minutes, wells were washed and rabbit anti-MBP antibody (New England Biolabs) was added. The anti-MBP antibody was used at a 1:1000 dilution for crude lysates and a 1:3000 dilution for purified proteins. After 30 minutes, wells were rewashed and goat anti-rabbit antibody conjugated to horseradish peroxidase (1:7500 dilution for crude lysates; 1:10,000 dilution for purified proteins; Kierkegaard & Perry Laboratories) was added. After 30 minutes, the plate was washed four times with PBS containing 0.05% Tween™20. Horseradish peroxidase substrate (100 μL) was added and color was allowed to develop for about 20 minutes. The reaction was stopped by addition of 100 μl 2N sulfuric acid. The results are presented in FIG. 6. Values indicate absorbence at $OD_{450}$. The controls for the assay was pELM 17, which encodes the MBP fusion protein Gα$_t$340–350K341R. pELM6, which expresses MBP protein fused to a linker sequence only, served as the negative control. "No lysate" control wells were included to reflect any intrinsic, non-specific binding within the assay. See FIG. 6.

The $IC_{50}$ values of the high affinity MBP fusion proteins ranged from 3.8 to 42 nM, up to 3 orders of magnitude more potent than the 6 μM $IC_{50}$ of MBP-Gαt340–350K341R. In all the highest affinity sequences, position 341, which is a positively charged residue in the native sequence, was changed to a neutral residue. Leu344, Cys347, and Gly348 were found to be invariant and hydrophobic residues were always located at positions 340, 349, and 350, indicating the critical nature of these residues.

EXAMPLE 19

Binding of High Affinity Peptides to Rhodopsin can be Competitively Inhibited by Heterotrimeric Gt.

Binding of MBP fusion proteins containing the high affinity peptide from the library (sequences from clones 8, 9, 10, 18, 23, 24, as well as pELM17 which encodes the wild-type peptide sequence, and pELM6 which contains on peptide) were assessed for their ability to bind rhodopsin (0.5 µg rhodopsin/well) in the presence or absence of heterotrimeric Gt. Lysate (50 µL from each clone was added and incubated in the light. After 45 minutes, 1 µM heterotrimeric Gt was added and the solution incubated for 30 minutes. Anti-MBP antibody was added, followed by goat anti-rabbit alkaline phosphatase conjugated antibody and substrate. The color was allowed to develop. Absorbence data are presented in FIG. 7.

EXAMPLE 20

Binding of MBP Clones to PAR1

Figure 8:
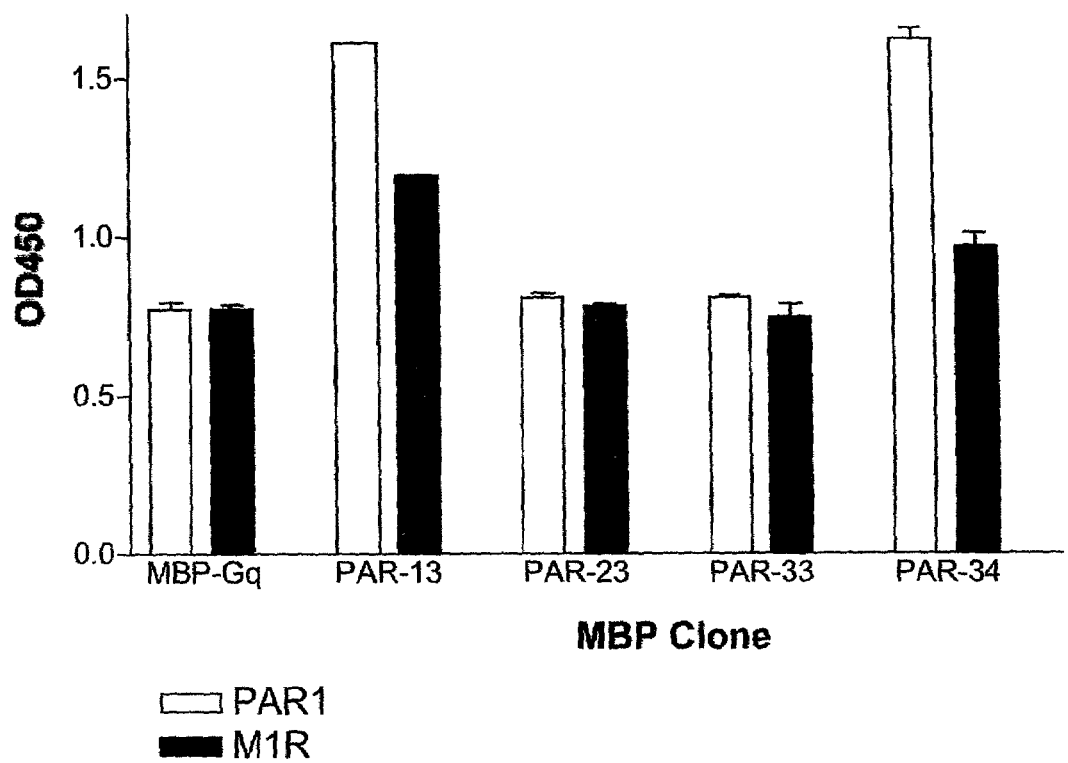
FIG. 8 presents ELISA results from panning CHO cells overexpressing human thrombin receptor (PAR1) using purified MBP-C-terminal fusion proteins. MBP-G11=xxxx (SEQ ID NO: 1) LQLNLKEYNLV (SEQ ID NO: 2); PAR-13=VRPS (SEQ ID NO: 3) LQLNRNEYYLV (SEQ ID NO: 4); PAR-23=LSRS (SEQ ID NO: 5) LQQKLKEYSLV (SEQ ID NO:6); PAR-33=LSTN (SEQ ID NO: 7) LHLNLKEYNLV (SEQ ID NO: 8); PAR-34=LPQM (SEQ ID NO: 9) QRLNVGEYNLV (SEQ ID NO: 10); PAR-45=SRHT (SEQ ID NO: 11) LRLNGKELNLV (SEQ ID NO:12).

To identify high affinity peptides that bind PAR1, membranes prepared from mammalian cells (Chinese hamster ovary) overexpressing PAR1 were panned with the G11 peptide library. ELISA binding affinity results of selected clones are shown in FIG. 8 for their binding to membranes prepared from SF9 cells expressing either PAR1 or the Gq-coupled muscarinic M1 receptor. To quantitate the binding, purified MBP clones were analyzed using ELISA methods in which the secondary antibody was conjugated to HRP. The binding for the control MBP-Gq fusion protein is shown. See FIG. 8. The data are the average of two separate experiments done in duplicate. MBP clones PAR-13 and PAR-34 both show both high affinity binding for PAR1 as well as specificity. MBP clones PAR-23 and PAR-33 appear to be both of low affinity and low specificity. See Table XIII for the sequences.

EXAMPLE 21

Binding Specificity of LacI-Peptide Fusion Proteins.

Figure 9:
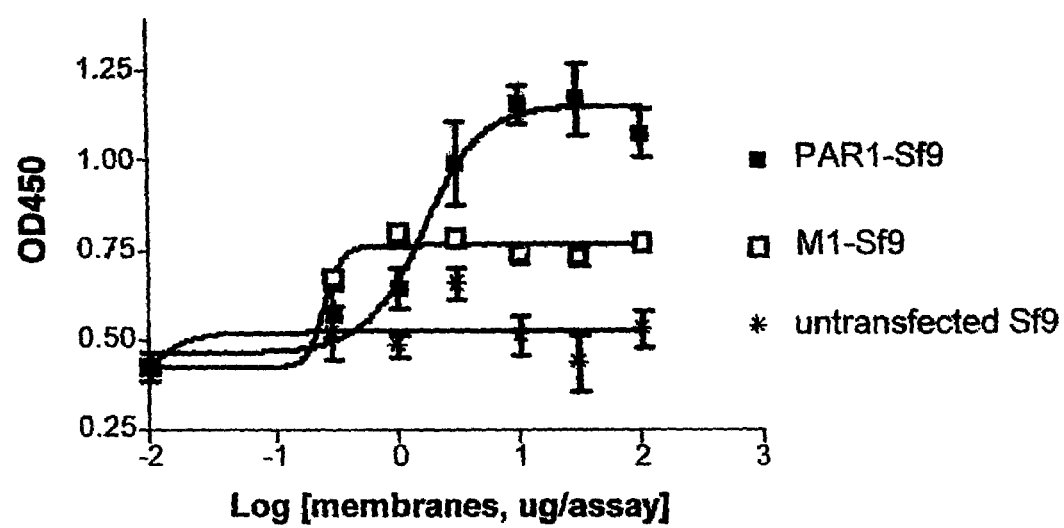
FIG. 9 presents a dose-response curve of SF9 membranes (PAR1 receptor) assayed with lacI-Gq lysates.

PAR1 binding clones of LacI-peptide fusion protein selected from the G11 Library were diluted 1:100 in HEK/ DTT and tested for dose-responsive binding to Sf9 insect cell membranes from cells expressing no receptor, the M1 receptor (which couples to Gi) or PAR1 receptor, prepared according to Example 2. Increasing amounts of membrane as indicated in FIG. 9 were coated in microtiter wells, incubated and rinsed. LacI-peptide fusion protein lysates were added, incubated and rinsed, and the receptor-bound LacI-peptide fusion protein was measured as described above using a LacI antibody. Results for a single, representative clone are presented in FIG. 9, and demonstrate the specificity of the selected peptides for PAR1.

EXAMPLE 22

Binding of Native Gαq-Maltose Binding Protein-Peptide Fusion Protein to PAR1.

Figure 10:
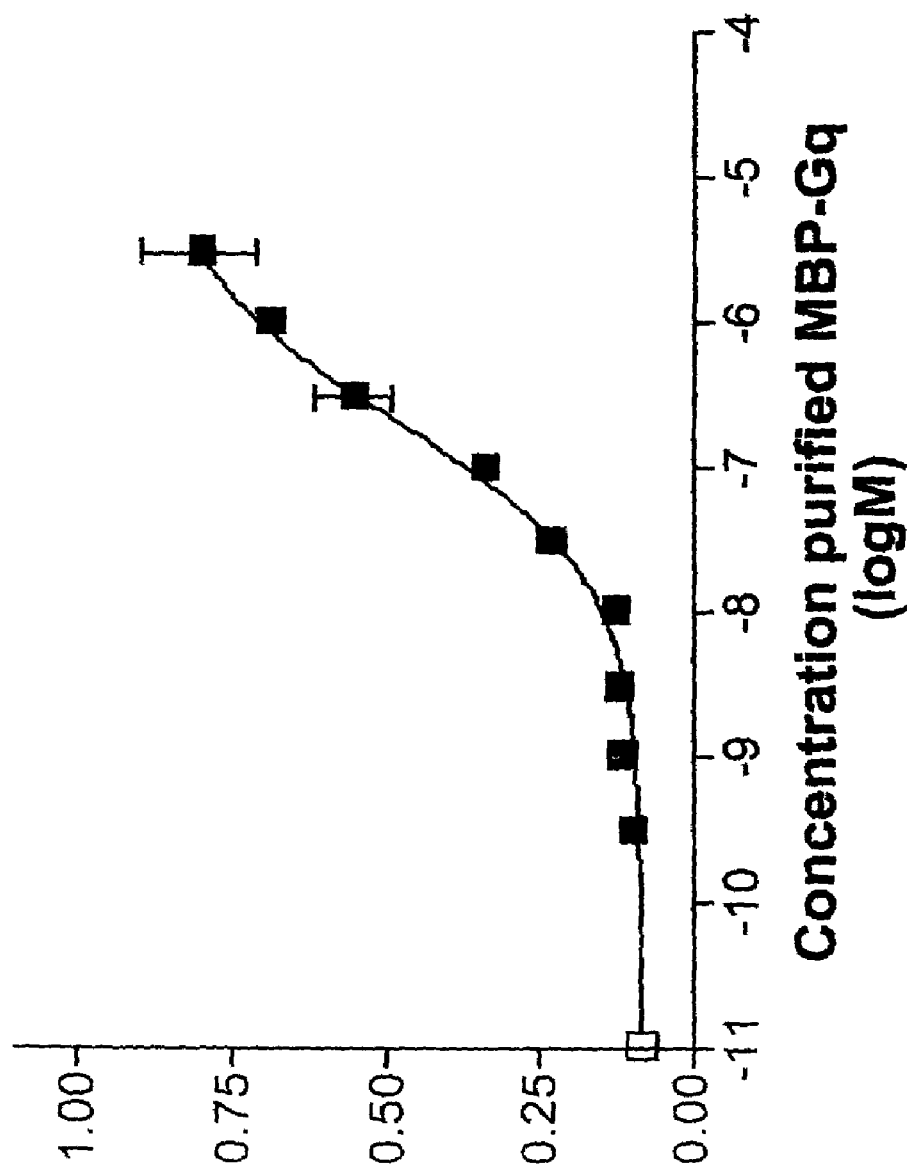
FIG. 10 is a concentration response curve demonstrating binding of native Gq peptide-maltose binding protein to PAR1 reconstituted in lipid vesicles.

Microtiter wells were coated with purified, reconstituted PAR1 in the presence of 100 nmoles thrombin receptor activating peptide, as described above in Example 6. Purified maltose binding protein-Gαq (MBP-Gαq) was added at the concentrations indicated in FIG. 10 and incubated one hour on a shaker at 4° C. The wells were rinsed and then probed with a rabbit anti-maltose binding protein antibody, followed by alkaline phosphatase conjugated secondary antibodies, as described above. Substrate was added and the color was allowed to develop about 20 minutes. Absorbence at 405 nm was measured and dose-response curves were calculated using GraphPad Prism (version 2.0). See results in FIG. 10. The calculated $IC_{50}$ of Gαq binding to activated PAR1 was 214 nM.

EXAMPLE 23

Figure 11:
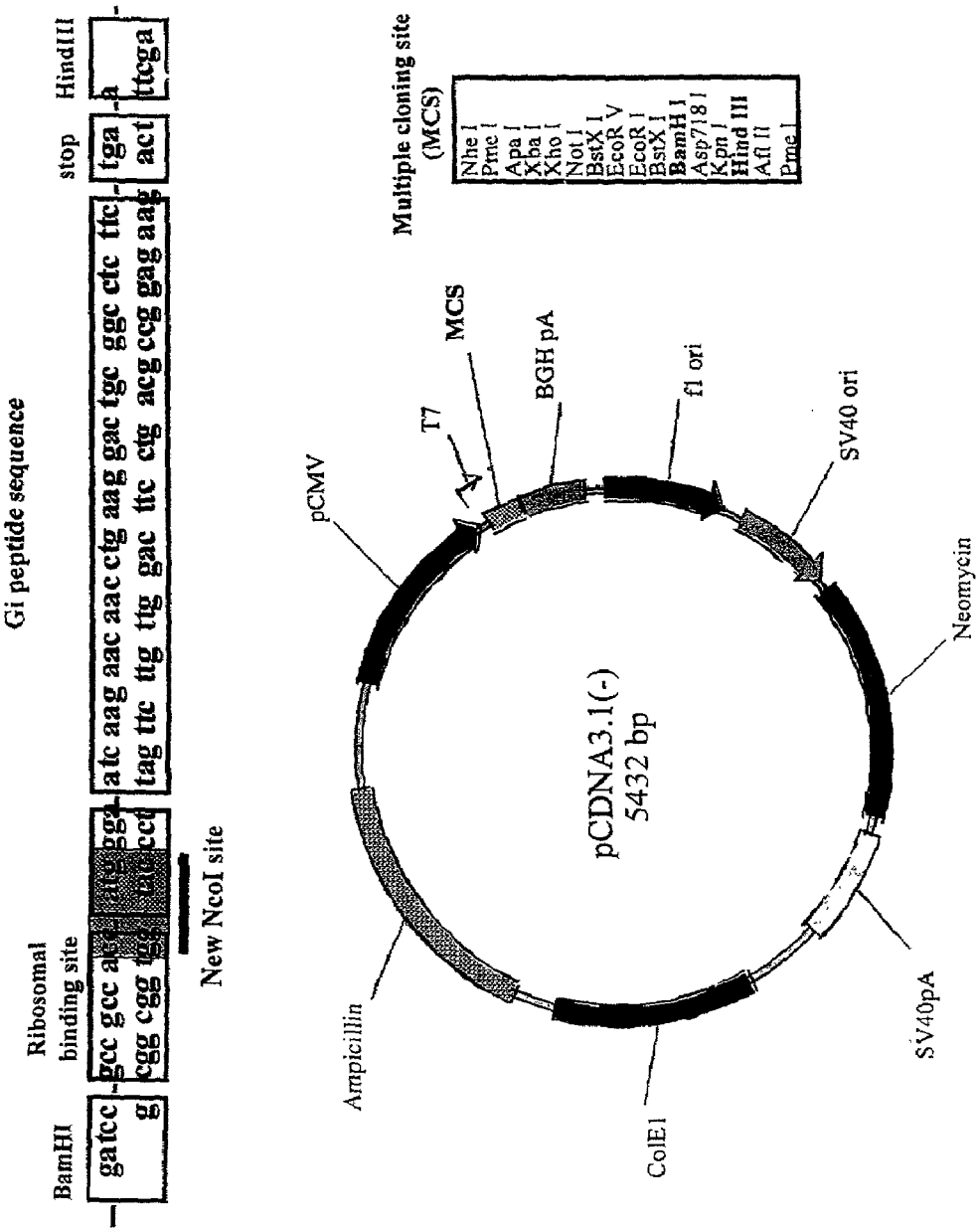
FIG. 11 is a schematic diagram showing an exemplary cDNA minigene construct.
Figure 12:
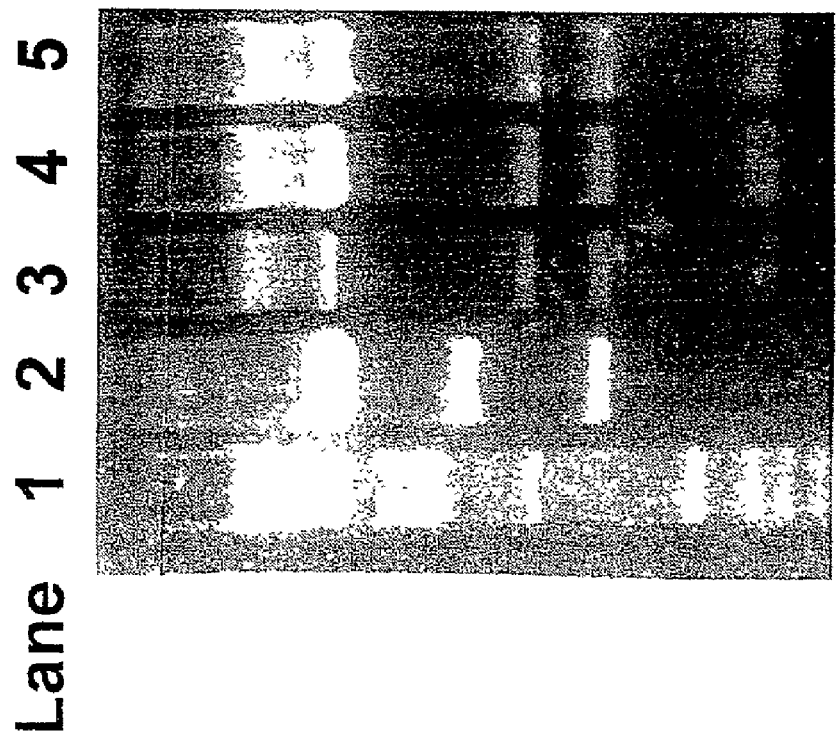
FIG. 12 is an agarose gel of a NcoI digest of minigene vector. Lane 1 is a 1 kb DNA ladder; lane 2 is pcDNA 3.1; lane 3 is pcDNA-Gαi; lane 4 is pcDNA-GαiR; and lane 5 is pcDNA-Gαq.

Design of Oligonucleotides for Gα Peptide Minigene Constructs.

cDNA encoding the last 11 amino acids of Gα subunits was synthesized (Great American Gene Company) with newly engineered 5'- and 3'-ends. The 5'-end contained a BamHI restriction enzyme site followed by the human ribosome-binding consensus sequence (5'-GCCGCCACC-3'; SEQ ID NO:314), a methionine codon (ATG) for translation initiation, and a glycine codon (GGA) to protect the ribosome binding site during translation and the nascent peptide against proteolytic degradation. A HindIII restriction enzyme site was synthesized at the 3' end immediately following the translational stop codon (TGA). Thus, the full-length 56 bp oligonucleotide for the $G\iota\alpha_{1/2}$ carboxyl terminal sequence was 5'-gatccgccgccaccatgggaatcaagaa-caacctgaaggactgcggcctcttctgaa-3' (SEQ ID NO:315) and the complimentary strand was 5'-agctttcagaagaggccgcagtcct-tcaggttgttcttgattcccatggtggcggcg-3' (SEQ ID NO:316). See FIG. 11. As a control, oligonucleotides encoding the $G\alpha i_{1/2}$ carboxyl terminus in random order (GαiR) with newly engineered 5'- and 3'-ends also were synthesized. The DNA was diluted in sterile ddH$_2$O to form a stock concentration at 100 µM. Complimentary DNA was annealed in 1×NEB-uffer 3 (50 mM Tris-HCl, 10 mM MgCl$_2$, 100 mM NaCl, 1 mM DTT; New England Biolabs) at 85° C. for 10 min then allowed to cool slowly to room temperature. The DNA then was subjected to 4% agarose gel electrophoresis and the annealed band was excised. DNA was purified from the band using a kit, according to the manufacture's protocol (GeneClean II Kit, Bio101). After digestion with each restriction enzyme, the pcDNA 3.1(−) plasmid vector was subjected to 0.8% agarose gel electrophoresis, the appropriate band cut out, and the DNA purified as above (GeneClean II Kit, Bio101). The annealed/cleaned cDNA was ligated for 1 hour at room temperature into the cut/cleaned pcDNA 3.1 plasmid vector (Invitrogen) previously cut with BamHI and HindIII. For the ligation reaction, several different ratios of insert to vector cDNA (ranging from 25 µM:25 pM to 250 pM:25 pM annealed cDNA) were plated. Following the ligation reaction, the samples were heated to 65° C. for 5 min to deactivate the T4 DNA ligase. The ligation mixture (1 µL) was electroporated into 50 µL competent cells as described in Example 7 and the cells immediately placed into 1 mL of SOC (Gibco). After 1 hour shaking at 37° C, 100 µL of the electroporated cells containing the minigene plasmid DNA was spread on LB/Amp plates and incubated at 37° C. for 12–16 hours. To verify that insert was present, colonies were grown overnight in LB/Amp and their plasmid DNA purified (Qiagen SpinKit). The plasmid DNA was digested with NcoI (New England Biolabs, Inc.) for 1 hour at 37° C. and subjected to 1.5% (3:1) agarose gel electrophoresis. Vector alone produced 3 bands. When the 56 bp annealed oligonucleotide insert is present, there is a new NcoI site resulting in a shift in the band pattern such that the digest pattern goes from three bands (3345 bp, 1352 bp, 735 bp) to four bands (3345 bp, 1011 bp, 735 bp, 380 bp). See FIG. 12. DNA with the correct electrophoresis pattern was sequenced to confirm the appropriate sequence. This method may be used to insert any high affinity peptide to create a minigene constant.

EXAMPLE 24

Expression of Peptides from Minigene Constructs.

Expression of the GPCR binding peptides was achieved using constructs which included minigene inserts corresponding to the carboxyl terminal sequences of various G protein α subunits (Gαi, Gαo, Gαs, Gαq, Gα11, Gα12, Gα13, Gα14), as well as a control minigene containing the Gαi sequence in random order (GαiR). The minigene insert DNAs were made by synthesizing short complimentary oligonucleotides corresponding to the peptide sequences from the carboxyl terminus of each Gα with BamHI and HindIII restriction sites at the 5' and 3' ends, respectively. Complementary oligonucleotides were annealed and ligated into the mammalian expression vector pcDNBA3.1 according to the methods of Gilchrist et al., *J. Biol. Chem.* 274:6610–6, 1999, the disclosures of which are hereby incorporated by reference.

Figure 13:
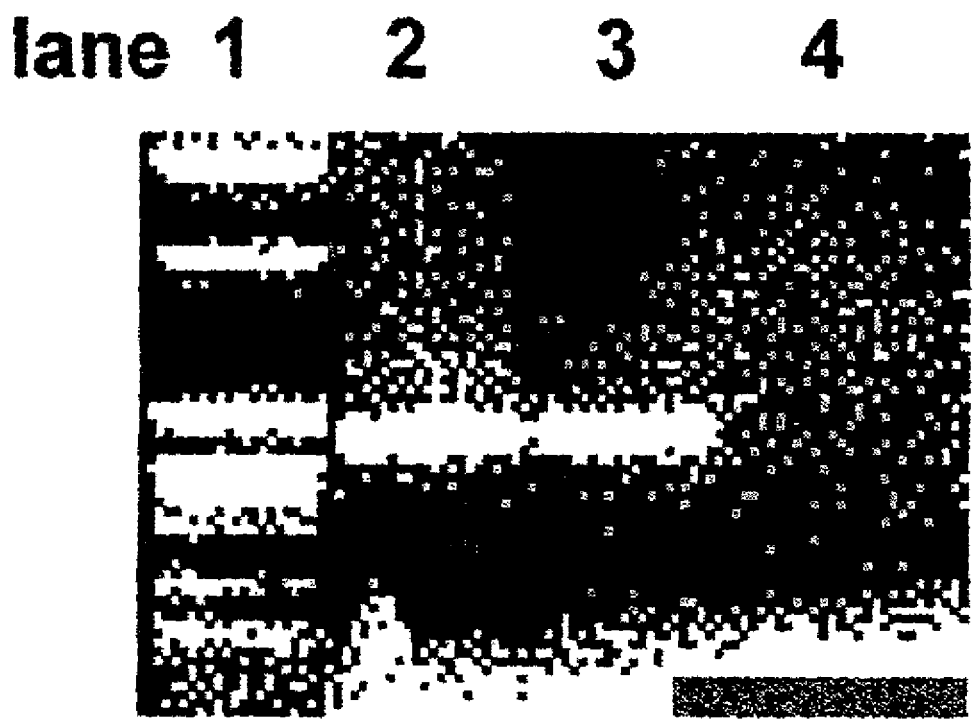
FIG. 13 is an agarose gel of PCR products showing transcription of peptide minigene RNA in transfected cells. Lane 1 contains size markers, lane 2 contains PCR products from cells transfected with pcDNA-GiR, lane 3 contains PCR products from cells transfected with pcDNA-Gi, and lane 4 contains PCR products from cells transfected with pcDNA3.1, the empty vector.

Human embryonic kidney (HEK) 293 cells were transfected using a standard calcium phosphate procedure according to the methods of Sambrook et al., Molecular Cloning: A Laboratory Manual, Cold Spring Harpor Laboratory Press, New York, vol. 1–3 (1989), the disclosures of which are hereby incorporated by reference. To confirm the transcription of minigene constructs in transfected cells, total RNA was isolated from the cells 48 hours post transfection with pcDNA-Gαi or pcDNA-GαiR using methods known in the art. Reverse transcriptase PCR was used to make cDNA and PCR analysis was performed using the cDNA as template with primers specific for the relevant Gα carboxyl terminal peptide insert (forward: 5'-ATCCGC-CGCCACCATGGGA (SEQ ID NO:270); reverse: 5'-GC-GAAAGGAGCGGGGCGCTA (SEQ ID NO:271). These primers for the Gα minigenes amplify a 434 bp fragment only if the inserted peptide-encoding oligonucleotides are present; no band is observed in cells transfected with the empty pcDNA3.1 vector. The PCR products were separated on 1.5% agarose gels. The presence of a single 434 bp band indicated that Gα carboxyl terminus peptide minigene RNA had been transcribed. See FIG. 13. Control experiments were done using a T7 forward primer with the vector reverse primer to verify the presence of the pcDNA3.1 vector, and G3DPH primers (Clonetech) to approximate the amount of total RNA.

To verify that the peptide was being produced in the transfected cells, the cells were lysed and homogenized 48 hours post transfection according to known methods. Cytosolic extracts were analyzed by gradient reversed phase HPLC as follows: 100 μL of cytosolic fraction extract was loaded onto a C4 column (Vydac) equilibrated with 0.1% TFA in ddH$_2$O. The peptide was eluted using 0.1% TFA in an acetonitrile gradient which increased from 0–60% over 45 minutes. Peaks were collected, lyophilized, and analyzed using ion mass spray analysis (University of Illinois-Urbana Champagne). Mass spectrometry analysis for peak 1 from Gαi$_{1/2}$ peptide vector (pcDNA-Gαi) transfected cells, and from cells transfected with pcDNA-GαiR indicated that a 1450 Dalton peptide (the expected molecular weight for both 13 amino acid peptide sequences) was present in each cytosolic extract. The minigene-encoded peptides were the major peptides found in the cytosol, strongly indicating that the vectors produced the appropriate peptide sequences in large amounts.

EXAMPLE 25

Interfacial G Protein Peptide Inhibition of Thrombin-Mediated Inositol Phosphate Accumulation.

HMEC were seeded onto 6-well plates 24 hours before transfection at 1×10$^5$ well. Cells were transiently transfected with pcDNA3.1, pcDNA-Gαi, pcDNA-GαiR, or pcDNA-Gq as described in Example 21. After 24 hours, cells were incubated in 2 mL culture medium containing 4 μCi/mL [$^3$H]-myoinositol to obtain steady-state labeling of cellular inositol lipids. Transiently transfected cells were assayed for inositol phosphate (IP) accumulation 48 hours after transfection. Two hours prior to stimulation with α-thrombin, cells were washed, and medium replaced with medium containing 5 mM LiCl. Cells were stimulated with 10 nM α-thrombin for 10 minutes. Inositol phosphate (IP) formation was stopped by aspiration of the medium and addition of ice-cold methanol (final concentration 5%).

Figure 14:
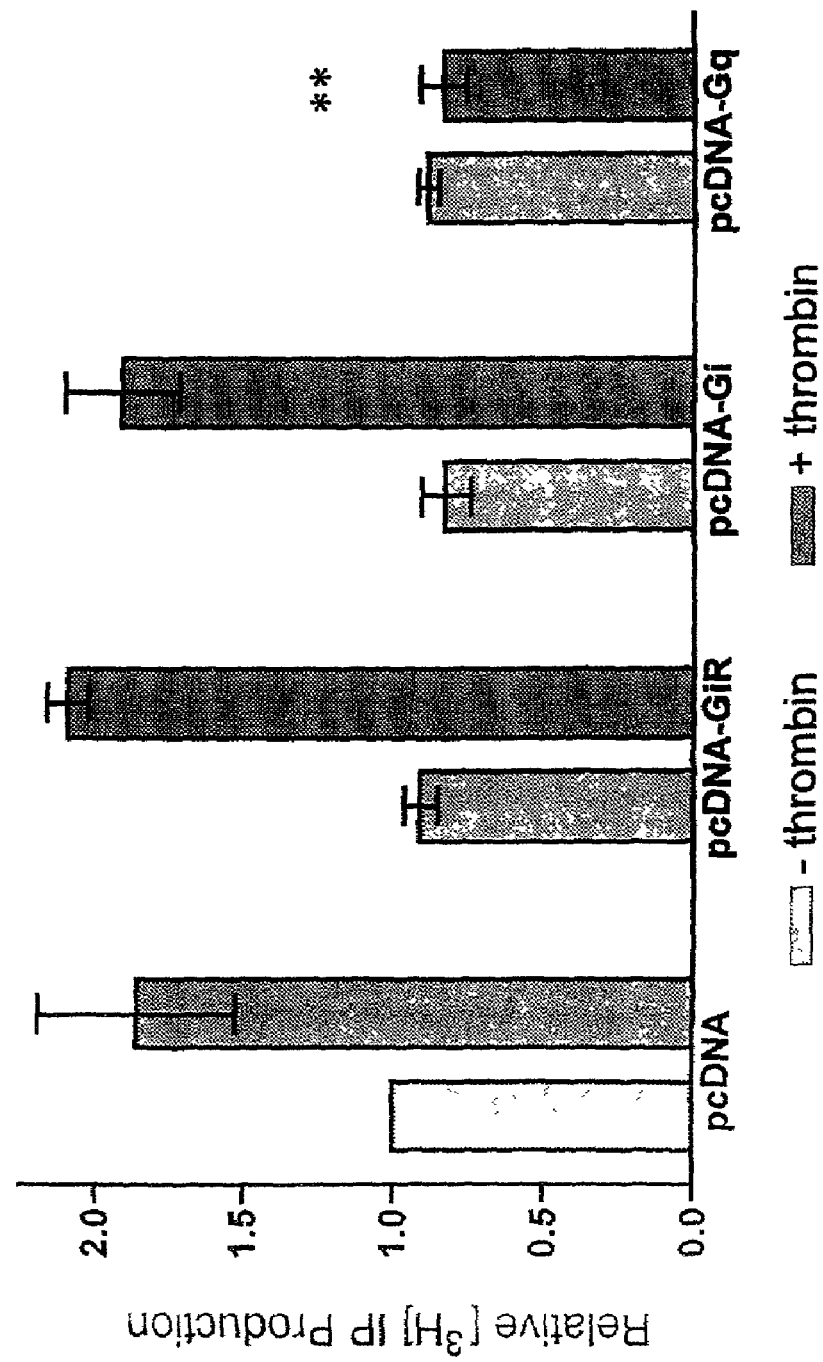
FIG. 14 is a bar graph showing the relative [$^3$H] inositol phosphate production after thrombin stimulation normalized against the basal value.

Perchloric acid-lysed cells were centrifuged at 2500 rpm, 4° C. for 5 min. The supernatant containing IP was eluted through a Poly-Prep chromatography column (Bio-Rad) containing 1.6 ml anion exchange resin (DOWEX AG1-X8, formate form, 200–400 mesh). The perchloric acid-precipitated pellets (containing phosphatidylinositols and lipids) were resuspended in 1 ml chloroform-methanol-10 M HCl (200:100:1, v/v/v). These suspensions were mixed with 350 μL HCl and 350 μL chloroform and sedimented for 5 min at 2500 rpm to separate the phases. The lower, hydrophobic phase was recovered and dried in counting vials to determine the amount of radioactivity in total phosphatidylinositols. The relative amount of [3H]-IP generated was calculated as follows: ([$^3$H]-IP (cpm)/[$^3$H]-IP (cpm)+[$^3$H]-inositol (cpm)). Each value was normalized using the basal value (no thrombin stimulation) obtained in pcDNA transfected cells. See FIG. 14. The results presented are the normalized mean ±SEM of at least 3 independent experiments performed in triplicate. The ** symbol indicated p<0.005. Results indicate that addition of thrombin increased IP production in control cells (pcDNA, pcDNA-GiR). Cells transfected with PcDNA-Gq had no thrombin-mediated IP production increase, while cells transfected with pcDNA-Gi had a normal response. These results indicate that the Gq C-terminal peptide can inhibit thrombin-mediated IP increases in HMEC.

EXAMPLE 26

Interfacial G Protein Peptide Inhibition of Thrombin-Induced PI Hydrolysis and Intracellular Ca$^{++}$ Rise.

To determine whether expression of the Gαq C-terminal minigene could affect intracellular [Ca$^{++}$]$_i$ levels, HMEC were transfected with empty vector (pcDNA), pcDNA-Gαi, pcDNA-Gαq, or pcDNA-GαiR minigene DNA (1 μg). Transfected cells were seeded at a low confluency on coverslips in a 24-well plate 48 hours post transfection. The cells were allowed to adhere for two hours. The medium was aspirated and each coverslip was incubated with 10 μM Oregon Green 488 BAPTA-1 acetoxymethyl ester (a calcium-sensitive dye) and 0.1% (v/v) Pluronic F-127 and allowed to incubate for 20–30 minutes at 37° C., then rinsed twice with wash buffer. Basal conditions were established before addition of thrombin (~70 mM) in $Ca^{++}$ buffer. Recordings were made every 10 seconds and continued for 170 seconds after stimulation with thrombin. Images were quantitated using NIH Image. Data from at least 70 individually recorded cells were used to calculate the changes in fluorescence (y-axis). See FIG. 15A, which presents fluorescence in ($[Ca^{++}]$; level) increase 30 seconds after thrombin addition. Each bar in FIG. 15A represents the mean $((F_S-F_B/F_B-1)\pm SEM$ of over 70 individually recorded cells. The ** symbol indicates p<0.005. FIG. 15B shows the kinetics of [Ca++]; fluorescence changes after cell stimulation with thrombin. Data presented are the mean $((F_S-F_B/F_B-1)\pm SEM$ at each recording point for cells transfected with pcDNA or pcDNA-Gαq. The arrow indicate the time thrombin was added. Each time point represents over 100 individually recorded cells.

Figure 15:
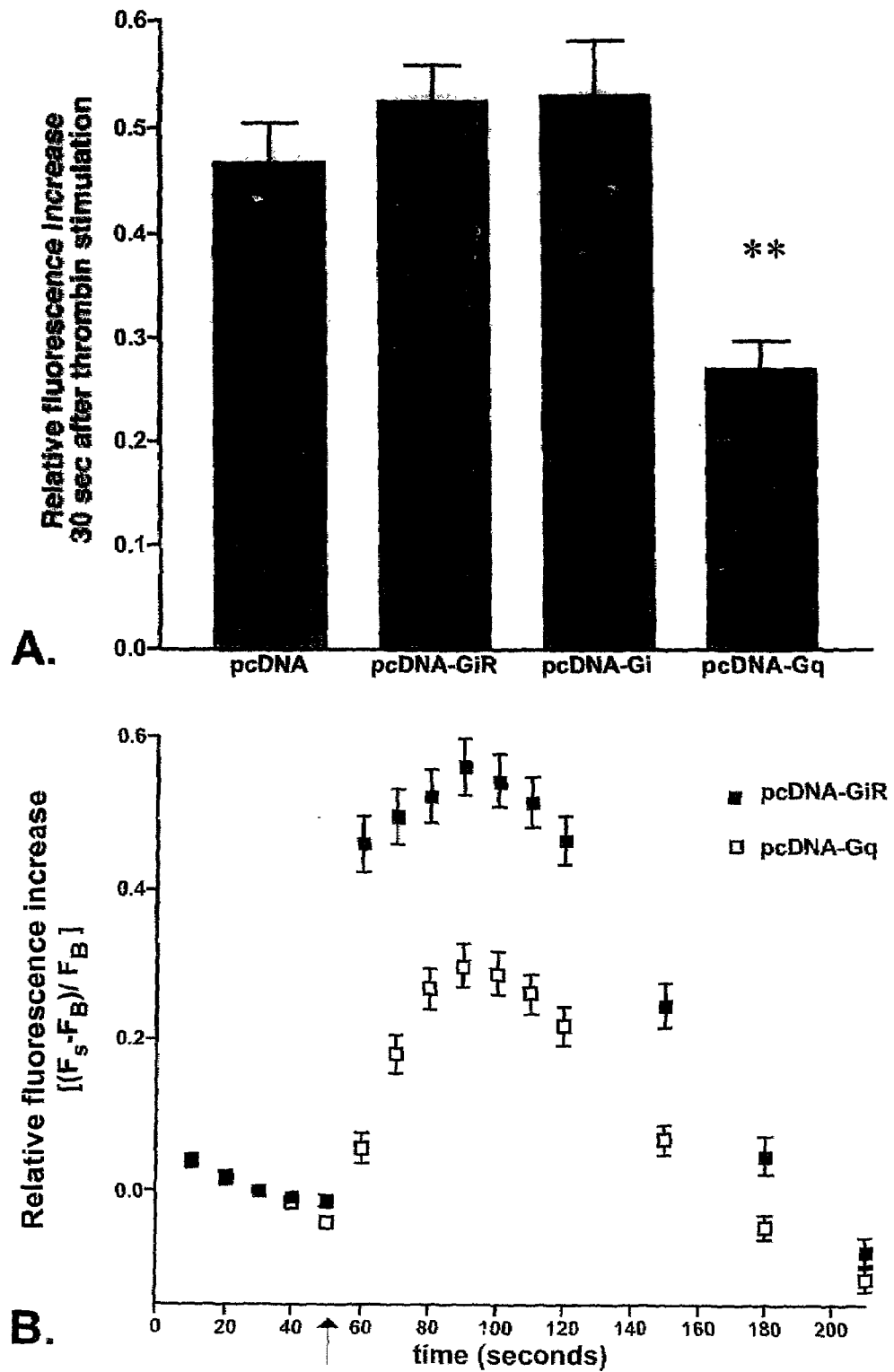
FIG. 15 presents data showing GPCR binding peptide inhibition of intracellular calcium concentration increases.
Figure 16:
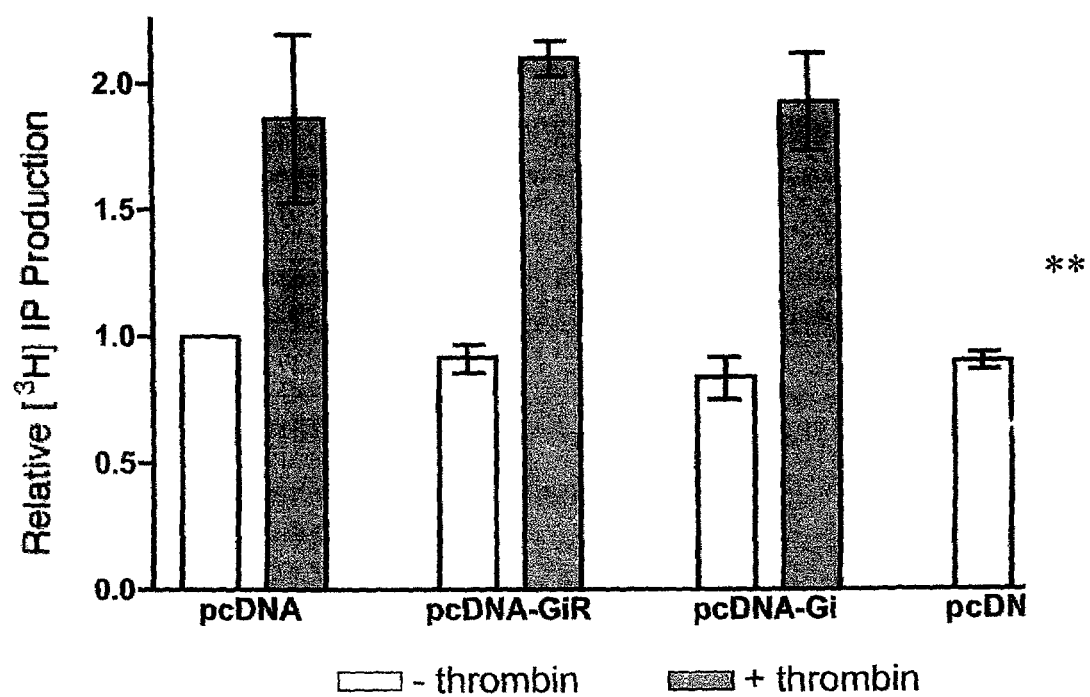
FIG. 16 presents data showing GPCR binding peptide inhibition of thrombin-induced phosphoinositol (P1) hydrolysis.

As shown in FIG. 15, following cell activation by addition of thrombin there was a transient increase in intracellular $[Ca^{2+}]$ levels. Thirty seconds after the addition of thrombin, cells transfected with pcDNA-Gαq had a calcium response that was 44% decreased as compared to cells transfected with pcDNA (FIG. 15A). pcDNA-Gαq transfected cells had a 45% decrease compared to those transfected with pcDNA when all time points measured after thrombin stimulation are averaged (FIG. 15B). This decrease appears to be specific as cells transfected with pcDNA-Gαi or pcDNA-Gαir did not have any effect on thrombin stimulated intracellular $[Ca^{2+}]$ levels. Thus, cells expressing the Gαq C-terminal peptide appear to be inhibited in their ability to stimulate intracellular $[Ca^{2+}]$ levels following activation with thrombin, indicating a specific block of this downstream mediator by expression of Gαq.

pcDNA, pcDNA-GiR, pcDNA-Gi, pcDNA-Gq, or pcDNA-Gs minigene constructs were transfected into HMEC and used to assay inositol phosphate (IP) accumulation 48 hours later. After 24 hours, cells were reseeded onto 24-well plates and labeled with [³H]-myoinositol (2 μCi/ml). After 48 hours, cells were rinsed, and incubated with or without thrombin (10 nM) for 10 minutes. Total IP accumulation was assayed as described above using DOWEX™ columns to separate [³H] IP. The relative amount of [³H] IP generated was calculated as follows: ([³H] IP (cpm)/[³H] IP (cpm)+[³H] inositol (cpm)). Each value was normalized by the basal value (no thrombin stimulation) obtained in pcDNA transfected cells. See FIG. 16. The results presented are the normalized mean ±SEM of at least three independent experiments performed in triplicate. The ** symbol indicated p<0.005.

EXAMPLE 27

Prevention of Thrombin-Induced MAPK Activity by High Affinity GPCR-binding Peptides.

Figure 17:
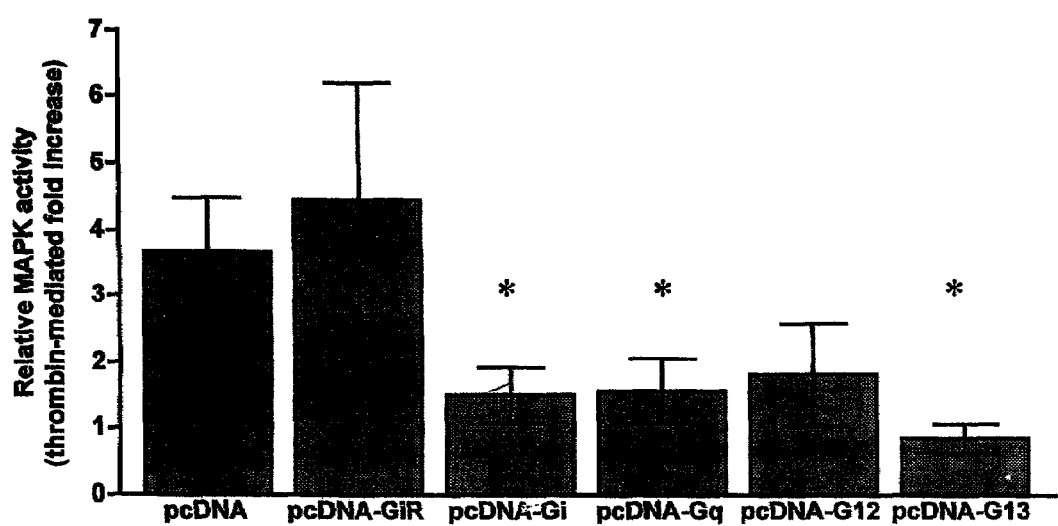
FIG. 17 is a bar graph indicating relative thrombin-mediated fold increases of MAPK activity in cells expressing GPCR-binding peptides.

Hemagglutanin (HA)-MAPK (1×10⁵/mL was co-transfected into HMEC with the pcDNA, pcDNA-Gαi, pcDNA-Gαq or pcDNA-GαiR minigene constructs using the methods described in Example 21. After 30 hours, cells were serum-starved for 18 hours and then treated with 10 nM thrombin for 20 minutes. Cells were then lysed with RIPA buffer (50 mM Tris, pH 7.5, 150 mM NaCl, 2 mM EDTA, 1% Triton X-100, 0.5% deoxycholate, 0.1% SDS, 10% glycerol, 10 μg/mL aprotinin and 10 μg/mL leupeptin) and HA-MAPK protein immunoprecipitated using 12CA5 antibody (Roche Molecular Biochemicals; Indianapolis, Ind.) (one hour, 4° C.) and Protein A sepharose beads (three hours, 4° C.). Immune complexes were washed three times in RIPA buffer. Kinase activity in the immunoprecipitates was measured using maltose binding protein (MBP) substrate and a kinase assay kit (Upstate Biotechnology, Inc., Lake Placid, N.Y.). MAPK activity (nM/min/mg) was obtained for each, and the relative increase of MAPK activity (thrombin-mediated fold increase) was calculated as follows: (stimulated activity (nM/min/mg)–basal activity (nM/min/mg))/basal activity (nM/min/mg). Results are presented as the mean ±SEM of at least three independent experiments in FIG. 17. A * symbol indicates p<0.05.

Addition of 10 nM thrombin resulted in a 3.66 fold increase in HA-MAPK activity in cells transfected with the pcDNA control vector. Similarly, cells transfected with pCDNA-GiR had an essentially equivalent increase in thrombin mediated MAPK activity with (4.46 fold increase). However, endothelial cells transfected with a minigene construct encoding the Gαi, Gαq, Gα12 or Gα13 GPCR binding peptides showed a significant decrease in thrombin-mediated HA-MAPK activity (59%, 57%, 50% and 77%, respectively) compared to cells transfected with pcDNA.

EXAMPLE 28

Reduction of Thrombin-Induced Transendothelial Electrical Resistance.

Figure 18:
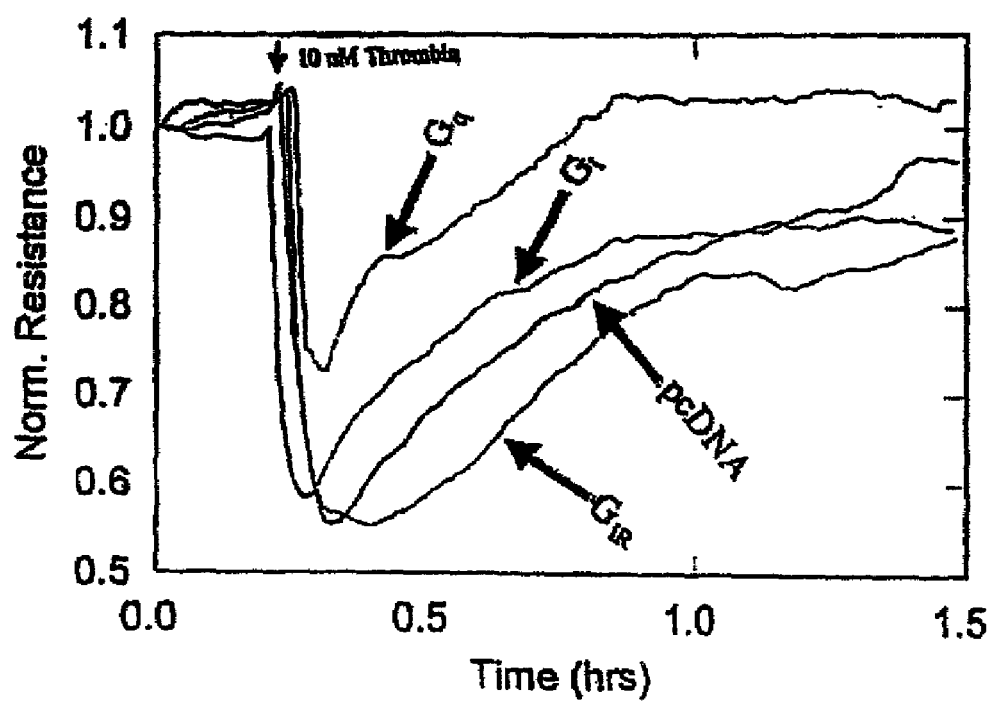
FIG. 18 shows reduction of thrombin-induced transendothelial electrical resistance in cells expressing Gαq, Gαi, GαiR or empty vector.

Transendothelial electrical resistance (TEER) was measured by passing an alternating current (50 μA; 2 pulses every minute) across monolayers of HMEC expressing Gαq, Gαi, GαiR or no minigene construct. Basal TEER did not change significantly with minigene transfection. Upon addition of 10 nM thrombin, however, there was a decrease in the TEER of cells expressing the Gαq minigene compared to non-transfected cells in the presence of 10 nM thrombin. See FIG. 18 (representative of multiple experiments). The decrease in transendothelial electrical resistance in response to thrombin was significantly reduced in endothelial cells transfected with the minigene for the carboxyl terminus of Gαq, while there was no effect in cells transfected with Gαi, GαiR, or empty vector. These results suggested that Gαq is partially responsible for the effects of thrombin on endothelial cell shape changes.

EXAMPLE 29

Inhibition of Thrombin-Mediated Stress Fiber Formation.

HMEC cells were transfected with pcDNA, pcDNA-Gα12 or pcDNA-Gα13 minigene constructs 1 μg each/100 mm dish. As a marker for transfected cells, the pGreenLantern-1 plasmid, containing the gene for green fluorescent protein (GFP) was co-transfected together with minigene constructs. After 48 hours, cells were serum starved for 18 hours and treated with 10 nM thrombin for 20 minutes. After exposure to thrombin, the cells were fixed with 4% paraformaldehyde, permeabilized with 0.1% Triton X-100 and stained for F-actin with 1 mM rhodamine-phalloidin for 30 minutes. Cells were extensively washed, mounted using Vectashield™ antifade mounting medium (Vector Laboratories, Inc.). Cells were observed with an inverted microscope (Diaphot 200, Nikon, Inc.) equipped for both differential interference contrast microscopy and epifluorescence observation using a 60× oil-immersion objective. Fluorescence and DIC images were recorded for each cell field with a cooled, integrating CCD array camera (Imagepoint, Photometrix, Ltd.) connected to the microscope. See FIG. 19 for fluorescence images showing inhibition of thrombin-mediated stress fiber formation by Gα12 and Gα13 peptides.

Figure 19:
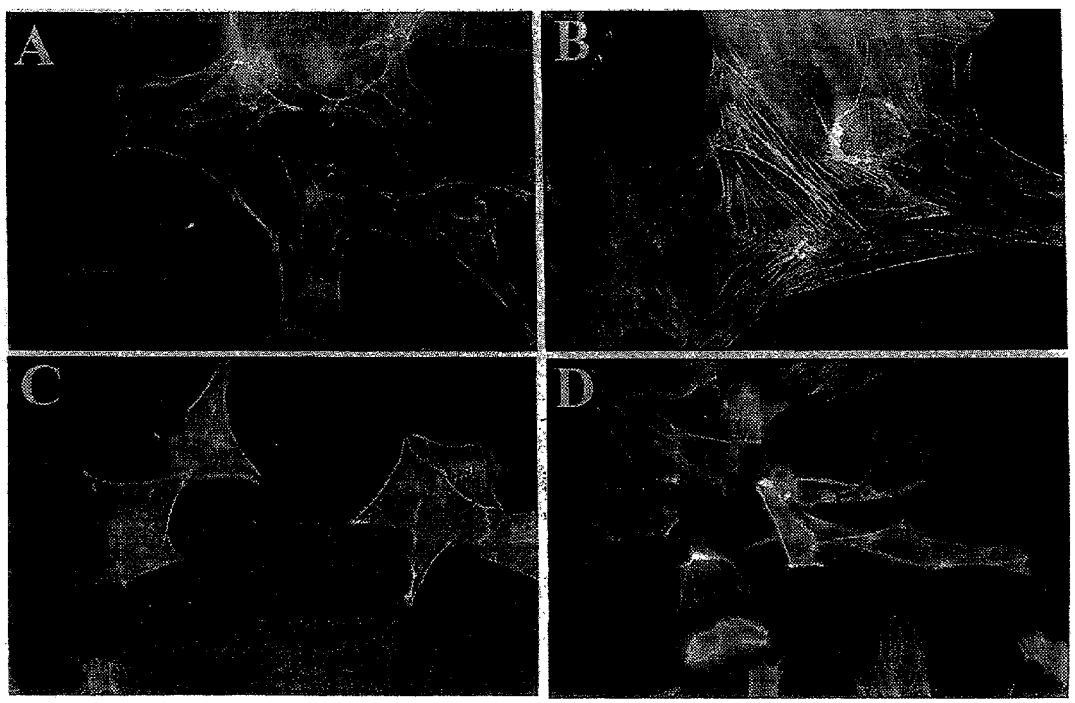
FIG. 19 is a series of photographs of cells stained for F-actin, showing the inhibition of stress fiber formation after exposure to thrombin in cells expressing pcDNA-G12 or pcDNA-G13 minigene construct.

Serum starved cells transfected with pcDNA exhibited a thin cortical F-actin rim at their margins, and contained few stress fibers (FIG. 19, panel A). Those present were inconspicuous and in apparently random orientation. For HMEC transfected with pcDNA after a 20-minute exposure to thrombin actin had reorganized into prominent stress fibers, typically arranged in a parallel pattern along the longitudinal axis of the cell (FIG. 19, panel B). A very different pattern was observed for cells transfected with pcDNA-Gα12 (FIG. 19, panel C) or pcDNA-Gα13 (FIG. 19, panel D) minigenes after exposure to thrombin. In both pcDNA-Gα12 and pcDNA-Gα13 transfected cells, thrombin stimulation did not result in the appearance of stress fibers. In cells transfected with pcDNA-Gα13, the peripheral actin rim appears thicker and more linear, providing a clear outline of cell-cell junctions. Thus, in agreement with earlier reports, thrombin induced rapid stress fiber formation in endothelial cells. Transfection of either pcDNA-Gα12 or pcDNA-Gα13 minigenes resulted in cells that no longer showed thrombin-induced stress fiber formation. Given that stress fiber formation is dependent on the small GTPase Rho, these results concur with other findings that Gα12 and Gα13 are intimately linked to Rho signaling and demonstrates the ability of GPCR binding peptides to specifically block this G protein pathway when expressed intracellularly.

EXAMPLE 30

Inhibition of G Protein Activity by GPCR Binding Peptides in Single Intact Cells.

Human embryonic kidney (HEK) 293 cells, which stably express the $M_2$ mACR (~400 fmol receptor/mg protein), were grown in DMEM (Gibco) supplemented with 10% fetal bovine serum (Gibco), streptomycin/penicillin (100 U each; Gibco) and G418 (500 mg/L; Gibco). Cells were grown under 10% $CO_2$ at 37° C. In all transfections for electrophysiological studies, the CD8 reporter gene system was used to visualize transfected cells using Dynabeads™ coated with anti-CD8-antibodies (Dynal). The following amounts of cDNA were used to transfect the cells: pCl-GIRK1 (rat)—1 μg; πH3-CD* (human)—1 μg; pcDNA3.1, pcDNA-Gαi, pcDNA-GαiR, pcDNA-Gαq, or pcDNA-Gαs—4 μg. Thus, typically the total amount of cDNA used for transfecting one 10 cm disk was 7 μg. The cDNAs for GIRK1 and GIRK4 were gifts from F. Lesage and M. Lazdunski (Nice, France). A standard calcium phosphate procedure was used for transient transfection of HEK cells according to the methods of Schenborn et al., *Meth. Mol. Biol.* 130:135–145, 2000. All assays were performed 48–72 hours post transfection.

Whole cell currents were recorded from stably $M_2$ mAChR-expressing HEK 293 cells that had been transiently transfected with cDNA for GIRK1, GIRK4 and either pcDNA-Gαi, pcDNA-Gαs, or pcDNA-Gαq. For the measurement of inwardly rectifying K+ currents, whole cell currents were recorded using an extracellular solution contained 120 mM NaCl; 20 mM KCl; 2 mM $CaCl_2$; 1 mM $MgCl_2$; and 10 mM Hepes-NaOH, pH 7.4. The solution for filling the patch pipettes was composed of 100 mM potassium glutamate; 40 mM KCl; 5 mM MgATP; 10 mM Hepes-KOH, pH 7.4; 5 mM NaCl; 2 mM EGTA; 1 mM $MgCl_2$; and 0.01 mM GTP. Membrane currents were recorded under voltage clamp, using conventional whole cell patch techniques. See Bunemann et al., *J. Physiol.* 489:701–777, 1995 and Bunemann et al., *J. Physiol.* 482: 81–89, 1995, the disclosures of which are hereby incorporated by reference. To minimize variations due to different transfections or culture conditions, control experiments (transfection with pcDNA-GαiR) were done in parallel. Patch-pipettes were fabricated from borosilicate glass capillaries, (GF-150-10, Warner Instrument Corp.) using a horizontal puller (P-95 Fleming & Poulsen). The DC resistance of the filled pipettes ranged from 3–6 MΩ.

Membrane currents were recorded using a patch-clamp amplifier (Axopatch 200, Axon Instruments). Signals are analog filtered using a lowpass Bessel filter (1–3 kHz corner frequency). Data were digitally stored using an IBM compatible PC equipped with a hardware/software package (ISO2 by MFK, Frankfurt/Main, Germany) for voltage control, data acquisition and data evaluation. To measure K+ currents in the inward direction, the potassium equilibrium potential was set to about −50 mV and the holding potential was −90 mV. Agonist-induced currents were evoked by application of acetylcholine (ACh; 1 μM) using a solenoid operated superfusion device which allowed for solution exchange within 300 msec. Linear voltage ramps (from −120 mV to +60 mV within 500 ms) were applied every 10 sec. By subtracting non-agonist dependent currents, the current voltage properties of the agonist induced currents could be resolved. To exclude experiments in which currents were recorded from cells that may not have expressed the functional channel, only those cells that exhibited a basal non-agonist dependent $Ba^{2+}$ (200 μM) sensitive inwardly rectifying current were used for analysis. For analysis of the data, the maximal current density (peak amplitude) of ACh-induced inwardly rectifying K+ currents was measured at −80 mV and compared.

Figure 20:
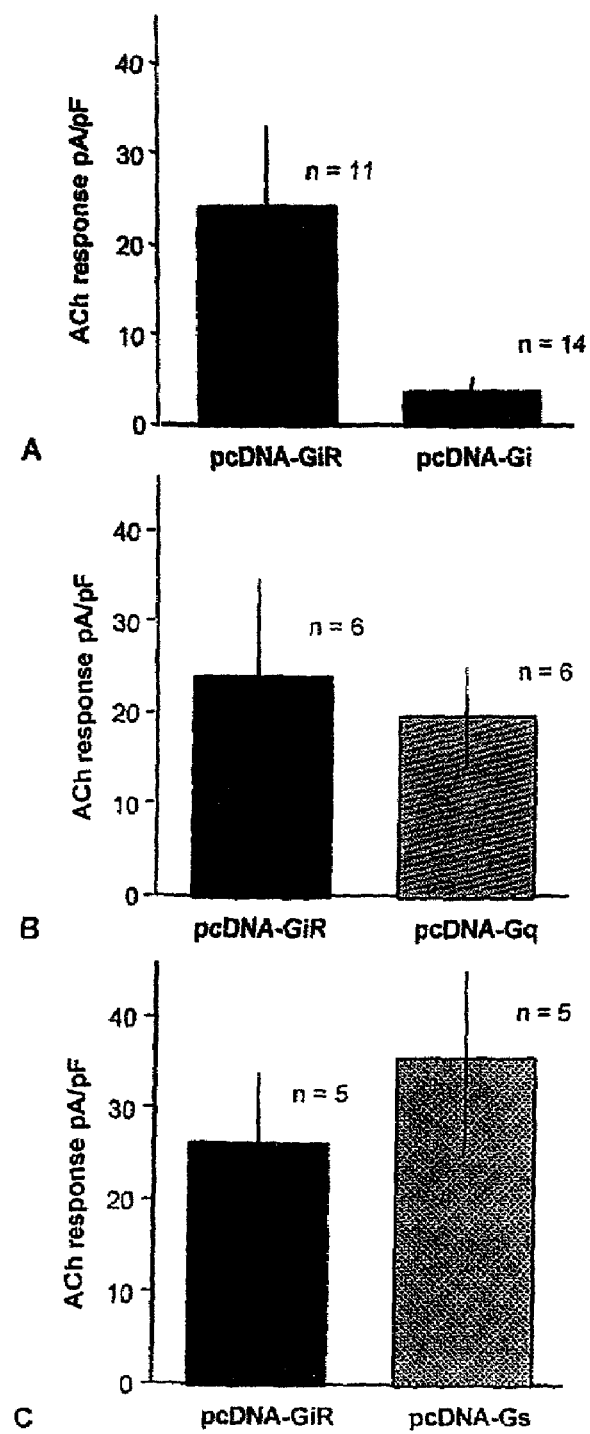
FIG. 20 presents data showing blockade of $M_2$ mAChR response by Gαi peptide expression.

Superfusion of HEK 293 cells transiently transfected with GIRK1/GIRK4 and either pcDNA-$G_i$ or pcDNA-$G_i$R DNA with 1 μM ACh revealed that cells transfected with pcDNA-$Gα_i$ DNA have a dramatically impaired response to the $M_2$ mAChR agonist. See FIG. 20, which summarizes data showing the maximum amplitude of ACh evoked currents for the different transfection conditions. The maximum current evoked by ACh was 3.7+/−1.5 pA/pF (n=14) in cells transfected with pcDNA-$G_i$, compared to 24.1+/−8.8 pA/pF (n=11) in cells transfected with pcDNA-$G_1$R. This indicates that the Gαi minigene construct completely blocked the agonist mediated $M_2$ mAChR GIRK1/GIRK4 response while the control minigene construct (pcDNA-GiR) had no effect. Compare FIG. 20A to FIGS. 20B and 20C. Cells transfected with minigene constructs encoding Gα carboxyl termini for Gαq or Gαs pcDNA-Gαq or pcDNA-Gαs (FIG. 20) were not significantly different than those of cells transfected with the control vectors. These findings confirm the specificity of the inhibition of $M_2$ mAChR-activated G protein-coupled inwardly rectifying K+ current responses by expression of the Gαi minigene.

EXAMPLE 31

Selective G Protein Signaling Inhibition in Human Microvascular Endothelial Cells.

Different measures of G-protein signaling final actions were assayed in human microvascular endothelial cells (HMEC) which natively express the thrombin receptor, PAR1. The cells were seeded onto 6-well plates at $1 \times 10^5$ cells/well and transiently transfected after 24 hours with minigene constructs containing Gα carboxyl terminal peptides (pcDNA, pcDNA-Gαi, or pcDNA-GαiR; 1 μg per well) using Effectene (Qiagen) according to the manufacturer's protocol. After 24 hours, the cells were labeled with 3 μCi/ml [$^3$H]-adenine for 30 minutes at 37° C. After another 24 hours, the cells were washed with serum-free medium containing 1 mM isobutyl-methyl xanthine. To stimulate cAMP accumulation, cells were treated with 1 μM isoproterenol for 30 minutes at 37° C. To see the inhibitory effects of thrombin on cAMP accumulation, cells were pretreated with thrombin (50 nM) for 15 minutes prior to addition of isoproterenol. The reactions were terminated by aspiration of media followed by addition of ice-cold 5% trichloroacetic acid.

Figure 21:
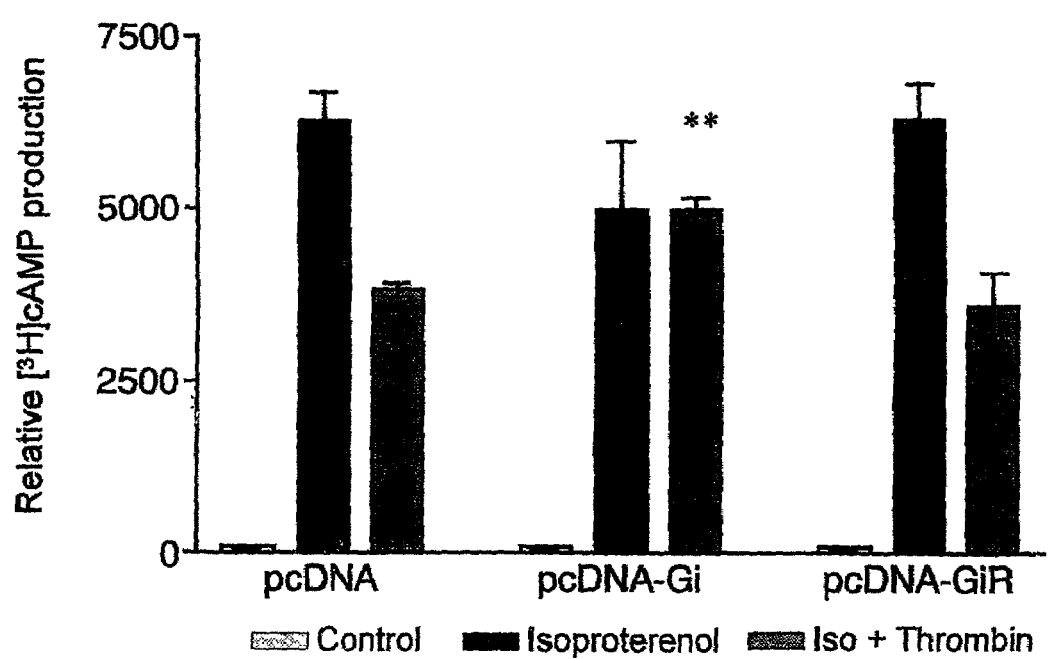
FIG. 21 demonstrates selective G protein mediated adenylyl cyclase inhibition in cells expressing minigene constructs containing Gα carboxyl terminal peptide inserts.

Results are provided in FIG. 21 as (cAMP/cAMP+ATP)× 1000. Three separate experiments were done in duplicate. The ** symbol indicates p<0.005. Basal cAMP levels were essentially equivalent for all conditions tested. Endothelial cells stimulated with isoproterenol to activate P-adrenergic receptors increase their cAMP levels through the Gs pathway. Cells transfected with pcDNA, pcDNA-Gαi, or pcDNA-GαiR showed little difference with 82, 64, and 77 fold increases in isoproterenol-mediated cAMP accumulation, respectively. When the endothelial cells were pre-incubated with thrombin prior to addition of isoproterenol, a decrease in cAMP levels was observed due to thrombin activation of the Gi pathway. Endothelial cells transfected with pcDNA and pre-incubated with thrombin showed a 39% decrease in cAMP level over cells stimulated with only isoproterenol. Similarly, cells transfected with pcDNA-GαiR and pre-incubated with thrombin showed had a 43% decrease over cells stimulated with only isoproterenol. However, cells transfected with pcDNA-Gαi and pre-incubated with thrombin had only a 0.1% decrease in cAMP levels as compared to cells stimulated with only isoproterenol. Thus, cells expressing the Gαi C-terminal peptide appear to be unable to inhibit adenyl cyclase following activation with thrombin, indicating that thrombin-mediated Gi signaling was specifically blocked by expression of the pcDNA-Gαi minigene.

EXAMPLE 32

Screening Method to Identify Inverse Agonists.

Urea-washed rod outer segment membrane fragments containing rhodopsin receptor are immobilized onto microtiter wells and blocked as described in Example 7. The receptor is light-activated. Labeled native Gαt carboxyl terminal peptide is added to each well and allowed to shake gently for one hour at 4° C. The wells are washed to remove unbound peptide. Crude bacterial lysates (labeled) from a Gαt carboxyl terminal peptide prepared according to the methods described in Example 7 (200 μL) are added to each well and incubated with shaking for one hour at 4° C.

The wells then are washed to remove unbound label. The supernatants or well-bound labels are quantitated by ELISA to detect dissociation of labeled native peptide from the receptor after incubation with library peptides compared to control well incubated in the absence of library peptides.

EXAMPLE 33

Small Molecule Library Screening Method.

Small molecule libraries are screened for inhibition of GPCR-mediated G protein signaling as follows. PAR1 thrombin receptor prepared from insect cells according to Example 2 are immobilized onto microtiter wells, blocked and washed according to the methods described in Example 14. A small molecule library purchased from Chem Div (San Diego, Calif.) are added simultaneously with MBP-peptide fusion protein (0.1–1000 nM) in a 96- or 384-well plate and allowed to shake for one hour at 4° C. Initial screens are performed with the small molecules at about 1–1000 pM. The wells are washed four times in cold PBS containing 0.05% Tween 20™ and 1 mM maltose. The amount of maltose binding protein adhering to the wells is quantitated with anti-MBP antibodies as described in Example 14, versus control wells incubated without library compounds.

The invention claimed is:

1. A two-screen method of assaying intracellular G protein coupled receptor (GPCR) signaling inhibition, which comprises:
   (a) providing a first library comprising peptide members, wherein said library is a biased peptide library and wherein the primary sequences of said members are obtained from a native G protein Gα subunit which consists of SEQ ID NO:38;
   (b) screening said peptide first library members for binding to said G protein binding domain of said GPCR, wherein said screening comprises a competitive binding assay performed in the presence of a first competitive peptide which consisting of SEQ ID NO:38, to identify high-affinity peptide first library members that bind to said GPCR G protein binding domain with higher affinity than that of said first competitive peptide;
   (c) selecting a high-affinity peptide first library member identified in (b);
   (d) providing a second library of member compounds;
   (e) screening said second library member compounds for binding to said GPCR G protein binding domain, wherein said screening is a competitive binding assay performed in the presence of a second competitive peptide which consists of said selected high affinity peptide first library member of (c), to determine whether a second library member compound binds to said GPCR G protein binding domain with equal or higher affinity than that of said second competitive peptide.

2. A method of claim 1, wherein said screening of (b) further comprises an additional binding assay.

3. A method of claim 1, wherein said peptide first library members are labeled to provide a signal to detect binding.

4. A method of claim 1, wherein binding of a first library member to said GPCR G protein binding domain is detected by contacting said GPCR with a ligand that activates said GPCR and measuring activation of said GPCR in the presence and absence of said first library member.

5. A method of claim 1, wherein said first library is a combinatorial peptide library.

* * * * *

UNITED STATES PATENT AND TRADEMARK OFFICE
CERTIFICATE OF CORRECTION

PATENT NO. : 7,208,279 B2
APPLICATION NO. : 09/852910
DATED : April 24, 2007
INVENTOR(S) : Gilchrist et al.

It is certified that error appears in the above-identified patent and that said Letters Patent is hereby corrected as shown below:

On the Title Page item 75

Inventors: "Heidi M. Hamm" should be -- Heidi E. Hamm --

In Other Publications item 56

Reference No. 6, page 1 - West, et al. "Pertussie" should be -- Pertussis --

Reference No. 20, page 2 - Gilchrist, et al. insert -- " -- before "A dominant"

Reference No. 20, page 2 - Gilchrist, et al. "Vivo*," should be -- Vivo,"--

Reference No. 36, page 2 - Cull, et al., "fo" should be -- of --

Reference No. 50, page 2 - Szardenings, et al. "MC," should be -- $MC_1$ --

Reference No. 73, Costa and Herz, "σ" should be -- δ --

Reference No. 73, Costa and Herz, "proc." should be -- Proc. --

Reference No. 83, Leeb-Lundberg, et al. "Antonists" should be -- Antagonists --

Reference No. 93, Vassart, et al. "Redeptor $^{\alpha}$" should be -- Receptor $^{\alpha}$ --

In the Specification

Col. 2, line 65, "241 -" should be -- 241: --

Col. 3, line 32, insert -- ( -- before "Nussenzveig"

Col. 3, line 34, insert -- ) -- after "1995"

Col. 3, line 38, "finding" should be -- findings --

Col. 4, line 24, delete "i" before "Nature"

Col. 4, line 30, "GαIF" should be -- GαOIF --

Col. 4, line 35, "241-832-5" should be -- 241:832-5 --

UNITED STATES PATENT AND TRADEMARK OFFICE
CERTIFICATE OF CORRECTION

PATENT NO. : 7,208,279 B2
APPLICATION NO. : 09/852910
DATED : April 24, 2007
INVENTOR(S) : Gilchrist et al.

It is certified that error appears in the above-identified patent and that said Letters Patent is hereby corrected as shown below:

In the Specification (cont'd)

Col. 4, line 36, "273-14912-9" should be -- 273:14912-9 --

Col. 6, line 57, "[CA$^{++]}$" should be -- [CA$^{++}$] --

Col. 8, line 60, "hundred" should be -- hundreds --

Col. 14, line 4, insert -- . -- after "residues"

Col. 14, line 5, "the" should be -- The --

Col. 20, line 23, "-8°C." should be -- -80°C. --

Col. 20, line 34, "$10^{6-10}{}_9$ i.u./ml." should be -- $10^6$-$10^9$ i.u./mL. --

Col. 22, line 18, "Gαtq" should be -- Gαq --

Col. 22, line 53, "*Pham.*" should be -- *Pharm.* --

Col. 22, line 55, "*Phar.*" should be -- *Pharm.* --

Col. 25, line 21, delete second instance of ")"

Col. 26, line 42, "190" should be -- # --

Col. 27, line 12, "kg" should be -- xg --

Col. 27, line 35, insert -- . -- after "used"

Col. 27, line 36, "the" should be -- The --

Col. 27, line 44, "homogenation/ washing" should be
-- homogenation/washing --

Col. 28, line 17, delete ")" after "μL"

Col. 28, line 36, "Mg$_2$SO$_4$.7H$_2$O" should be -- Mg$_2$SO$_4$•7H$_2$O --

UNITED STATES PATENT AND TRADEMARK OFFICE
CERTIFICATE OF CORRECTION

PATENT NO. : 7,208,279 B2
APPLICATION NO. : 09/852910
DATED : April 24, 2007
INVENTOR(S) : Gilchrist et al.

It is certified that error appears in the above-identified patent and that said Letters Patent is hereby corrected as shown below:

In the Specification (cont'd)

Col. 30, Table IX, line 62: Library Sequence 17 (SEQ ID NO:139) should read -- M R E S L K D C G L F --

Col. 31, line 32, "ed" should be -- peptide used --

Col. 31, Table X, line 13: Library Sequence 17 (SEQ ID NO:146) should read -- I R N N L K R Y G M F --

Please replace Table XV with the following table:

Table XV
Rhodopsin screened with Gt library

| Competitor | | SEQ ID NO: | ELISA |
|---|---|---|---|
|  | IRENLKDCGLF | 124 |  |
| L33 | IVEILEDCGLF | 205 | 1.007 |
| L4 | MLDNLKACGLF | 206 | .908 |
| L3 | ILENLKDCGLF | 207 | .839 |
| L14 | LRENLKDCGLL | 208 | .833 |
| L38 | LLDILKDCGLF | 209 | .823 |
| L15 | VRDILKDCGLF | 210 | .621 |
| L34 | ILESLNECGLF | 211 | .603 |
| L17 | ILQNLKDCGLF | 212 | .600 |
| L7 | MLDNLKDCGLF | 213 | .525 |
| L10 | IHDRLKDCGLF | 214 | .506 |
| L20 | IRGSLKDCGLF | 135 | .423 |
| L6 | ICENLKDCGLF | 215 | .342 |
| L8 | IVKNLEDCGLF | 216 | .257 |
| L13 | ISKNLRDCGLL | 217 | .187 |
| L10 | IRDNLKDCGLF | 218 | .162 |

UNITED STATES PATENT AND TRADEMARK OFFICE
CERTIFICATE OF CORRECTION

PATENT NO. : 7,208,279 B2
APPLICATION NO. : 09/852910
DATED : April 24, 2007
INVENTOR(S) : Gilchrist et al.

It is certified that error appears in the above-identified patent and that said Letters Patent is hereby corrected as shown below:

In the Specification (cont'd)

Please replace Table XVI with the following:

Table XVI
Peptides Identified with CHO EXPRESSED PAR1

| Gt library (IRENLKDCGLF; SEQ ID NO:124) | | G12 library (LQENLKDIMLQ; SEQ ID NO:38) | | G13 library (LQDNLKQLMLQ; SEQ ID NO:233) | |
|---|---|---|---|---|---|
| IREFLTDCGLF | 219 | LQENLKEMMLQ | 225 | LQDNLRHLMLQ | 234 |
| IRLDLKDVSLF | 220 | LEENLKYRMLD | 226 | LQDKINHLMLQ | 235 |
| ICERLNDCGLC | 221 | LQEDLKGMTLQ | 227 | LQANRKLGMLQ | 236 |
| PRDNTKVRGLF | 222 | LQETMKDQSLQ | 228 | LIVKVKQLIWQ | 237 |
| FWGNLQDSGLF | 223 | PQVNLKSIMRQ | 229 | MRAKLNNLMLE | 238 |
| RRGNGKDCRHF | 224 | WQHKLSEVMLQ | 230 | LQDNLRHLIQ | 239 |
| | | LKEHLMERMLQ | 231 | LQDNRNQLLF | 240 |
| | | LLGMLEPLMEQ | 232 | | |

Col. 36, line 64, "separated" should be -- separated --

Col. 37, line 1, between "overnight" and "prepared" insert -- and DNA was --

Col. 39, line 36, "SF9" should be -- Sf9 --

Col. 39, line 55, "Gll" should be -- G11 --

Col. 40, line 51, "manufacture's" should be -- manufacturer's --

Col. 41, line 24, "protein a" should be -- protein α --

Col. 41, line 39, "Harpor" should be -- Harbor --

Col. 42, line 46, "[3H]" should be -- [$^{3}$H] --

Col. 43, line 64, insert -- ) -- after "mL"

Col. 44, line 23, "pCDNA-GiR" should be -- pcDNA-GiR --

Col. 45, line 65 "K+" should be -- K$^{+}$ --

UNITED STATES PATENT AND TRADEMARK OFFICE
CERTIFICATE OF CORRECTION

PATENT NO.        : 7,208,279 B2
APPLICATION NO.   : 09/852910
DATED             : April 24, 2007
INVENTOR(S)       : Gilchrist et al.

It is certified that error appears in the above-identified patent and that said Letters Patent is hereby corrected as shown below:

<u>In the Specification (cont'd)</u>

Col. 46, line 62 "pCDNA-Gas" should be -- pcDNA-Gas --

Col. 47, line 28, "P-adrenergic" should be -- β-adrenergic --

<u>In the Claims</u>

Col. 137, line 22, "consisting" should be -- consists --

Signed and Sealed this

Twenty-seventh Day of November, 2007

JON W. DUDAS
*Director of the United States Patent and Trademark Office*

SEQUENCE LISTING

<160> NUMBER OF SEQ ID NOS: 271

<210> SEQ ID NO 1
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (1)..(4)
<223> OTHER INFORMATION: MBP-G11

<400> SEQUENCE: 1

Xaa Xaa Xaa Xaa
1

<210> SEQ ID NO 2
<211> LENGTH: 11
<212> TYPE: PRT
<213> ORGANISM: Homo sapiens

<400> SEQUENCE: 2

Leu Gln Leu Asn Leu Lys Glu Tyr Asn Leu Val
1               5                   10

<210> SEQ ID NO 3
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-13

<400> SEQUENCE: 3

Val Arg Pro Ser
1

<210> SEQ ID NO 4
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 4

Leu Gln Leu Asn Arg Asn Glu Tyr Tyr Leu Val
1               5                   10

<210> SEQ ID NO 5
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-23

<400> SEQUENCE: 5

Leu Ser Arg Ser
1

<210> SEQ ID NO 6
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 6

Leu Gln Gln Lys Leu Lys Glu Tyr Ser Leu Val
1               5                   10

<210> SEQ ID NO 7
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-33

<400> SEQUENCE: 7

```
Leu Ser Thr Asn
1

<210> SEQ ID NO 8
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 8

Leu His Leu Asn Leu Lys Glu Tyr Asn Leu Val
1               5                   10

<210> SEQ ID NO 9
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-34

<400> SEQUENCE: 9

Leu Pro Gln Met
1

<210> SEQ ID NO 10
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 10

Gln Arg Leu Asn Val Gly Glu Tyr Asn Leu Val
1               5                   10

<210> SEQ ID NO 11
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-45

<400> SEQUENCE: 11

Ser Arg His Thr
1

<210> SEQ ID NO 12
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 12

Leu Arg Leu Asn Gly Lys Glu Leu Asn Leu Val
1               5                   10

<210> SEQ ID NO 13
<211> LENGTH: 11
<212> TYPE: PRT
<213> ORGANISM: Homo sapiens
```

```
<400> SEQUENCE: 13

Gln Arg Met His Leu Arg Gln Tyr Glu Leu Leu
1               5                   10

<210> SEQ ID NO 14
<211> LENGTH: 67
<212> TYPE: DNA
<213> ORGANISM: Artificial Sequence
<220> FEATURE:
<223> OTHER INFORMATION: G alpha t library construct
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 14
gaggtggtnn knnknnknnk attcgtgaaa acttaaaaga ttgtggtcgt ttctaactaa     60
gtaaagc                                                              67

<210> SEQ ID NO 15
<211> LENGTH: 11
<212> TYPE: PRT
<213> ORGANISM: Homo sapiens

<400> SEQUENCE: 15

Ile Lys Glu Asn Leu Lys Asp Cys Gly Leu Phe
1               5                   10

<210> SEQ ID NO 16
<211> LENGTH: 33
<212> TYPE: DNA
<213> ORGANISM: Homo sapiens

<400> SEQUENCE: 16
atcaaggaga acctgaaaga ctgcggcctc ttc                                 33

<210> SEQ ID NO 17
<211> LENGTH: 11
<212> TYPE: PRT
<213> ORGANISM: Homo sapiens

<400> SEQUENCE: 17

Ile Lys Asn Asn Leu Lys Asp Cys Gly Leu Phe
1               5                   10

<210> SEQ ID NO 18
<211> LENGTH: 33
<212> TYPE: DNA
<213> ORGANISM: Homo sapiens

<400> SEQUENCE: 18
ataaaaaata atctaaaaga ttgtggtctc ttc                                 33

<210> SEQ ID NO 19
```

```
<211> LENGTH: 11
<212> TYPE: PRT
<213> ORGANISM: Artificial Sequence
<220> FEATURE:
<223> OTHER INFORMATION: G alpha i 1/2 sequence in random order

<400> SEQUENCE: 19

Asn Gly Ile Lys Cys Leu Phe Asn Asp Lys Leu
1               5                   10

<210> SEQ ID NO 20
<211> LENGTH: 33
<212> TYPE: DNA
<213> ORGANISM: Artificial Sequence
<220> FEATURE:
<223> OTHER INFORMATION: G alpha i 1/2 sequence in random order

<400> SEQUENCE: 20
aacggcatca gtgcctcttt caacgacaag ctg                          33

<210> SEQ ID NO 21
<211> LENGTH: 11
<212> TYPE: PRT
<213> ORGANISM: Homo sapiens

<400> SEQUENCE: 21

Ile Lys Asn Asn Leu Lys Glu Cys Gly Leu Tyr
1               5                   10

<210> SEQ ID NO 22
<211> LENGTH: 33
<212> TYPE: DNA
<213> ORGANISM: Homo sapiens

<400> SEQUENCE: 22
attaaaaaca acttaaagga atgtggactt tat                          33

<210> SEQ ID NO 23
<211> LENGTH: 11
<212> TYPE: PRT
<213> ORGANISM: Homo sapiens

<400> SEQUENCE: 23

Ile Ala Lys Asn Leu Arg Gly Cys Gly Leu Tyr
1               5                   10

<210> SEQ ID NO 24
<211> LENGTH: 33
<212> TYPE: DNA
<213> ORGANISM: Homo sapiens

<400> SEQUENCE: 24
atcgccaaaa acctgcgggg ctgtggactc tac                          33

<210> SEQ ID NO 25
<211> LENGTH: 11
<212> TYPE: PRT
<213> ORGANISM: Homo sapiens

<400> SEQUENCE: 25

Ile Ala Asn Asn Leu Arg Gly Cys Gly Leu Tyr
1               5                   10

<210> SEQ ID NO 26
<211> LENGTH: 33
```

```
<212> TYPE: DNA
<213> ORGANISM: Homo sapiens

<400> SEQUENCE: 26
attgccaaca acctccgggg ctgcggcttg tac                                33

<210> SEQ ID NO 27
<211> LENGTH: 11
<212> TYPE: PRT
<213> ORGANISM: Homo sapiens

<400> SEQUENCE: 27

Ile Gln Asn Asn Leu Lys Tyr Ile Gly Leu Cys
1               5                   10

<210> SEQ ID NO 28
<211> LENGTH: 33
<212> TYPE: DNA
<213> ORGANISM: Homo sapiens

<400> SEQUENCE: 28
atacagaaca atctcaagta cattggcctt tgc                                33

<210> SEQ ID NO 29
<211> LENGTH: 33
<212> TYPE: DNA
<213> ORGANISM: Homo sapiens

<400> SEQUENCE: 29
ctgcagctga acctcaagga gtacaacctg gtc                                33

<210> SEQ ID NO 30
<211> LENGTH: 11
<212> TYPE: PRT
<213> ORGANISM: Homo sapiens

<400> SEQUENCE: 30

Leu Gln Leu Asn Leu Lys Glu Tyr Asn Ala Val
1               5                   10

<210> SEQ ID NO 31
<211> LENGTH: 33
<212> TYPE: DNA
<213> ORGANISM: Homo sapiens

<400> SEQUENCE: 31
ctccagttga acctgaagga gtacaatgca gtc                                33

<210> SEQ ID NO 32
<211> LENGTH: 11
<212> TYPE: PRT
<213> ORGANISM: Homo sapiens

<400> SEQUENCE: 32

Gln Arg Met His Leu Lys Gln Tyr Glu Leu Leu
1               5                   10

<210> SEQ ID NO 33
<211> LENGTH: 33
<212> TYPE: DNA
<213> ORGANISM: Homo sapiens

<400> SEQUENCE: 33
cagcggatgc acctcaagca gtatgagctc ttg                                33
```

<210> SEQ ID NO 34
<211> LENGTH: 11
<212> TYPE: PRT
<213> ORGANISM: Homo sapiens

<400> SEQUENCE: 34

Leu Gln Leu Asn Leu Arg Glu Phe Asn Leu Val
1               5                   10

<210> SEQ ID NO 35
<211> LENGTH: 33
<212> TYPE: DNA
<213> ORGANISM: Homo sapiens

<400> SEQUENCE: 35
ctacagctaa acctaaggga attcaacctt gtc                          33

<210> SEQ ID NO 36
<211> LENGTH: 11
<212> TYPE: PRT
<213> ORGANISM: Homo sapiens

<400> SEQUENCE: 36

Leu Ala Arg Tyr Leu Asp Glu Ile Asn Leu Leu
1               5                   10

<210> SEQ ID NO 37
<211> LENGTH: 33
<212> TYPE: DNA
<213> ORGANISM: Homo sapiens

<400> SEQUENCE: 37
ctcgcccgct acctggacga gatcaacctg ctg                          33

<210> SEQ ID NO 38
<211> LENGTH: 11
<212> TYPE: PRT
<213> ORGANISM: Homo sapiens

<400> SEQUENCE: 38

Leu Gln Glu Asn Leu Lys Asp Ile Met Leu Gln
1               5                   10

<210> SEQ ID NO 39
<211> LENGTH: 33
<212> TYPE: DNA
<213> ORGANISM: Homo sapiens

<400> SEQUENCE: 39
ctgcaggaga acctgaagga catcatgctg cag                          33

<210> SEQ ID NO 40
<211> LENGTH: 11
<212> TYPE: PRT
<213> ORGANISM: Homo sapiens

<400> SEQUENCE: 40

Leu His Asp Asn Leu Lys Gln Leu Met Leu Gln
1               5                   10

<210> SEQ ID NO 41
<211> LENGTH: 33
<212> TYPE: DNA

<213> ORGANISM: Homo sapiens

<400> SEQUENCE: 41
ctgcatgaca acctcaagca gcttatgcta cag                                    33

<210> SEQ ID NO 42
<211> LENGTH: 33
<212> TYPE: DNA
<213> ORGANISM: Homo sapiens

<400> SEQUENCE: 42
cagcgcatgc accttcgtca gtacgagctg ctc                                    33

<210> SEQ ID NO 43
<211> LENGTH: 20
<212> TYPE: DNA
<213> ORGANISM: Artificial Sequence
<220> FEATURE:
<223> OTHER INFORMATION: 5' minigene construct sequence

<400> SEQUENCE: 43
gatccgccgc caccatggga                                                   20

<210> SEQ ID NO 44
<211> LENGTH: 4
<212> TYPE: DNA
<213> ORGANISM: Artificial Sequence
<220> FEATURE:
<223> OTHER INFORMATION: 3' minigene construct sequence

<400> SEQUENCE: 44 tgaa                                                                     4

<210> SEQ ID NO 45
<211> LENGTH: 11
<212> TYPE: PRT
<213> ORGANISM: Drosophila melanogaster

<400> SEQUENCE: 45

Ile Lys Asn Asn Leu Lys Gln Ile Gly Leu Phe
1               5                   10

<210> SEQ ID NO 46
<211> LENGTH: 11
<212> TYPE: PRT
<213> ORGANISM: Drosophila melanogaster

<400> SEQUENCE: 46

Leu Ser Glu Asn Val Ser Ser Met Gly Leu Phe
1               5                   10

<210> SEQ ID NO 47
<211> LENGTH: 11
<212> TYPE: PRT
<213> ORGANISM: Homo sapiens

<400> SEQUENCE: 47

Ile Ala Lys Asn Leu Arg Gly Cys Gly Leu Tyr
1               5                   10

<210> SEQ ID NO 48
<211> LENGTH: 11
<212> TYPE: PRT
<213> ORGANISM: Xenopus laevis

```
<400> SEQUENCE: 48

Ile Ala Tyr Asn Leu Arg Gly Cys Gly Leu Tyr
1               5                   10

<210> SEQ ID NO 49
<211> LENGTH: 11
<212> TYPE: PRT
<213> ORGANISM: Caenorhabditis elegans

<400> SEQUENCE: 49

Ile Gln Ala Asn Leu Gln Gly Cys Gly Leu Tyr
1               5                   10

<210> SEQ ID NO 50
<211> LENGTH: 11
<212> TYPE: PRT
<213> ORGANISM: Caenorhabditis elegans

<400> SEQUENCE: 50

Ile Gln Ser Asn Leu His Lys Ser Gly Leu Tyr
1               5                   10

<210> SEQ ID NO 51
<211> LENGTH: 11
<212> TYPE: PRT
<213> ORGANISM: Caenorhabditis elegans

<400> SEQUENCE: 51

Leu Ser Thr Lys Leu Lys Gly Cys Gly Leu Tyr
1               5                   10

<210> SEQ ID NO 52
<211> LENGTH: 11
<212> TYPE: PRT
<213> ORGANISM: Xenopus laevis

<400> SEQUENCE: 52

Ile Lys Ser Asn Leu Met Glu Cys Gly Leu Tyr
1               5                   10

<210> SEQ ID NO 53
<211> LENGTH: 11
<212> TYPE: PRT
<213> ORGANISM: Canis familiaris

<400> SEQUENCE: 53

Val Gln Gln Asn Leu Lys Lys Ser Gly Ile Met
1               5                   10

<210> SEQ ID NO 54
<211> LENGTH: 11
<212> TYPE: PRT
<213> ORGANISM: Schizosaccharomyces pombe

<400> SEQUENCE: 54

Leu Gln His Ser Leu Lys Glu Ala Gly Met Phe
1               5                   10

<210> SEQ ID NO 55
<211> LENGTH: 11
<212> TYPE: PRT
<213> ORGANISM: Drosophila melanogaster

<400> SEQUENCE: 55
```

Leu Gln Arg Asn Leu Asn Ala Leu Met Leu Gln
1               5                   10

<210> SEQ ID NO 56
<211> LENGTH: 11
<212> TYPE: PRT
<213> ORGANISM: Saccharomyces cerevisiae

<400> SEQUENCE: 56

Glu Asn Thr Leu Lys Asp Ser Gly Val Leu Gln
1               5                   10

<210> SEQ ID NO 57
<211> LENGTH: 11
<212> TYPE: PRT
<213> ORGANISM: Drosophila melanogaster

<400> SEQUENCE: 57

Leu Gln Ser Asn Leu Lys Glu Tyr Asn Leu Val
1               5                   10

<210> SEQ ID NO 58
<211> LENGTH: 11
<212> TYPE: PRT
<213> ORGANISM: Xenopus laevis

<400> SEQUENCE: 58

Leu Gln His Asn Leu Lys Glu Tyr Asn Leu Val
1               5                   10

<210> SEQ ID NO 59
<211> LENGTH: 11
<212> TYPE: PRT
<213> ORGANISM: Sporothrix schenckii

<400> SEQUENCE: 59

Ile Gln Glu Asn Leu Arg Leu Cys Gly Leu Ile
1               5                   10

<210> SEQ ID NO 60
<211> LENGTH: 11
<212> TYPE: PRT
<213> ORGANISM: Saccharomyces cerevisiae

<400> SEQUENCE: 60

Ile Gln Gln Asn Leu Lys Lys Ile Gly Ile Ile
1               5                   10

<210> SEQ ID NO 61
<211> LENGTH: 11
<212> TYPE: PRT
<213> ORGANISM: Neurospora crassa

<400> SEQUENCE: 61

Ile Ile Gln Arg Asn Leu Lys Gln Leu Ile Leu
1               5                   10

<210> SEQ ID NO 62
<211> LENGTH: 11
<212> TYPE: PRT
<213> ORGANISM: Filobasidiella neoformans

<400> SEQUENCE: 62

Leu Gln Asn Ala Leu Arg Asp Ser Gly Ile Leu
1               5                   10

<210> SEQ ID NO 63
<211> LENGTH: 11
<212> TYPE: PRT
<213> ORGANISM: Ustilago maydis

<400> SEQUENCE: 63

Leu Thr Asn Ala Leu Lys Asp Ser Gly Ile Leu
1               5                   10

<210> SEQ ID NO 64
<211> LENGTH: 11
<212> TYPE: PRT
<213> ORGANISM: Kluyveromyces lactis

<400> SEQUENCE: 64

Ile Gln Gln Asn Leu Lys Lys Ser Gly Ile Leu
1               5                   10

<210> SEQ ID NO 65
<211> LENGTH: 11
<212> TYPE: PRT
<213> ORGANISM: Kluyveromyces lactis

<400> SEQUENCE: 65

Leu Glu Asn Ser Leu Lys Asp Ser Gly Val Leu
1               5                   10

<210> SEQ ID NO 66
<211> LENGTH: 11
<212> TYPE: PRT
<213> ORGANISM: Ustilago maydis

<400> SEQUENCE: 66

Ile Leu Thr Asn Asn Leu Arg Asp Ile Val Leu
1               5                   10

<210> SEQ ID NO 67
<211> LENGTH: 11
<212> TYPE: PRT
<213> ORGANISM: Mus musculus

<400> SEQUENCE: 67

Gln Arg Met His Leu Pro Gln Tyr Glu Leu Leu
1               5                   10

<210> SEQ ID NO 68
<211> LENGTH: 11
<212> TYPE: PRT
<213> ORGANISM: Homo sapiens

<400> SEQUENCE: 68

Gln Arg Met His Leu Lys Gly Tyr Glu Leu Leu
1               5                   10

<210> SEQ ID NO 69
<211> LENGTH: 11
<212> TYPE: PRT
<213> ORGANISM: Coprinus congregatus

<400> SEQUENCE: 69

Leu Gln Leu His Leu Arg Glu Cys Gly Leu Leu
1               5                   10

<210> SEQ ID NO 70
<211> LENGTH: 11
<212> TYPE: PRT
<213> ORGANISM: Lycopersicon esculentum

<400> SEQUENCE: 70

Arg Arg Arg Asn Leu Phe Glu Ala Gly Leu Leu
1               5                   10

<210> SEQ ID NO 71
<211> LENGTH: 11
<212> TYPE: PRT
<213> ORGANISM: Glycine max

<400> SEQUENCE: 71

Arg Arg Arg Asn Leu Leu Glu Ala Gly Leu Leu
1               5                   10

<210> SEQ ID NO 72
<211> LENGTH: 11
<212> TYPE: PRT
<213> ORGANISM: Glycine max

<400> SEQUENCE: 72

Arg Arg Arg Asn Pro Leu Glu Ala Gly Leu Leu
1               5                   10

<210> SEQ ID NO 73
<211> LENGTH: 11
<212> TYPE: PRT
<213> ORGANISM: Ustilago maydis

<400> SEQUENCE: 73

Ile Gln Val Asn Leu Arg Asp Cys Gly Leu Leu
1               5                   10

<210> SEQ ID NO 74
<211> LENGTH: 11
<212> TYPE: PRT
<213> ORGANISM: Ustilago maydis

<400> SEQUENCE: 74

Arg Glu Asn Leu Lys Leu Thr Gly Leu Val Gly
1               5                   10

<210> SEQ ID NO 75
<211> LENGTH: 11
<212> TYPE: PRT
<213> ORGANISM: Oryza sativa

<400> SEQUENCE: 75

Asp Glu Ser Met Arg Arg Ser Arg Glu Gly Thr
1               5                   10

<210> SEQ ID NO 76
<211> LENGTH: 11
<212> TYPE: PRT
<213> ORGANISM: Calliphora vicina

<400> SEQUENCE: 76

Met Gln Asn Ala Leu Lys Glu Phe Asn Leu Gly
1               5                   10

<210> SEQ ID NO 77
<211> LENGTH: 11

```
<212> TYPE: PRT
<213> ORGANISM: Dictyostelium discoideum

<400> SEQUENCE: 77

Thr Gln Cys Val Met Lys Ala Gly Leu Tyr Ser
1               5                   10

<210> SEQ ID NO 78
<211> LENGTH: 11
<212> TYPE: PRT
<213> ORGANISM: Caenorhabditis elegans

<400> SEQUENCE: 78

Ile Ile Ser Ala Ser Leu Lys Met Val Gly Val
1               5                   10

<210> SEQ ID NO 79
<211> LENGTH: 11
<212> TYPE: PRT
<213> ORGANISM: Caenorhabditis elegans

<400> SEQUENCE: 79

Asn Glu Asn Leu Arg Ser Ala Gly Leu His Glu
1               5                   10

<210> SEQ ID NO 80
<211> LENGTH: 11
<212> TYPE: PRT
<213> ORGANISM: Caenorhabditis elegans

<400> SEQUENCE: 80

Arg Leu Ile Arg Tyr Ala Asn Asn Ile Pro Val
1               5                   10

<210> SEQ ID NO 81
<211> LENGTH: 11
<212> TYPE: PRT
<213> ORGANISM: Caenorhabditis elegans

<400> SEQUENCE: 81

Ile Ala Lys Asn Leu Lys Ser Met Gly Leu Cys
1               5                   10

<210> SEQ ID NO 82
<211> LENGTH: 11
<212> TYPE: PRT
<213> ORGANISM: Caenorhabditis elegans

<400> SEQUENCE: 82

Ile Gly Arg Asn Leu Arg Gly Thr Gly Met Glu
1               5                   10

<210> SEQ ID NO 83
<211> LENGTH: 11
<212> TYPE: PRT
<213> ORGANISM: Caenorhabditis elegans

<400> SEQUENCE: 83

Ile Gln His Thr Met Gln Lys Val Gly Ile Gln
1               5                   10

<210> SEQ ID NO 84
<211> LENGTH: 11
<212> TYPE: PRT
<213> ORGANISM: Caenorhabditis elegans
```

```
<400> SEQUENCE: 84

Ile Gln Lys Asn Leu Gln Lys Ala Gly Met Met
1               5                   10

<210> SEQ ID NO 85
<211> LENGTH: 11
<212> TYPE: PRT
<213> ORGANISM: Dictyostelium discoideum

<400> SEQUENCE: 85

Leu Lys Asn Ile Phe Asn Thr Ile Ile Asn Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Gq library peptide

<400> SEQUENCE: 86

Leu Leu Leu Gln Leu Val Glu His Thr Leu Val
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Gq library peptide

<400> SEQUENCE: 87

His Arg Leu Asn Leu Leu Glu Tyr Cys Leu Val
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Gq library peptide

<400> SEQUENCE: 88

Glu Gln Trp Asn Met Asn Thr Phe His Met Ile
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Gq library peptide

<400> SEQUENCE: 89

Ser Gln Val Lys Leu Gln Lys Gly His Leu Val
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Gq library sequence

<400> SEQUENCE: 90
```

```
Leu Arg Leu Leu Leu Glu Tyr Asn Leu Gly
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Gq library peptide

<400> SEQUENCE: 91

Arg Arg Leu Lys Val Asn Glu Tyr Lys Leu Leu
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Gq library peptide

<400> SEQUENCE: 92

Leu Gln Leu Arg Leu Arg Glu His Asn Leu Val
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Gq library peptide

<400> SEQUENCE: 93

His Val Leu Asn Ser Lys Glu Tyr Asn Gln Val
1               5                   10

<210> SEQ ID NO 94
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 94

Met Lys Leu Asn Val Ser Glu Ser Asn Leu Val
1               5                   10

<210> SEQ ID NO 95
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 95

Leu Gln Thr Asn Gln Lys Glu Tyr Asp Met Asp
1               5                   10

<210> SEQ ID NO 96
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 96

Leu Gln Leu Asn Pro Arg Glu Asp Lys Leu Trp
```

```
                        -continued
1               5               10

<210> SEQ ID NO 97
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 97

Arg His Leu Asp Leu Asn Ala Cys Asn Met Gly
1               5                   10

<210> SEQ ID NO 98
<211> LENGTH: 10
<212> TYPE: PRT
<213> ORGANISM: Artificial Sequence
<220> FEATURE:
<223> OTHER INFORMATION: G alpha 11 library peptide

<400> SEQUENCE: 98

Leu Arg Asn Asp Ile Glu Ala Leu Leu Val
1               5                   10

<210> SEQ ID NO 99
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 99

Leu Val Gln Asp Arg Gln Glu Ser Ile Leu Val
1               5                   10

<210> SEQ ID NO 100
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 100

Leu Gln Leu Lys His Lys Glu Asn Asn Leu Met
1               5                   10

<210> SEQ ID NO 101
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 101

Leu Gln Val Asn Leu Glu Glu Tyr His Leu Val
1               5                   10

<210> SEQ ID NO 102
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 102

Leu Gln Phe Asn Leu Asn Asp Cys Asn Leu Val
1               5                   10
```

<210> SEQ ID NO 103
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 103

Met Lys Leu Lys Leu Lys Glu Asp Asn Leu Val
1               5                   10

<210> SEQ ID NO 104
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 104

His Gln Leu Asp Leu Leu Glu Tyr Asn Leu Gly
1               5                   10

<210> SEQ ID NO 105
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 105

Leu Arg Leu Asp Phe Ser Glu Lys Gln Leu Val
1               5                   10

<210> SEQ ID NO 106
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 106

Leu Gln Lys Asn Leu Lys Glu Tyr Asn Met Val
1               5                   10

<210> SEQ ID NO 107
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 107

Leu Gln Tyr Asn Leu Met Glu Asp Tyr Leu Asn
1               5                   10

<210> SEQ ID NO 108
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 108

Leu Gln Met Tyr Leu Arg Gly Tyr Asn Leu Val
1               5                   10

```
<210> SEQ ID NO 109
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 109

Leu Pro Leu Asn Pro Lys Glu Tyr Ser Leu Val
1               5                   10

<210> SEQ ID NO 110
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 110

Met Asn Leu Thr Leu Lys Glu Cys Asn Leu Val
1               5                   10

<210> SEQ ID NO 111
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 111

Leu Gln Gln Ser Leu Ile Glu Tyr Asn Leu Leu
1               5                   10

<210> SEQ ID NO 112
<211> LENGTH: 13
<212> TYPE: PRT
<213> ORGANISM: Artificial Sequence
<220> FEATURE:
<223> OTHER INFORMATION: G alpha i minigene peptide

<400> SEQUENCE: 112

Met Gly Ile Lys Asn Asn Leu Lys Asp Cys Gly Leu Phe
1               5                   10

<210> SEQ ID NO 113
<211> LENGTH: 13
<212> TYPE: PRT
<213> ORGANISM: Artificial Sequence
<220> FEATURE:
<223> OTHER INFORMATION: G alpha i R minigene peptide

<400> SEQUENCE: 113

Met Gly Asn Gly Ile Lys Cys Leu Phe Asn Asp Lys Leu
1               5                   10

<210> SEQ ID NO 114
<211> LENGTH: 13
<212> TYPE: PRT
<213> ORGANISM: Artificial Sequence
<220> FEATURE:
<223> OTHER INFORMATION: G alpha q minigene peptide

<400> SEQUENCE: 114

Met Gly Leu Gln Leu Asn Leu Lys Glu Tyr Asn Ala Val
1               5                   10
```

```
<210> SEQ ID NO 115
<211> LENGTH: 13
<212> TYPE: PRT
<213> ORGANISM: Artificial Sequence
<220> FEATURE:
<223> OTHER INFORMATION: G alpha q** minigene peptide

<400> SEQUENCE: 115

Met Gly Leu Gln Leu Asn Leu Lys Glu Tyr Asn Thr Leu
1               5                   10

<210> SEQ ID NO 116
<211> LENGTH: 13
<212> TYPE: PRT
<213> ORGANISM: Artificial Sequence
<220> FEATURE:
<223> OTHER INFORMATION: G alpha 12 minigene peptide

<400> SEQUENCE: 116

Met Gly Leu Gln Glu Asn Leu Lys Asp Ile Met Leu Gln
1               5                   10

<210> SEQ ID NO 117
<211> LENGTH: 13
<212> TYPE: PRT
<213> ORGANISM: Artificial Sequence
<220> FEATURE:
<223> OTHER INFORMATION: G alpha 13 minigene peptide

<400> SEQUENCE: 117

Met Gly Leu His Asp Asn Leu Lys Gln Leu Met Leu Gln
1               5                   10

<210> SEQ ID NO 118
<211> LENGTH: 68
<212> TYPE: DNA
<213> ORGANISM: Artificial Sequence
<220> FEATURE:
<223> OTHER INFORMATION: G alpha t library construct
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 118
gaggtggtnn knnknnknnk attcaaggag aacctgaagg actgcggcct cttctaacta    60
agtaaagc                                                             68

<210> SEQ ID NO 119
<211> LENGTH: 67
<212> TYPE: DNA
<213> ORGANISM: Artificial Sequence
<220> FEATURE:
<223> OTHER INFORMATION: Gs library construct
<220> FEATURE:
<221> NAME/KEY: misc_feature
<222> LOCATION: (9)..(10)
<223> OTHER INFORMATION: n is a, c, g, or t
```

```
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 119
gaggtggtnn knnknnknnk ctgcagctga acctgaagga gtacaatctg gtctaactaa      60
gtaaagc                                                                67

<210> SEQ ID NO 120
<211> LENGTH: 67
<212> TYPE: DNA
<213> ORGANISM: Artificial Sequence
<220> FEATURE:
<223> OTHER INFORMATION: G12 library construct
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 120
gaggtggtnn knnknnknnk ctgcaggaga acctgaagga catcatgctg cagtaactaa      60
gtaaagc                                                                67

<210> SEQ ID NO 121
<211> LENGTH: 67
<212> TYPE: DNA
<213> ORGANISM: Artificial Sequence
<220> FEATURE:
<223> OTHER INFORMATION: G13 library construct
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 121
gaggtggtnn knnknnknnk ctgcatgaca acctcaagca gcttatgcta cagtaactaa      60
gtaaagc                                                                67
```

```
<210> SEQ ID NO 122
<211> LENGTH: 67
<212> TYPE: DNA
<213> ORGANISM: Artificial Sequence
<220> FEATURE:
<223> OTHER INFORMATION: G15 library construct
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 122
gaggtggtnn knnknnknnk ctcgcccggt acctggacga gattaatctg ctgtaactaa      60
gtaaagc                                                               67

<210> SEQ ID NO 123
<211> LENGTH: 67
<212> TYPE: DNA
<213> ORGANISM: Artificial Sequence
<220> FEATURE:
<223> OTHER INFORMATION: Gz library construct
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 123
gaggtggtnn knnknnknnk atacagaaca atctcaagta cattggcctt tgctaactaa      60
gtaaagc                                                               67

<210> SEQ ID NO 124
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 124

Ile Arg Glu Asn Leu Lys Asp Cys Gly Leu Phe
1               5                   10

<210> SEQ ID NO 125
<211> LENGTH: 11
<212> TYPE: PRT
<213> ORGANISM: Artificial Sequence
<220> FEATURE:
```

```
<223> OTHER INFORMATION: G alpha t library peptide

<400> SEQUENCE: 125

Leu Leu Glu Asn Leu Arg Asp Cys Gly Met Phe
1               5                   10

<210> SEQ ID NO 126
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 126

Ile Gln Gly Val Leu Lys Asp Cys Gly Leu Leu
1               5                   10

<210> SEQ ID NO 127
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 127

Ile Cys Glu Asn Leu Lys Glu Cys Gly Leu Phe
1               5                   10

<210> SEQ ID NO 128
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 128

Met Leu Glu Asn Leu Lys Asp Cys Gly Leu Phe
1               5                   10

<210> SEQ ID NO 129
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 129

Val Leu Glu Asp Leu Lys Ser Cys Gly Leu Phe
1               5                   10

<210> SEQ ID NO 130
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 130

Met Leu Lys Asn Leu Lys Asp Cys Gly Met Phe
1               5                   10

<210> SEQ ID NO 131
<211> LENGTH: 11
<212> TYPE: PRT
<213> ORGANISM: Artificial Sequence
<220> FEATURE:
<223> OTHER INFORMATION: G alpha t library peptide
```

```
<400> SEQUENCE: 131

Leu Leu Asp Asn Ile Lys Asp Cys Gly Leu Phe
1               5                   10

<210> SEQ ID NO 132
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 132

Ile Leu Thr Lys Leu Thr Asp Cys Gly Leu Phe
1               5                   10

<210> SEQ ID NO 133
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 133

Leu Arg Glu Ser Leu Lys Gln Cys Gly Leu Phe
1               5                   10

<210> SEQ ID NO 134
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 134

Ile His Ala Ser Leu Arg Asp Cys Gly Leu Phe
1               5                   10

<210> SEQ ID NO 135
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 135

Ile Arg Gly Ser Leu Lys Asp Cys Gly Leu Phe
1               5                   10

<210> SEQ ID NO 136
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 136

Ile Phe Leu Asn Leu Lys Asp Cys Gly Leu Phe
1               5                   10

<210> SEQ ID NO 137
<211> LENGTH: 11
<212> TYPE: PRT
<213> ORGANISM: Artificial Sequence
<220> FEATURE:
<223> OTHER INFORMATION: G alpha t library peptide
```

-continued

```
<400> SEQUENCE: 137

Ile Arg Glu Asn Leu Glu Asp Cys Gly Leu Phe
1               5                   10

<210> SEQ ID NO 138
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 138

Ile Ile Asp Asn Leu Lys Asp Cys Gly Leu Phe
1               5                   10

<210> SEQ ID NO 139
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 139

Met Arg Glu Ser Leu Lys Asp Cys Gly Leu Phe
1               5                   10

<210> SEQ ID NO 140
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 140

Ile Arg Glu Thr Leu Lys Asp Cys Gly Leu Leu
1               5                   10

<210> SEQ ID NO 141
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 141

Ile Leu Ala Asp Val Ile Asp Cys Gly Leu Phe
1               5                   10

<210> SEQ ID NO 142
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 142

Met Cys Glu Ser Leu Lys Glu Cys Gly Leu Phe
1               5                   10

<210> SEQ ID NO 143
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 143
```

```
Ile Arg Glu Lys Trp Lys Asp Leu Ala Leu Phe
1               5                  10

<210> SEQ ID NO 144
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 144

Val Arg Asp Asn Leu Lys Asn Cys Phe Leu Phe
1               5                  10

<210> SEQ ID NO 145
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 145

Ile Gly Glu Gln Ile Glu Asp Cys Gly Pro Phe
1               5                  10

<210> SEQ ID NO 146
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 146

Ile Arg Asn Asn Leu Lys Arg Tyr Gly Met Phe
1               5                  10

<210> SEQ ID NO 147
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 147

Ile Arg Glu Asn Leu Lys Asp Leu Gly Leu Val
1               5                  10

<210> SEQ ID NO 148
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 148

Ile Arg Glu Asn Phe Lys Tyr Leu Gly Leu Trp
1               5                  10

<210> SEQ ID NO 149
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 149
```

Ser Leu Glu Ile Leu Lys Asp Trp Gly Leu Phe
1               5                  10

<210> SEQ ID NO 150
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 150

Ile Arg Gly Thr Leu Lys Gly Trp Gly Leu Phe
1               5                  10

<210> SEQ ID NO 151
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 151

Ser Trp Val
1

<210> SEQ ID NO 152
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 152

Phe Val Asn Cys
1

<210> SEQ ID NO 153
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 153

Glu Val Arg Arg
1

<210> SEQ ID NO 154
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 154

Arg Val Gln
1

<210> SEQ ID NO 155
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 155

Arg Leu Thr Arg

```
<210> SEQ ID NO 156
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 156

Ser Arg Lys
1

<210> SEQ ID NO 157
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 157

Met Thr His Ser
1

<210> SEQ ID NO 158
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 158

Ser Gly Pro Gln
1

<210> SEQ ID NO 159
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 159

Met Leu Asn
1

<210> SEQ ID NO 160
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 160

Leu Gln Arg Asn Lys Lys Gln Tyr Asn Leu Gly
1               5                   10

<210> SEQ ID NO 161
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 161

Leu Gln Leu Arg Tyr Lys Cys Tyr Asn Leu Val
1               5                   10
```

```
<210> SEQ ID NO 162
<211> LENGTH: 11
<212> TYPE: PRT
<213> ORGANISM: Artificial Sequence
<220> FEATURE:
<223> OTHER INFORMATION: G alpha t library pepetide

<400> SEQUENCE: 162

Val His Val Lys Leu Lys Glu Tyr Asn Leu Val
1               5                   10

<210> SEQ ID NO 163
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 163

Leu Gln Leu Asn Val Lys Glu Tyr Asn Leu Val
1               5                   10

<210> SEQ ID NO 164
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 164

Leu Arg Ile Tyr Leu Lys Gly Tyr Asn Leu Val
1               5                   10

<210> SEQ ID NO 165
<211> LENGTH: 3
<212> TYPE: PRT
<213> ORGANISM: Artificial Sequence
<220> FEATURE:
<223> OTHER INFORMATION: G alpha 11 library linker sequence

<400> SEQUENCE: 165

Ser Ile Arg
1

<210> SEQ ID NO 166
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 166

Arg Trp Ile Val
1

<210> SEQ ID NO 167
<211> LENGTH: 3
<212> TYPE: PRT
<213> ORGANISM: Artificial Sequence
<220> FEATURE:
<223> OTHER INFORMATION: G alpha 11 library linker sequence

<400> SEQUENCE: 167

Gly Gly His
1
```

```
<210> SEQ ID NO 168
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 168

Arg Ser Glu Val
1

<210> SEQ ID NO 169
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 169

Cys Glu Pro Gly
1

<210> SEQ ID NO 170
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 170

His Gln Met Ala
1

<210> SEQ ID NO 171
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 171

Val Pro Ser Pro
1

<210> SEQ ID NO 172
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 172

Gln Met Pro Asn
1

<210> SEQ ID NO 173
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 173

Met Trp Pro Ser
1
```

```
<210> SEQ ID NO 174
<211> LENGTH: 3
<212> TYPE: PRT
<213> ORGANISM: Artificial Sequence
<220> FEATURE:
<223> OTHER INFORMATION: G alpha 11 library linker sequence

<400> SEQUENCE: 174

Cys Val Glu
1

<210> SEQ ID NO 175
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 175

Leu Gln Leu Asn Leu Lys Val Tyr Asn Leu Val
1               5                   10

<210> SEQ ID NO 176
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 176

Leu Glu Leu Asn Leu Lys Val Tyr Asn Leu Phe
1               5                   10

<210> SEQ ID NO 177
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 177

Leu His Leu Asn Met Ala Glu Val Ser Leu Val
1               5                   10

<210> SEQ ID NO 178
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 178

Leu Lys Arg Tyr Leu Lys Glu Ser Asn Leu Val
1               5                   10

<210> SEQ ID NO 179
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 179

Pro Arg Gln Leu
1

<210> SEQ ID NO 180
```

```
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 180

Phe Phe Trp Val
1

<210> SEQ ID NO 181
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 181

Gln Arg Asp Thr
1

<210> SEQ ID NO 182
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 182

Asn Phe Arg Asn
1

<210> SEQ ID NO 183
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 183

Leu Gln Leu Lys Arg Gly Glu Tyr Ile Leu Val
1               5                   10

<210> SEQ ID NO 184
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 184

Cys Ser Leu Lys Leu Lys Ala Tyr Asn Leu Val
1               5                   10

<210> SEQ ID NO 185
<211> LENGTH: 11
<212> TYPE: PRT
<213> ORGANISM: Artificial Sequence
<220> FEATURE:
<223> OTHER INFORMATION: G alpha library peptide

<400> SEQUENCE: 185

Leu Gln Met Asn His Asn Glu Tyr Asn Leu Val
1               5                   10

<210> SEQ ID NO 186
<211> LENGTH: 11
```

-continued

```
<212> TYPE: PRT
<213> ORGANISM: Artificial Sequence
<220> FEATURE:
<223> OTHER INFORMATION: G alpha t library peptide

<400> SEQUENCE: 186

Pro Gln Leu Asn Leu Asn Ala Tyr Asn Leu Val
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Gs library peptide

<400> SEQUENCE: 187

Gln Gly Met Gln Leu Arg Arg Phe Lys Leu Arg
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Gs library peptide

<400> SEQUENCE: 188

Arg Trp Leu His Trp Gln Tyr Arg Gly Arg Gly
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Gs library peptide

<400> SEQUENCE: 189

Pro Arg Pro Arg Leu Leu Arg Phe Lys Ile Pro
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Gs library peptide

<400> SEQUENCE: 190

Gln Gly Glu His Leu Arg Gln Leu Gln Leu Gln
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Gs library peptide

<400> SEQUENCE: 191

Gln Arg Leu Arg Leu Gly Pro Asp Glu Leu Phe
1               5                   10

<210> SEQ ID NO 192
<211> LENGTH: 11
<212> TYPE: PRT
```

```
<213> ORGANISM: Artificial Sequence
<220> FEATURE:
<223> OTHER INFORMATION: Gs library peptide

<400> SEQUENCE: 192

Gln Arg Ile His Arg Arg Pro Phe Lys Phe Phe
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Gs library peptide

<400> SEQUENCE: 193

Gln Arg Met Pro Leu Arg Leu Phe Glu Phe Leu
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Gs library peptide

<400> SEQUENCE: 194

Gln Arg Val His Leu Arg Gln Asp Glu Leu Leu
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Gs library peptide

<400> SEQUENCE: 195

Asp Arg Met His Leu Trp Arg Phe Gly Leu Leu
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Gs library peptide

<400> SEQUENCE: 196

Gln Arg Met Pro Leu Arg Gln Tyr Glu Leu Leu
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Gs library peptide

<400> SEQUENCE: 197

Gln Trp Met Asp Leu Arg Gln His Glu Leu Leu
1               5                   10

<210> SEQ ID NO 198
<211> LENGTH: 11
<212> TYPE: PRT
<213> ORGANISM: Artificial Sequence
```

```
<220> FEATURE:
<223> OTHER INFORMATION: Gs library peptide

<400> SEQUENCE: 198

Gln Arg Met Asn Leu Gly Pro Cys Gly Leu Leu
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Gs library peptide

<400> SEQUENCE: 199

Asn Cys Met Lys Phe Arg Ser Cys Gly Leu Phe
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Gs library peptide

<400> SEQUENCE: 200

Gln Arg Leu His Leu Arg Gly Tyr Glu Phe Leu
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Gs library peptide

<400> SEQUENCE: 201

His Arg Arg His Ile Gly Pro Phe Ala Leu Leu
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Gs library peptide

<400> SEQUENCE: 202

Glu Arg Leu His Arg Arg Leu Phe Gln Leu His
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Gs library peptide

<400> SEQUENCE: 203

Pro Cys Ile Gln Leu Gly Gln Tyr Glu Ser Phe
1               5                   10

<210> SEQ ID NO 204
<211> LENGTH: 11
<212> TYPE: PRT
<213> ORGANISM: Artificial Sequence
<220> FEATURE:
```

<223> OTHER INFORMATION: Gs library peptide

<400> SEQUENCE: 204

Gln Arg Leu Arg Leu Arg Lys Tyr Arg Leu Phe
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Gt library peptide

<400> SEQUENCE: 205

Ile Val Glu Ile Leu Glu Asp Cys Gly Leu Phe
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Gt library peptide

<400> SEQUENCE: 206

Met Leu Asp Asn Leu Lys Ala Cys Gly Leu Phe
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Gt library peptide

<400> SEQUENCE: 207

Ile Leu Glu Asn Leu Lys Asp Cys Gly Leu Phe
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Gt library peptide

<400> SEQUENCE: 208

Leu Arg Glu Asn Leu Lys Asp Cys Gly Leu Leu
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Gt library peptide

<400> SEQUENCE: 209

Leu Leu Asp Ile Leu Lys Asp Cys Gly Leu Phe
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Gt library peptide

<400> SEQUENCE: 210

Val Arg Asp Ile Leu Lys Asp Cys Gly Leu Phe
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Gt library peptide

<400> SEQUENCE: 211

Ile Leu Glu Ser Leu Asn Glu Cys Gly Leu Phe
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Gt library sequence

<400> SEQUENCE: 212

Ile Leu Gln Asn Leu Lys Asp Cys Gly Leu Phe
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Gt library sequence

<400> SEQUENCE: 213

Met Leu Asp Asn Leu Lys Asp Cys Gly Leu Phe
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Gt library sequence

<400> SEQUENCE: 214

Ile His Asp Arg Leu Lys Asp Cys Gly Leu Phe
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Gt library peptide

<400> SEQUENCE: 215

Ile Cys Glu Asn Leu Lys Asp Cys Gly Leu Phe
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Gt library peptide

```
<400> SEQUENCE: 216

Ile Val Lys Asn Leu Glu Asp Cys Gly Leu Phe
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Gt library peptide

<400> SEQUENCE: 217

Ile Ser Lys Asn Leu Arg Asp Cys Gly Leu Leu
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Gt library peptide

<400> SEQUENCE: 218

Ile Arg Asp Asn Leu Lys Asp Cys Gly Leu Phe
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Gt library peptide

<400> SEQUENCE: 219

Ile Arg Glu Phe Leu Thr Asp Cys Gly Leu Phe
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Gt library peptide

<400> SEQUENCE: 220

Ile Arg Leu Asp Leu Lys Asp Val Ser Leu Phe
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Gt library sequence

<400> SEQUENCE: 221

Ile Cys Glu Arg Leu Asn Asp Cys Gly Leu Cys
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Gt library peptide

<400> SEQUENCE: 222
```

Pro Arg Asp Asn Thr Lys Val Arg Gly Leu Phe
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Gt library peptide

<400> SEQUENCE: 223

Phe Trp Gly Asn Leu Gln Asp Ser Gly Leu Phe
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Gt library peptide

<400> SEQUENCE: 224

Arg Arg Gly Asn Gly Lys Asp Cys Arg His Phe
1               5                   10

<210> SEQ ID NO 225
<211> LENGTH: 11
<212> TYPE: PRT
<213> ORGANISM: Artificial Sequence
<220> FEATURE:
<223> OTHER INFORMATION: G12 library peptide

<400> SEQUENCE: 225

Leu Gln Glu Asn Leu Lys Glu Met Met Leu Gln
1               5                   10

<210> SEQ ID NO 226
<211> LENGTH: 11
<212> TYPE: PRT
<213> ORGANISM: Artificial Sequence
<220> FEATURE:
<223> OTHER INFORMATION: G12 library peptide

<400> SEQUENCE: 226

Leu Glu Glu Asn Leu Lys Tyr Arg Met Leu Asp
1               5                   10

<210> SEQ ID NO 227
<211> LENGTH: 11
<212> TYPE: PRT
<213> ORGANISM: Artificial Sequence
<220> FEATURE:
<223> OTHER INFORMATION: G12 library peptide

<400> SEQUENCE: 227

Leu Gln Glu Asp Leu Lys Gly Met Thr Leu Gln
1               5                   10

<210> SEQ ID NO 228
<211> LENGTH: 11
<212> TYPE: PRT
<213> ORGANISM: Artificial Sequence
<220> FEATURE:
<223> OTHER INFORMATION: G12 library peptide

<400> SEQUENCE: 228

Leu Gln Glu Thr Met Lys Asp Gln Ser Leu Gln
1               5                   10

<210> SEQ ID NO 229
<211> LENGTH: 11
<212> TYPE: PRT
<213> ORGANISM: Artificial Sequence
<220> FEATURE:
<223> OTHER INFORMATION: G12 library peptide

<400> SEQUENCE: 229

Pro Gln Val Asn Leu Lys Ser Ile Met Arg Gln
1               5                   10

<210> SEQ ID NO 230
<211> LENGTH: 11
<212> TYPE: PRT
<213> ORGANISM: Artificial Sequence
<220> FEATURE:
<223> OTHER INFORMATION: G12 library peptide

<400> SEQUENCE: 230

Trp Gln His Lys Leu Ser Glu Val Met Leu Gln
1               5                   10

<210> SEQ ID NO 231
<211> LENGTH: 11
<212> TYPE: PRT
<213> ORGANISM: Artificial Sequence
<220> FEATURE:
<223> OTHER INFORMATION: G12 library peptide

<400> SEQUENCE: 231

Leu Lys Glu His Leu Met Glu Arg Met Leu Gln
1               5                   10

<210> SEQ ID NO 232
<211> LENGTH: 11
<212> TYPE: PRT
<213> ORGANISM: Artificial Sequence
<220> FEATURE:
<223> OTHER INFORMATION: G12 library peptide

<400> SEQUENCE: 232

Leu Leu Gly Met Leu Glu Pro Leu Met Glu Gln
1               5                   10

<210> SEQ ID NO 233
<211> LENGTH: 11
<212> TYPE: PRT
<213> ORGANISM: Artificial Sequence
<220> FEATURE:
<223> OTHER INFORMATION: G13 library peptide

<400> SEQUENCE: 233

Leu Gln Asp Asn Leu Lys Gln Leu Met Leu Gln
1               5                   10

<210> SEQ ID NO 234
<211> LENGTH: 11
<212> TYPE: PRT
<213> ORGANISM: Artificial Sequence
<220> FEATURE:
<223> OTHER INFORMATION: G13 library peptide

<400> SEQUENCE: 234

Leu Gln Asp Asn Leu Arg His Leu Met Leu Gln

```
                1               5                  10

<210> SEQ ID NO 235
<211> LENGTH: 11
<212> TYPE: PRT
<213> ORGANISM: Artificial Sequence
<220> FEATURE:
<223> OTHER INFORMATION: G13 library peptide

<400> SEQUENCE: 235

Leu Gln Asp Lys Ile Asn His Leu Met Leu Gln
1               5                   10

<210> SEQ ID NO 236
<211> LENGTH: 11
<212> TYPE: PRT
<213> ORGANISM: Artificial Sequence
<220> FEATURE:
<223> OTHER INFORMATION: G13 library peptide

<400> SEQUENCE: 236

Leu Gln Ala Asn Arg Lys Leu Gly Met Leu Gln
1               5                   10

<210> SEQ ID NO 237
<211> LENGTH: 11
<212> TYPE: PRT
<213> ORGANISM: Artificial Sequence
<220> FEATURE:
<223> OTHER INFORMATION: G13 library sequence

<400> SEQUENCE: 237

Leu Ile Val Lys Val Lys Gln Leu Ile Trp Gln
1               5                   10

<210> SEQ ID NO 238
<211> LENGTH: 11
<212> TYPE: PRT
<213> ORGANISM: Artificial Sequence
<220> FEATURE:
<223> OTHER INFORMATION: G13 library peptide

<400> SEQUENCE: 238

Met Arg Ala Lys Leu Asn Asn Leu Met Leu Glu
1               5                   10

<210> SEQ ID NO 239
<211> LENGTH: 10
<212> TYPE: PRT
<213> ORGANISM: Artificial Sequence
<220> FEATURE:
<223> OTHER INFORMATION: G13 library peptide

<400> SEQUENCE: 239

Leu Gln Asp Asn Leu Arg His Leu Ile Gln
1               5                   10

<210> SEQ ID NO 240
<211> LENGTH: 10
<212> TYPE: PRT
<213> ORGANISM: Artificial Sequence
<220> FEATURE:
<223> OTHER INFORMATION: G13 library peptide

<400> SEQUENCE: 240

Leu Gln Asp Asn Arg Asn Gln Leu Leu Phe
1               5                   10
```

```
<210> SEQ ID NO 241
<211> LENGTH: 11
<212> TYPE: PRT
<213> ORGANISM: Artificial Sequence
<220> FEATURE:
<223> OTHER INFORMATION: G11 library peptide

<400> SEQUENCE: 241

Leu Gln Leu Asn Arg Lys Asn Tyr Asn Leu Val
1               5                   10

<210> SEQ ID NO 242
<211> LENGTH: 11
<212> TYPE: PRT
<213> ORGANISM: Artificial Sequence
<220> FEATURE:
<223> OTHER INFORMATION: G11 library peptide

<400> SEQUENCE: 242

Leu Gln Leu Asp Leu Lys Glu Ser Asn Met Val
1               5                   10

<210> SEQ ID NO 243
<211> LENGTH: 11
<212> TYPE: PRT
<213> ORGANISM: Artificial Sequence
<220> FEATURE:
<223> OTHER INFORMATION: G11 library peptide

<400> SEQUENCE: 243

Leu Gln Leu Asn Leu Lys Lys Tyr Asn Arg Val
1               5                   10

<210> SEQ ID NO 244
<211> LENGTH: 11
<212> TYPE: PRT
<213> ORGANISM: Artificial Sequence
<220> FEATURE:
<223> OTHER INFORMATION: G11 library peptide

<400> SEQUENCE: 244

Leu Gln Leu Arg Val Lys Glu Tyr Lys Arg Gly
1               5                   10

<210> SEQ ID NO 245
<211> LENGTH: 11
<212> TYPE: PRT
<213> ORGANISM: Artificial Sequence
<220> FEATURE:
<223> OTHER INFORMATION: G11 library peptide

<400> SEQUENCE: 245

Leu Gln Ile Tyr Leu Lys Gly Tyr Asn Leu Val
1               5                   10

<210> SEQ ID NO 246
<211> LENGTH: 11
<212> TYPE: PRT
<213> ORGANISM: Artificial Sequence
<220> FEATURE:
<223> OTHER INFORMATION: G11 library peptide

<400> SEQUENCE: 246

Leu Gln Tyr Asn Leu Lys Glu Ser Phe Val Val
1               5                   10
```

```
<210> SEQ ID NO 247
<211> LENGTH: 11
<212> TYPE: PRT
<213> ORGANISM: Artificial Sequence
<220> FEATURE:
<223> OTHER INFORMATION: G11 library peptide

<400> SEQUENCE: 247

Leu Gln Arg Asp His Val Glu Tyr Lys Leu Phe
1               5                   10

<210> SEQ ID NO 248
<211> LENGTH: 11
<212> TYPE: PRT
<213> ORGANISM: Artificial Sequence
<220> FEATURE:
<223> OTHER INFORMATION: G11 library peptide

<400> SEQUENCE: 248

Leu Val Ile Lys Pro Lys Glu Phe Asn Leu Val
1               5                   10

<210> SEQ ID NO 249
<211> LENGTH: 11
<212> TYPE: PRT
<213> ORGANISM: Artificial Sequence
<220> FEATURE:
<223> OTHER INFORMATION: G11 library peptide

<400> SEQUENCE: 249

Ile Gln Leu Asn Leu Lys Asn Tyr Asn Ile Val
1               5                   10

<210> SEQ ID NO 250
<211> LENGTH: 11
<212> TYPE: PRT
<213> ORGANISM: Artificial Sequence
<220> FEATURE:
<223> OTHER INFORMATION: G11 library peptide

<400> SEQUENCE: 250

Met Gln Leu Asn Leu Lys Glu Tyr Asn Leu Val
1               5                   10

<210> SEQ ID NO 251
<211> LENGTH: 11
<212> TYPE: PRT
<213> ORGANISM: Artificial Sequence
<220> FEATURE:
<223> OTHER INFORMATION: G11 library peptide

<400> SEQUENCE: 251

Val Gln Val Lys Leu Lys Glu Tyr Asn Leu Val
1               5                   10

<210> SEQ ID NO 252
<211> LENGTH: 11
<212> TYPE: PRT
<213> ORGANISM: Artificial Sequence
<220> FEATURE:
<223> OTHER INFORMATION: G11 library peptide

<400> SEQUENCE: 252

Gln Leu Leu Asn Gln Tyr Val Tyr Asn Leu Val
1               5                   10
```

```
<210> SEQ ID NO 253
<211> LENGTH: 11
<212> TYPE: PRT
<213> ORGANISM: Artificial Sequence
<220> FEATURE:
<223> OTHER INFORMATION: G11 library peptide

<400> SEQUENCE: 253

Trp Arg Leu Ser Leu Lys Val Tyr Asn Leu Val
1               5                   10

<210> SEQ ID NO 254
<211> LENGTH: 11
<212> TYPE: PRT
<213> ORGANISM: Artificial Sequence
<220> FEATURE:
<223> OTHER INFORMATION: G11 library peptide

<400> SEQUENCE: 254

Leu Gln Arg Asn Lys Asn Gln Tyr Asn Leu Gly
1               5                   10

<210> SEQ ID NO 255
<211> LENGTH: 11
<212> TYPE: PRT
<213> ORGANISM: Artificial Sequence
<220> FEATURE:
<223> OTHER INFORMATION: G11 library peptide

<400> SEQUENCE: 255

Leu Tyr Leu Asp Leu Lys Glu Tyr Cys Leu Phe
1               5                   10

<210> SEQ ID NO 256
<211> LENGTH: 11
<212> TYPE: PRT
<213> ORGANISM: Artificial Sequence
<220> FEATURE:
<223> OTHER INFORMATION: G11 library peptide

<400> SEQUENCE: 256

Ser Ala Lys Glu Leu Asp Gln Tyr Asn Leu Gly
1               5                   10

<210> SEQ ID NO 257
<211> LENGTH: 11
<212> TYPE: PRT
<213> ORGANISM: Artificial Sequence
<220> FEATURE:
<223> OTHER INFORMATION: G11 library peptide

<400> SEQUENCE: 257

Leu Phe Leu Asn Leu Lys Glu Tyr Ser Leu Val
1               5                   10

<210> SEQ ID NO 258
<211> LENGTH: 11
<212> TYPE: PRT
<213> ORGANISM: Artificial Sequence
<220> FEATURE:
<223> OTHER INFORMATION: G11 library peptide

<400> SEQUENCE: 258

Leu Glu Leu Asn Leu Lys Val Tyr Asn Leu Val
1               5                   10

<210> SEQ ID NO 259
```

<211> LENGTH: 11
<212> TYPE: PRT
<213> ORGANISM: Artificial Sequence
<220> FEATURE:
<223> OTHER INFORMATION: G11 library peptide

<400> SEQUENCE: 259

Leu Pro Leu Asn Leu Ile Asp Phe Ser Leu Met
1               5                   10

<210> SEQ ID NO 260
<211> LENGTH: 11
<212> TYPE: PRT
<213> ORGANISM: Artificial Sequence
<220> FEATURE:
<223> OTHER INFORMATION: G11 library peptide

<400> SEQUENCE: 260

Leu Pro Arg Asn Leu Lys Glu Tyr Asp Leu Gly
1               5                   10

<210> SEQ ID NO 261
<211> LENGTH: 11
<212> TYPE: PRT
<213> ORGANISM: Artificial Sequence
<220> FEATURE:
<223> OTHER INFORMATION: G11 library peptide

<400> SEQUENCE: 261

Leu Arg Leu Asn Asp Ile Glu Ala Leu Leu Val
1               5                   10

<210> SEQ ID NO 262
<211> LENGTH: 11
<212> TYPE: PRT
<213> ORGANISM: Artificial Sequence
<220> FEATURE:
<223> OTHER INFORMATION: G11 library peptide

<400> SEQUENCE: 262

Leu Val Leu Asn Arg Ile Glu Tyr Asn Leu Leu
1               5                   10

<210> SEQ ID NO 263
<211> LENGTH: 11
<212> TYPE: PRT
<213> ORGANISM: Artificial Sequence
<220> FEATURE:
<223> OTHER INFORMATION: G11 library peptide

<400> SEQUENCE: 263

Leu Lys Arg Lys Leu Lys Glu Ser Asn Met Gly
1               5                   10

<210> SEQ ID NO 264
<211> LENGTH: 11
<212> TYPE: PRT
<213> ORGANISM: Artificial Sequence
<220> FEATURE:
<223> OTHER INFORMATION: G11 library peptide

<400> SEQUENCE: 264

Leu Lys Arg Lys Val Lys Glu Tyr Asn Leu Gly
1               5                   10

<210> SEQ ID NO 265
<211> LENGTH: 19

```
<212> TYPE: DNA
<213> ORGANISM: Artificial Sequence
<220> FEATURE:
<223> OTHER INFORMATION: Reverse primer

<400> SEQUENCE: 265
gaaaatcttc tctcatccg                                                    19

<210> SEQ ID NO 266
<211> LENGTH: 11
<212> TYPE: PRT
<213> ORGANISM: Artificial Sequence
<220> FEATURE:
<223> OTHER INFORMATION: Gt library peptide

<400> SEQUENCE: 266

Ile Leu Glu Asn Leu Lys Asp Cys Gly Leu Leu
1               5                   10

<210> SEQ ID NO 267
<211> LENGTH: 9
<212> TYPE: DNA
<213> ORGANISM: Homo sapiens

<400> SEQUENCE: 267 gccgccacc                                                                9

<210> SEQ ID NO 268
<211> LENGTH: 57
<212> TYPE: DNA
<213> ORGANISM: Artificial Sequence
<220> FEATURE:
<223> OTHER INFORMATION: Gi alpha 1/2 carboxy terminal sequence
      oligonucleotide

<400> SEQUENCE: 268
gatccgccgc caccatggga atcaagaaca acctgaagga ctgcggcctc ttctgaa          57

<210> SEQ ID NO 269
<211> LENGTH: 57
<212> TYPE: DNA
<213> ORGANISM: Artificial Sequence
<220> FEATURE:
<223> OTHER INFORMATION: complementary strand to Gi alpha 1/2
      oligonucleotide

<400> SEQUENCE: 269
agctttcaga agaggccgca gtccttcagg ttgttcttga ttcccatggt ggcggcg          57

<210> SEQ ID NO 270
<211> LENGTH: 19
<212> TYPE: DNA
<213> ORGANISM: Artificial Sequence
<220> FEATURE:
<223> OTHER INFORMATION: forward primer for G alpha carboxyl terminal
      peptide insert

<400> SEQUENCE: 270
atccgccgcc accatggga                                                    19

<210> SEQ ID NO 271
<211> LENGTH: 20
<212> TYPE: DNA
<213> ORGANISM: Artificial Sequence
<220> FEATURE:
<223> OTHER INFORMATION: reverse primer for G alpha carboxyl terminal
      peptide insert
```

```
<400> SEQUENCE: 271
gcgaaaggag cggggcgcta                                                    20
```